US011279948B2

(12) United States Patent
Shen et al.

(10) Patent No.: US 11,279,948 B2
(45) Date of Patent: Mar. 22, 2022

(54) GENETICALLY MODIFIED NON-HUMAN ANIMAL WITH HUMAN OR CHIMERIC OX40

(71) Applicant: Biocytogen Pharmaceuticals (Beijing) Co., Ltd., Beijing (CN)

(72) Inventors: Yuelei Shen, Beijing (CN); Chaoshe Guo, Beijing (CN); Yang Bai, Beijing (CN); Jiawei Yao, Beijing (CN); Meiling Zhang, Beijing (CN); Xiaofei Zhou, Beijing (CN)

(73) Assignee: Biocytogen Pharmaceuticals (Beijing) Co., Ltd., Beijing (CN)

( * ) Notice: Subject to any disclaimer, the term of this patent is extended or adjusted under 35 U.S.C. 154(b) by 33 days.

(21) Appl. No.: 16/329,269

(22) PCT Filed: Aug. 30, 2017

(86) PCT No.: PCT/CN2017/099575
§ 371 (c)(1),
(2) Date: Feb. 28, 2019

(87) PCT Pub. No.: WO2018/041119
PCT Pub. Date: Mar. 8, 2018

(65) Prior Publication Data

US 2019/0352666 A1 Nov. 21, 2019

(30) Foreign Application Priority Data

Aug. 31, 2016 (CN) ......................... 201610775392.8
Aug. 29, 2017 (CN) ......................... 201710757005.2

(51) Int. Cl.
*C12N 15/85* (2006.01)
*A01K 67/027* (2006.01)
*C07K 14/705* (2006.01)

(52) U.S. Cl.
CPC ...... *C12N 15/8509* (2013.01); *A01K 67/0276* (2013.01); *A01K 67/0278* (2013.01); *C07K 14/70578* (2013.01); *A01K 2207/15* (2013.01); *A01K 2217/052* (2013.01); *A01K 2217/075* (2013.01); *A01K 2227/105* (2013.01); *A01K 2267/03* (2013.01); *A01K 2267/0393* (2013.01); *C12N 2015/8572* (2013.01)

(58) Field of Classification Search
CPC .................................................. A01K 67/0278
See application file for complete search history.

(56) References Cited

U.S. PATENT DOCUMENTS

| | | | |
|---|---|---|---|
| 4,683,195 | A | 7/1987 | Mullis et al. |
| 9,006,399 | B2 | 4/2015 | Liu et al. |
| 2002/0115209 | A1 | 8/2002 | Liu et al. |
| 2014/0309487 | A1 | 10/2014 | Lee et al. |
| 2016/0157470 | A1 | 6/2016 | Cagan et al. |

FOREIGN PATENT DOCUMENTS

| | | |
|---|---|---|
| AU | 2018262156 | 11/2019 |
| CN | 104561095 | 4/2015 |
| CN | 104567095 | 4/2015 |
| CN | 105296518 | 2/2016 |
| CN | 104593418 | 5/2016 |
| EP | 1525223 | 11/2007 |
| WO | WO 2004/039840 | 5/2004 |
| WO | WO 2007/062245 | 5/2007 |
| WO | WO 2009/091826 | 7/2009 |
| WO | WO 2013/038191 | 3/2013 |
| WO | WO 2015/153513 | 10/2015 |
| WO | WO 2018/177220 | 10/2018 |

OTHER PUBLICATIONS

Patil et al., 2011 (Indian Journal of Public Health research & Development, vol. 2, No. 1, p. 106-109).*
Khodarovich et al., 2013, Applied Biochemistry and Microbiology, vol. 49, No. 9, pp. 711-722.*
Guo et al., 2015 (Cell Research, vol. 25, p. 767-768.*
Lee et al., 2016, Drug Discovery Today: Disease Models, vol. 20, p. 13-20.*
Bryan et al., (2013 http://www.elsevierblogs.com/currentcomments/?p=962, Implications of protein fold switching, p. 1-4).*
Dombrowicz (1996, J Immunol, 157:1645-1651) (Year: 1996).*
Gordley (2016, Curr Opin Struct Biol, 39:106-114) (Year: 2016).*
Hemmi (1992, PNAS, 89:2737-2741) (Year: 1992).*
Guest (2005, Journal of Immunotherapy, 28:203-211) (Year: 2005).*
Byun et al., "Inherited human OX40 deficiency underlying classic Kaposi sarcoma of childhood," J. Exp. Med, 2013, 210:1743-1759.
GenBank Accession No. KJ891470.1, "Synthetic construct *Homo sapiens* clone ccsbBroadEn_00864 TNFRSF9 gene, encodes complete protein," GenBank, May 28, 2014, 3 pages.
GenBank Accession No. XM011250228.2, "Predicted: Mus musculus tumor necrosis factor receptor superfamily, member 9 (Tnfrsf9), transcript variant X1, mRNA," GenBank, Jun. 22, 2016.
Genbank Accession No. NM 003327, Mar. 15, 2015, https://www.ncbi.nInn.nih.gov/nuccore/315360637?sat=21&satkey=51816350, accessed Jan. 15, 2020).
Genbank Accession No. NM 011659, Feb. 15, 2015, https://www.ncbi.nInn.nih.gov/nuccore/118130086?sat=46&satkey=37204760, accessed Jan. 15, 2020).
Maksinnenko et al., "Use of transgenic animals in biotechnology: prospects and problems," Acta Naturae, 2013, 5(1):33-46.
Morales-Kastresana et al., "Combined immunostimulatory monoclonal antibodies extend survival in an aggressive transgenic hepatocellular carcinoma mouse model," Cancer Therapy, 2013, 19:6151-6162.
Croft et al., "The significance of OX40 and OX40L to T cell biology and immune disease," Immunol Rev., Apr. 2009, 229(1): 28 pages.
Kvarnhammar et al., "The CTLA-4 x OX40 bispecific antibody ATOR-1015 induces anti-tumor effects through tumor-directed immune activation," Journal for ImmunoTherapy of Cancer, Apr. 2019, 7(103): 14 pages.

(Continued)

*Primary Examiner* — Valarie E Bertoglio
(74) *Attorney, Agent, or Firm* — Fish & Richardson P.C.

(57) ABSTRACT

The present disclosure relates to the genetically modified non-human animals that express a human or chimeric OX40, and methods of use thereof.

11 Claims, 21 Drawing Sheets

Specification includes a Sequence Listing.

(56) References Cited

OTHER PUBLICATIONS

Scheer et al., "In vivo responses of the human and murine pregnane X receptor to dexamethasone in mice," DMD, Jul. 2010, 38(7): 1046-1053.
Zhu et al., "Humanising the mouse genome piece by piece," Nature Communications, Apr. 2019, 10(1845): 13 pages.
Auerbach et al., "Establishment and Chimera Analysis of 129/SvEv- and C57BL/6-Derived Mouse Embryonic Stem Cell Lines," BioTechniques, 2000. 29:1024-1032.
Festing et al., "Revised nomenclature for strain 129 mice," Mammalian Genome, 1999. 10(8):836.
GenBank Accession No. NM_003327.3, "*Homo sapiens* TNF receptor superfamily member 4 (TNFRSF4), mRNA," Jul. 2, 2016.
GenBank Accession No. NM_011659.2, "Mus musculus tumor necrosis factor receptor superfamily, member 4 (Tnfrsf4), mRNA," GenBank, Feb. 15, 2015.
Ito, M. et al., "NOD/SCID/ ycnull mouse: an excellent recipient mouse model for engraftment of human cells," Blood, 2002, 100(9):3175-3182.
Lute et al., "Human CTLA4 knock-in mice unravel the quantitative link between tumor immunity and autoimmunity induced by anti-CTLA-4 antibodies." Blood, 2011, 106(9):3127-3133.
PCT Written Opinion in International Appln. No. PCT/CN2017/099575, dated Nov. 14, 2011, 5 pages.
PCT International Preliminary Report on Patentability in Int. Appln. No. PCT/CN2017/099575. dated Mar. 5, 2019, 6 pages.
PCT International Search Report in International Appln. No. PCT/CN2017/099575, dated Nov. 20, 2017, 7 pages.
Sanmamed et al., "Defining the optimal Murine models to investigate immune checkpoint blockers and their combination with other immunotherapies." Annals. Of Oncology, 2016,27(7): 1190-1198.
Yin et al., "Delivery technologies for genome editing." Nature Reviews Drag Discovery, 2017, 16(6)387-399.
GenBank Accession No. AX781381.1, "Sequence 1 from Patent WO03026693," Jul. 14, 2003, 1 Page.
GenBank Accession No. X85214.1, "M.musculus ox40 gene," Nov. 14, 2006, 2 Pages.
Extended European Search Report and Written Opinion in European Appln. No. 17845421, dated Jan. 21, 2020, 8 pages.
Baum et al., "Molecular characterization of murine and human OX40/OX40 ligand systems: identification of a human OX40 ligand as the HTLV-1-regulated protein gp34," The EMBO journal, Sep. 1994, 13(17):3992-4001.
Croft et al., "Control of immunity by the TNFR-related molecule OX40 (CD134)," Annual review of immunology, Apr. 23, 2009, 28: 24 Pages.
Crownbio.com [online]. "OX40 Knock-In Mouse," published Jul. 22, 2017, retrieved Dec. 16, 2020, from https://www.crownbio.com/immuno-oncology/hugemm/ox40-mouse-model, 9 pages.
Guest et al., "The role of extracellular spacer regions in the optimal design of chimeric immune receptors: evaluation of four different scFvs and antigens," Journal of immunotherapy., May 1, 2005, 28(3):203-211.
Hellyer et al., "ErbB3 (HER3) interaction with the p85 regulatory subunit of phosphoinositide 3-kinase," Biochemical Journal, Aug. 1, 1998, 333(3):757-763.
Weinberg et al., "Science gone translational: the OX40 agonist story," Immunological reviews, Nov. 2011, 244(1):218-231.
Willoughby et al., "OX40: Structure and function—What questions remain?" Molecular immunology, Mar. 1, 2017, 83:13-22.
Dow et al., "Inducible in vivo genome editing with CRISPR-Cas9," Nature biotechnology, Apr. 2015, 33(4):390-394.
Liu et al., "Pronuclear microinjection and oviduct transfer procedures for transgenic mouse production,," Methods Mol Biol., 2013, 1027: 15 pages.

* cited by examiner

| Score | Expect | Method | Identities | Positives | Gaps |
|---|---|---|---|---|---|
| 263 bits(672) | 7e-93 | Compositional matrix adjust. | 160/251(64%) | 180/251(71%) | 5/251(1%) |

```
Mouse  25   LNCVKHTYPSGHKCCRECQPGHGMVSRCDHTRDTLCHPCETGFYNEAVNYDTCKQCTQCN  84
            L+CV  TYPS  +CC EC+PG+GMVSRC  +++T+C PC  GFYN+ V+   CK CT CN
Human  29   LHCVGDTYPSNDRCCHECRPGNGMVSRCSRSQNTVCRPCGPGFYNDVVSSKPCKPCTWCN  88

Mouse  85   HRSGSELKQNCTPTQDTVCRCRPGTQPRQDSGYKLGVDCVPCPPGHFSPGNNQACKPWTN  144
             RSGSE KQ CT TQDTVCRCR GTQP     YK GVDC PCPPGHFSPG+NQACKPWTN
Human  89   LRSGSERKQLCTATQDTVCRCRAGTQPLDS--YKPGVDCAPCPPGHFSPGDNQACKPWTN  146

Mouse  145  CTLSGKQTRHPASDSLDAVCEDRSLLATLLWETQRPTFRPTTVQSTTVWPRTSELPSPPT  204
            CTL+GK T  PAS+S DA+CEDR   AT   ETQ P  RP TVQ T  WPRTS+ PS
Human  147  CTLAGKHTLQPASNSSDAICEDRDPPATQPQETQGPPARPITVQPTEAWPRTSQGPSTRP  206

Mouse  205  LVTPEGPAFAVL--LGLGLGLLAPLTVLLALYLLRKAWRL-PNTPKPCWGNSFRTPIQEE  261
+  P G A A +  LGL LGLL PL +LLALYLLR+  RL P+  KP  G SFRTPIQEE
Human  207  VEVPGGRAVAAILGLGLVLGLLGPLAILLALYLLRRDQRLPPDAHKPPGGGSFRTPIQEE  266

Mouse  262  HTDAHFTLAKI  272
              DAH TLAKI
Human  267  QADAHSTLAKI  277
```

FIG. 21

```
                         SEQUENCE LISTING


<160> NUMBER OF SEQ ID NOS: 62

<210> SEQ ID NO 1
<211> LENGTH: 23
<212> TYPE: DNA
<213> ORGANISM: Artificial
<220> FEATURE:
<223> OTHER INFORMATION: sgRNA target sequence

<400> SEQUENCE: 1

gttaaacata cctaccccag tgg                                               23


<210> SEQ ID NO 2
<211> LENGTH: 23
<212> TYPE: DNA
<213> ORGANISM: Artificial
<220> FEATURE:
<223> OTHER INFORMATION: sgRNA target sequence

<400> SEQUENCE: 2

cgacagcact tgtgaccact ggg                                               23


<210> SEQ ID NO 3
<211> LENGTH: 23
<212> TYPE: DNA
<213> ORGANISM: Artificial
<220> FEATURE:
<223> OTHER INFORMATION: sgRNA target sequence

<400> SEQUENCE: 3

tcaaagccag gctactcacc tgg                                               23


<210> SEQ ID NO 4
<211> LENGTH: 23
<212> TYPE: DNA
<213> ORGANISM: Artificial
<220> FEATURE:
<223> OTHER INFORMATION: sgRNA target sequence

<400> SEQUENCE: 4

tgctgtcgtg agtgccagcc agg                                               23


<210> SEQ ID NO 5
<211> LENGTH: 23
<212> TYPE: DNA
<213> ORGANISM: Artificial
<220> FEATURE:
<223> OTHER INFORMATION: sgRNA target sequence

<400> SEQUENCE: 5

tgccagccag gtgagtagcc tgg                                               23
```

<210> SEQ ID NO 6
<211> LENGTH: 23
<212> TYPE: DNA
<213> ORGANISM: Artificial
<220> FEATURE:
<223> OTHER INFORMATION: sgRNA target sequence

<400> SEQUENCE: 6
agccaggcta ctcacctggc tgg 23

<210> SEQ ID NO 7
<211> LENGTH: 23
<212> TYPE: DNA
<213> ORGANISM: Artificial
<220> FEATURE:
<223> OTHER INFORMATION: sgRNA target sequence

<400> SEQUENCE: 7
gcacttgtga ccactggggt agg 23

<210> SEQ ID NO 8
<211> LENGTH: 23
<212> TYPE: DNA
<213> ORGANISM: Artificial
<220> FEATURE:
<223> OTHER INFORMATION: sgRNA target sequence

<400> SEQUENCE: 8
ttggcctgaa tgtagggcgc tgg 23

<210> SEQ ID NO 9
<211> LENGTH: 23
<212> TYPE: DNA
<213> ORGANISM: Artificial
<220> FEATURE:
<223> OTHER INFORMATION: sgRNA target sequence

<400> SEQUENCE: 9
agacccagcg ccctacattc agg 23

<210> SEQ ID NO 10
<211> LENGTH: 23
<212> TYPE: DNA
<213> ORGANISM: Artificial
<220> FEATURE:
<223> OTHER INFORMATION: sgRNA target sequence

<400> SEQUENCE: 10
acagtggttg gcctgaatgt agg 23

<210> SEQ ID NO 11
<211> LENGTH: 23
<212> TYPE: DNA
<213> ORGANISM: Artificial
<220> FEATURE:
<223> OTHER INFORMATION: sgRNA target sequence

<400> SEQUENCE: 11
gactgtggtg gattggacag tgg 23

<210> SEQ ID NO 12
<211> LENGTH: 23
<212> TYPE: DNA
<213> ORGANISM: Artificial
<220> FEATURE:
<223> OTHER INFORMATION: sgRNA target sequence

<400> SEQUENCE: 12
ctgtccaatc caccacagtc tgg 23

<210> SEQ ID NO 13
<211> LENGTH: 23
<212> TYPE: DNA
<213> ORGANISM: Artificial
<220> FEATURE:
<223> OTHER INFORMATION: sgRNA target sequence

<400> SEQUENCE: 13
tgggccagac tgtggtggat tgg 23

<210> SEQ ID NO 14
<211> LENGTH: 23
<212> TYPE: DNA
<213> ORGANISM: Artificial
<220> FEATURE:
<223> OTHER INFORMATION: sgRNA target sequence

<400> SEQUENCE: 14
aatccaccac agtctggccc agg 23

<210> SEQ ID NO 15
<211> LENGTH: 23
<212> TYPE: DNA
<213> ORGANISM: Artificial
<220> FEATURE:
<223> OTHER INFORMATION: sgRNA target sequence

<400> SEQUENCE: 15
gagggcaact cagaagtcct ggg 23

<210> SEQ ID NO 16
<211> LENGTH: 19
<212> TYPE: DNA
<213> ORGANISM: Artificial
<220> FEATURE:
<223> OTHER INFORMATION: sgRNA sequence

<400> SEQUENCE: 16
ttaaacatac ctaccccag 19

<210> SEQ ID NO 17
<211> LENGTH: 23
<212> TYPE: DNA
<213> ORGANISM: Artificial
<220> FEATURE:
<223> OTHER INFORMATION: sgRNA sequence

<400> SEQUENCE: 17
taggttaaac atacctaccc cag 23

<210> SEQ ID NO 18
<211> LENGTH: 19
<212> TYPE: DNA
<213> ORGANISM: Artificial
<220> FEATURE:
<223> OTHER INFORMATION: sgRNA sequence

<400> SEQUENCE: 18
ctggggtagg tatgtttaa 19

<210> SEQ ID NO 19

<211> LENGTH: 23
<212> TYPE: DNA
<213> ORGANISM: Artificial
<220> FEATURE:
<223> OTHER INFORMATION: sgRNA sequence

<400> SEQUENCE: 19
aaacctgggg taggtatgtt taa 23

<210> SEQ ID NO 20
<211> LENGTH: 19
<212> TYPE: DNA
<213> ORGANISM: Artificial
<220> FEATURE:
<223> OTHER INFORMATION: sgRNA sequence

<400> SEQUENCE: 20
actgtggtgg attggacag 19

<210> SEQ ID NO 21
<211> LENGTH: 23
<212> TYPE: DNA
<213> ORGANISM: Artificial
<220> FEATURE:
<223> OTHER INFORMATION: sgRNA sequence

<400> SEQUENCE: 21
taggactgtg gtggattgga cag 23

<210> SEQ ID NO 22
<211> LENGTH: 19
<212> TYPE: DNA
<213> ORGANISM: Artificial
<220> FEATURE:
<223> OTHER INFORMATION: sgRNA sequence

<400> SEQUENCE: 22
ctgtccaatc caccacagt 19

<210> SEQ ID NO 23
<211> LENGTH: 23
<212> TYPE: DNA
<213> ORGANISM: Artificial
<220> FEATURE:
<223> OTHER INFORMATION: sgRNA sequence

<400> SEQUENCE: 23
aaacctgtcc aatccaccac agt 23

<210> SEQ ID NO 24
<211> LENGTH: 132
<212> TYPE: DNA
<213> ORGANISM: Artificial
<220> FEATURE:
<223> OTHER INFORMATION: sgRNA sequence

<400> SEQUENCE: 24
gaattctaat acgactcact atagggggtc ttcgagaaga cctgttttag agctagaaat 60
agcaagttaa aataaggcta gtccgttatc aacttgaaaa agtggcaccg agtcggtgct 120
tttaaaggat cc 132

<210> SEQ ID NO 25
<211> LENGTH: 1155
<212> TYPE: DNA
<213> ORGANISM: Mus musculus

<400> SEQUENCE: 25

```
ccaaagcact tcttagctta tcatgggact ctgcatacgc ctgtgccaaa tacacaggaa      60
cacgttcaca taccttcttg cctgtccgcc tactcttctt gccccacctc catagttctt     120
atagccacac cctgcaagga aaaaccccag actcctgtga aggcagaaag cagacaagga     180
tgtatgtgtg ggttcagcag cccacagccc ttctgctgct gggactcaca cttggagtta     240
cagcaaggcg gctcaactgt gttaaacata cctaccccag tggtcacaag tgctgtcgtg     300
agtgccagcc aggccatggt atggtgagcc gctgtgatca taccagggat actctatgtc     360
atccgtgtga gactggcttc tacaatgaag ctgtcaatta tgatacctgc aagcagtgta     420
cacagtgcaa ccatcgaagt ggaagtgaac tcaagcagaa ttgcacacct actcaggata     480
ctgtctgcag atgtagacca ggcacccaac ctcggcagga cagcggctac aagcttggag     540
ttgactgtgt tccctgccct cctggccact ttctccagg caacaaccag gcctgcaagc      600
cctggaccaa ttgtacctta tctggaaagc agacccgcca cccagccagt gacagcttgg     660
acgcagtctg tgaggacaga agcctcctgg ccacactgct ctgggagacc cagcgcccta     720
cattcaggcc aaccactgtc caatccacca cagtctggcc caggacttct gagttgccct     780
ctccacccac cttggtgact cctgagggcc ctgcatttgc tgttctccta ggcctgggcc     840
tgggcctgct ggctcccttg actgtcctgc tggccttgta cctgctccgg aaggcttgga     900
gattgcctaa cactcccaaa ccttgttggg gaaacagctt caggaccccg atccaggagg     960
aacacacaga cgcacacttt actctggcca agatctgagc attactacag gagtggattt    1020
tatggggcac ggacaaccca tatcctgatg cctgccagta ccctccacac cgttctaggt    1080
gctgggctgg ctctgggctt tcctatgtat gctatgcata ctacctgcct ggtggtgctc    1140
ctaataaaca tgcta                                                     1155
```

<210> SEQ ID NO 26
<211> LENGTH: 272
<212> TYPE: PRT
<213> ORGANISM: Mus musculus

<400> SEQUENCE: 26

```
Met Tyr Val Trp Val Gln Gln Pro Thr Ala Leu Leu Leu Leu Gly Leu
1               5                   10                  15

Thr Leu Gly Val Thr Ala Arg Arg Leu Asn Cys Val Lys His Thr Tyr
            20                  25                  30

Pro Ser Gly His Lys Cys Cys Arg Glu Cys Gln Pro Gly His Gly Met
        35                  40                  45

Val Ser Arg Cys Asp His Thr Arg Asp Thr Leu Cys His Pro Cys Glu
    50                  55                  60

Thr Gly Phe Tyr Asn Glu Ala Val Asn Tyr Asp Thr Cys Lys Gln Cys
65                  70                  75                  80

Thr Gln Cys Asn His Arg Ser Gly Ser Glu Leu Lys Gln Asn Cys Thr
                85                  90                  95

Pro Thr Gln Asp Thr Val Cys Arg Cys Arg Pro Gly Thr Gln Pro Arg
            100                 105                 110

Gln Asp Ser Gly Tyr Lys Leu Gly Val Asp Cys Val Pro Cys Pro Pro
        115                 120                 125

Gly His Phe Ser Pro Gly Asn Asn Gln Ala Cys Lys Pro Trp Thr Asn
    130                 135                 140

Cys Thr Leu Ser Gly Lys Gln Thr Arg His Pro Ala Ser Asp Ser Leu
```

```
145                 150                 155                 160

Asp Ala Val Cys Glu Asp Arg Ser Leu Leu Ala Thr Leu Leu Trp Glu
                165                 170                 175

Thr Gln Arg Pro Thr Phe Arg Pro Thr Thr Val Gln Ser Thr Thr Val
            180                 185                 190

Trp Pro Arg Thr Ser Glu Leu Pro Ser Pro Pro Thr Leu Val Thr Pro
        195                 200                 205

Glu Gly Pro Ala Phe Ala Val Leu Leu Gly Leu Gly Leu Gly Leu Leu
    210                 215                 220

Ala Pro Leu Thr Val Leu Leu Ala Leu Tyr Leu Leu Arg Lys Ala Trp
225                 230                 235                 240

Arg Leu Pro Asn Thr Pro Lys Pro Cys Trp Gly Asn Ser Phe Arg Thr
                245                 250                 255

Pro Ile Gln Glu Glu His Thr Asp Ala His Phe Thr Leu Ala Lys Ile
            260                 265                 270
```

<210> SEQ ID NO 27
<211> LENGTH: 1120
<212> TYPE: DNA
<213> ORGANISM: Homo sapiens

<400> SEQUENCE: 27

```
ccgcaaggaa aacccagact ctggcgacag cagagacgag gatgtgcgtg ggggctcggc     60

ggctgggccg cgggccgtgt gcggctctgc tcctcctggg cctggggctg agcaccgtga    120

cggggctcca ctgtgtcggg gacacctacc ccagcaacga ccggtgctgc cacgagtgca    180

ggccaggcaa cgggatggtg agccgctgca gccgctccca gaacacggtg tgccgtccgt    240

gcgggccggg cttctacaac gacgtggtca gctccaagcc gtgcaagccc tgcacgtggt    300

gtaacctcag aagtgggagt gagcggaagc agctgtgcac ggccacacag gacacagtct    360

gccgctgccg ggcgggcacc cagcccctgg acagctacaa gcctggagtt gactgtgccc    420

cctgccctcc agggcacttc tccccaggcg acaaccaggc ctgcaagccc tggaccaact    480

gcaccttggc tgggaagcac accctgcagc cggccagcaa tagctcggac gcaatctgtg    540

aggacaggga ccccccagcc acgcagcccc aggagaccca gggcccccg gccaggccca    600

tcactgtcca gcccactgaa gcctggccca gaacctcaca gggaccctcc acccggcccg    660

tggaggtccc cgggggccgt gcggttgccg ccatcctggg cctgggcctg gtgctggggc    720

tgctgggccc cctggccatc ctgctggccc tgtacctgct ccggagggac cagaggctgc    780

cccccgatgc ccacaagccc cctgggggag gcagtttccg gacccccatc caagaggagc    840

aggccgacgc ccactccacc ctggccaaga tctgacctgg gcccaccaag gtggacgctg    900

ggccccgcca ggctggagcc cggagggtct gctgggcgag cagggcaggt gcaggccgcc    960

tgccccgcca cgctcctggg ccaactctgc accgttctag gtgccgatgg ctgcctccgg   1020

ctctctgctt acgtatgcca tgcatacctc ctgccccgcg ggaccacaat aaaaaccttg   1080

gcagacggga gtctccgacc ggcaaaaaaa aaaaaaaaaa                         1120
```

<210> SEQ ID NO 28
<211> LENGTH: 277
<212> TYPE: PRT
<213> ORGANISM: Homo sapiens

<400> SEQUENCE: 28

```
Met Cys Val Gly Ala Arg Arg Leu Gly Arg Gly Pro Cys Ala Ala Leu
1               5                   10                  15
```

```
Leu Leu Leu Gly Leu Gly Leu Ser Thr Val Thr Gly Leu His Cys Val
            20                  25                  30

Gly Asp Thr Tyr Pro Ser Asn Asp Arg Cys Cys His Glu Cys Arg Pro
        35                  40                  45

Gly Asn Gly Met Val Ser Arg Cys Ser Arg Ser Gln Asn Thr Val Cys
    50                  55                  60

Arg Pro Cys Gly Pro Gly Phe Tyr Asn Asp Val Val Ser Ser Lys Pro
65                  70                  75                  80

Cys Lys Pro Cys Thr Trp Cys Asn Leu Arg Ser Gly Ser Glu Arg Lys
                85                  90                  95

Gln Leu Cys Thr Ala Thr Gln Asp Thr Val Cys Arg Cys Arg Ala Gly
            100                 105                 110

Thr Gln Pro Leu Asp Ser Tyr Lys Pro Gly Val Asp Cys Ala Pro Cys
        115                 120                 125

Pro Pro Gly His Phe Ser Pro Gly Asp Asn Gln Ala Cys Lys Pro Trp
    130                 135                 140

Thr Asn Cys Thr Leu Ala Gly Lys His Thr Leu Gln Pro Ala Ser Asn
145                 150                 155                 160

Ser Ser Asp Ala Ile Cys Glu Asp Arg Asp Pro Pro Ala Thr Gln Pro
                165                 170                 175

Gln Glu Thr Gln Gly Pro Pro Ala Arg Pro Ile Thr Val Gln Pro Thr
            180                 185                 190

Glu Ala Trp Pro Arg Thr Ser Gln Gly Pro Ser Thr Arg Pro Val Glu
        195                 200                 205

Val Pro Gly Gly Arg Ala Val Ala Ala Ile Leu Gly Leu Gly Leu Val
    210                 215                 220

Leu Gly Leu Leu Gly Pro Leu Ala Ile Leu Leu Ala Leu Tyr Leu Leu
225                 230                 235                 240

Arg Arg Asp Gln Arg Leu Pro Pro Asp Ala His Lys Pro Pro Gly Gly
                245                 250                 255

Gly Ser Phe Arg Thr Pro Ile Gln Glu Glu Gln Ala Asp Ala His Ser
            260                 265                 270

Thr Leu Ala Lys Ile
        275
```

<210> SEQ ID NO 29
<211> LENGTH: 2065
<212> TYPE: DNA
<213> ORGANISM: Artificial
<220> FEATURE:
<223> OTHER INFORMATION: Homo sapiens and Mus musculus

<400> SEQUENCE: 29

```
tgttaaacat acatatccta gcaacgaccg gtgctgccac gagtgcaggc caggtgaggc      60

ctcaggaggg gtcgccacgc acgggcactc cagggactgg gggctggggc agggatgggc     120

cagccaggag gctggtcctg gggagggggc gggtgagggg ccggccaagc ctggcagagg     180

agccgcctgg gggggtccac gggcgcaagc ctggggcctg accgctgcct gacgccggcc     240

tctgctgcag gcaacgggat ggtgagccgc tgcagccgct cccagaacac ggtgtgccgt     300

ccgtgcgggc cgggcttcta caacgacgtg gtcagctcca agccgtgcaa gccctgcacg     360

tggtgtaacc tcagtgagct cccacctggc cccacagccc cacccagcac agggggcggc     420

agcctggcac ccacattccc acgcagcagc atggggctcc cacagccgca gaaacgaacc     480

tcaaaccaca gcggggtctg ctccgccaca ggggtccttc gaggagctga ggcgtctccc     540
```

```
aggggcaccc cctctccctc cgggggccca gactcggccc aggccacgtg gagtcgggga    600

gaccacgctg gccatgtggc ctggccttgc tggcctgagc agtgaggctg gggggttggg    660

ccatggagac cctgccgcag gcggggctgg cggctggagg cggtggaggg gtagggaagg    720

gtggctgggg ctgccacgga accagcccca ggttgtggcc aggaagggag ggcccaggag    780

cctcgggggc tgcaggggct ccaagtctca ggggaggccg cagacccctg cccacggccc    840

tctgtgtggt ggggaggcca acctgtcctc cagtgcccac gcttcctgag gaccctgtcc    900

acagccccca cctgaccacc cccccatccg gcccctgctc aggaagtggg agtgagcgga    960

agcagctgtg cacggccaca caggacacag tctgccgctg ccgggcgggc acccagcccc   1020

tggacagcta caagcctgga gttggtgagc tcggtggctg cggccggcgg ttgggggtgt   1080

gcatagcggc tgtctgtgac gcagatgggc cgtgggccgc agggacctgg ccccaccggt   1140

gcctcctctg gcatcctcaa gaccgagctc ccgggtcagg gcccacgggt gggatgtggg   1200

cagggagggc ttccagaggc caaacccacc acccagccat ggggggcaag tgcctgcccc   1260

acaggctctg ccccatgtcc ccagcacccg gggcctgtgg gcagcccctg accaccctat   1320

ctttgttgca gactgtgccc cctgccctcc agggcacttc tccccaggcg acaaccaggc   1380

ctgcaagccc tggaccaagt gaggggcctg gccaggggct gggaggggct ggggggggt   1440

tggggtggtt aggagggcgg aggagctggg gagctgggag gggctggggg ggcaggtggg   1500

gtgggggcag ttttgggga aggggaggtg ctggtggccc tgggggcctg gctatgtggc   1560

tggacctggt tggggagcag gaagctgctg cctgggggca gcctttccct gtgggtggag   1620

ctgggtgtgt gggaccctca ccctccgcag ctgggaggcc ctgggggcac aggacaggga   1680

ggtgctggtg gggggtgtag atgtgggaga agggtgtgtg gccttggagg cccctgtggg   1740

gggcacgtgg ggctgggcag cgtccttggc tgtcactggc ctggtgtctg tggtagatgc   1800

tgcctgtggc tggccagcgt ggaccctgtt atccccaccg catctcccgg gtcccagggg   1860

gtttctggcc tgagcaacac ctcctgttcc ccaacagctg caccttggct gggaagcaca   1920

ccctgcagcc ggccagcaat agctcggacg caatctgtga ggacagggac cccccagcca   1980

cgcagcccca ggagacccag ggcccccggg ccaggcccat cactgtccag cccactgaag   2040

cctggcccag aacttctgag ttgcc                                       2065
```

<210> SEQ ID NO 30
<211> LENGTH: 813
<212> TYPE: DNA
<213> ORGANISM: Artificial
<220> FEATURE:
<223> OTHER INFORMATION: Homo sapiens and Mus musculus

<400> SEQUENCE: 30

```
atgtatgtgt gggttcagca gcccacagcc cttctgctgc tgggactcac acttggagtt     60

acagcaaggc ggctcaactg tgttaaacat acatatccta gcaacgaccg gtgctgccac    120

gagtgcaggc caggcaacgg gatggtgagc cgctgcagcc gctcccagaa cacggtgtgc    180

cgtccgtgcg ggccgggctt ctacaacgac gtggtcagct ccaagccgtg caagccctgc    240

acgtggtgta acctcagaag tgggagtgag cggaagcagc tgtgcacggc cacacaggac    300

acagtctgcc gctgccgggc gggcacccag cccctggaca gctacaagcc tggagttgac    360

tgtgcccccct gccctccagg gcacttctcc ccaggcgaca accaggcctg caagccctgg    420

accaactgca ccttggctgg gaagcacacc ctgcagccgg ccagcaatag ctcggacgca    480
```

atctgtgagg acagggaccc cccagccacg cagccccagg agacccaggg ccccccggcc 540
aggcccatca ctgtccagcc cactgaagcc tggcccagaa cttctgagtt gccctctcca 600
cccaccttgg tgactcctga gggccctgca tttgctgttc tcctaggcct gggcctgggc 660
ctgctggctc ccttgactgt cctgctggcc ttgtacctgc tccggaaggc ttggagattg 720
cctaacactc ccaaaccttg ttggggaaac agcttcagga ccccgatcca ggaggaacac 780
acagacgcac actttactct ggccaagatc tga 813

<210> SEQ ID NO 31
<211> LENGTH: 1149
<212> TYPE: DNA
<213> ORGANISM: Artificial
<220> FEATURE:
<223> OTHER INFORMATION: Homo sapiens and Mus musculus

<400> SEQUENCE: 31
ccaaagcact tcttagctta tcatgggact ctgcatacgc ctgtgccaaa tacacaggaa 60
cacgttcaca taccttcttg cctgtccgcc tactcttctt gccccacctc catagttctt 120
atagccacac cctgcaagga aaaaccccag actcctgtga aggcagaaag cagacaagga 180
tgtatgtgtg ggttcagcag cccacagccc ttctgctgct gggactcaca cttggagtta 240
cagcaaggcg gctcaactgt gttaaacata catatcctag caacgaccgg tgctgccacg 300
agtgcaggcc aggcaacggg atggtgagcc gctgcagccg ctcccagaac acggtgtgcc 360
gtccgtgcgg gccgggcttc tacaacgacg tggtcagctc caagccgtgc aagccctgca 420
cgtggtgtaa cctcagaagt gggagtgagc ggaagcagct gtgcacggcc acacaggaca 480
cagtctgccg ctgccgggcg ggcacccagc ccctggacag ctacaagcct ggagttgact 540 gtgcccccctg ccctccaggg cacttctccc caggcgacaa ccaggcctgc aagccctgga 600
ccaactgcac cttggctggg aagcacaccc tgcagccggc cagcaatagc tcggacgcaa 660
tctgtgagga cagggacccc ccagccacgc agccccagga gacccagggc cccccggcca 720
ggcccatcac tgtccagccc actgaagcct ggcccagaac ttctgagttg ccctctccac 780
ccaccttggt gactcctgag ggccctgcat ttgctgttct cctaggcctg ggcctgggcc 840
tgctggctcc cttgactgtc ctgctggcct tgtacctgct ccggaaggct tggagattgc 900
ctaacactcc caaaccttgt tggggaaaca gcttcaggac cccgatccag gaggaacaca 960
cagacgcaca ctttactctg gccaagatct gagcattact acaggagtgg attttatggg 1020
gcacggacaa cccatatcct gatgcctgcc agtaccctcc acaccgttct aggtgctggg 1080
ctggctctgg gctttcctat gtatgctatg catactacct gcctggtggt gctcctaata 1140
aacatgcta 1149

<210> SEQ ID NO 32
<211> LENGTH: 265
<212> TYPE: PRT
<213> ORGANISM: Artificial
<220> FEATURE:
<223> OTHER INFORMATION: Homo sapiens and Mus musculus

<400> SEQUENCE: 32

Met Tyr Val Trp Val Gln Gln Pro Thr Ala Leu Leu Leu Leu Gly Leu
1 5 10 15

Thr Leu Gly Val Thr Ala Arg Arg Leu Asn Cys Val Lys His Thr Tyr
20 25 30

Cys Cys His Glu Cys Arg Pro Gly Asn Gly Met Val Ser Arg Cys Ser

```
        35                  40                  45

Arg Ser Gln Asn Thr Val Cys Arg Pro Cys Gly Pro Gly Phe Tyr Asn
    50                  55                  60

Asp Val Val Ser Ser Lys Pro Cys Lys Pro Cys Thr Trp Cys Asn Leu
65                  70                  75                  80

Arg Ser Gly Ser Glu Arg Lys Gln Leu Cys Thr Ala Thr Gln Asp Thr
                85                  90                  95

Val Cys Arg Cys Arg Ala Gly Thr Gln Pro Leu Asp Ser Tyr Lys Pro
            100                 105                 110

Gly Val Asp Cys Ala Pro Cys Pro Pro Gly His Phe Ser Pro Gly Asp
        115                 120                 125

Asn Gln Ala Cys Lys Pro Trp Thr Asn Cys Thr Leu Ala Gly Lys His
    130                 135                 140

Thr Leu Gln Pro Ala Ser Asn Ser Ser Asp Ala Ile Cys Glu Asp Arg
145                 150                 155                 160

Asp Pro Pro Ala Thr Gln Pro Gln Glu Thr Gln Gly Pro Pro Ala Arg
                165                 170                 175

Pro Ile Thr Val Gln Pro Thr Glu Ala Trp Pro Arg Thr Ser Glu Leu
            180                 185                 190

Pro Ser Pro Pro Thr Leu Val Thr Pro Glu Gly Pro Ala Phe Ala Val
        195                 200                 205

Leu Leu Gly Leu Gly Leu Gly Leu Leu Ala Pro Leu Thr Val Leu Leu
    210                 215                 220

Ala Leu Tyr Leu Leu Arg Lys Ala Trp Arg Leu Pro Asn Thr Pro Lys
225                 230                 235                 240

Pro Cys Trp Gly Asn Ser Phe Arg Thr Pro Ile Gln Glu Glu His Thr
                245                 250                 255

Asp Ala His Phe Thr Leu Ala Lys Ile
            260                 265
```

<210> SEQ ID NO 33
<211> LENGTH: 1244
<212> TYPE: DNA
<213> ORGANISM: Mus musculus

<400> SEQUENCE: 33

```
aatgtgtagt aaaggcactg ccccctgcta actcatttcc tccttcagtg cagtggtttg     60

agtgtaagaa aagaaggccc gcgttgagct cactgacaca cacctgtcgt cgcagcattt    120

gggaggtgga ggcaggaaga tggggggtac aaggtcatcg agatggttca ctcagtagaa    180

ctacttgcca caacccaaat ttggtcctca gtatcaacac catgcagctc acaactgcct    240

ataatctagc tctaggggga tcagacatct ctggcctcct agggccacgt gtaagtcccc    300

tcccccaaca tacacacaca cacacacaca cacacacaga gttaaaaata aatctctttt    360

taaaaatcta agcatgggct acagaatgag ttcaaatgtt agcctgggca acttagtgaa    420

actgttaaaa gaaaacatga agagagctgt ggctctagct cagtggtcga acgctgccca    480

gcaagtaaaa cgcttaggct cttagcatta taaaaaagga aggagaataa atccactggc    540

acggagagat ggctaagtag ttaagcttgt actgctctct tgggtgtttt tgtttttgag    600

acaaagtctc tcttatacaa tctggctgcc ctgagactta actatgtaga ctgggcagag    660

ctgcctgctt ccatctcctg agtactggct ttaaagaagt gtactgccat gcccagtggt    720

aagagcatgc gttcttgcag agaaccaaag ttcagtttcc agcactcatg atggtggttc    780

accactgcct ataactctag ctcttctgac ttccctgggc attatactta ccatacatat    840
```

```
acccttcccc ctcaaaaaag aaataaaatt aaaaataaat ttttttctta atgcctgtgt    900

gcacgtgtgt gtttctttgt gtgcttcgtg tgcatatgtt gggtatctgc acctctcttc    960

acgttcccca gcggcccaaa gcacttctta gcttatcatg ggactctgca tacgcctgtg   1020

ccaaatacac aggaacacgt tcacatacct tcttgcctgt ccgcctactc ttcttgcccc   1080

acctccatag ttcttatagc cacaccctgc aaggaaaaac cccagactcc tgtgaaggca   1140

gaaagcagac aaggatgtat gtgtgggttc agcagcccac agcccttctg ctgctgggac   1200

tcacacttgg agttacagca aggcggctca actgtgttaa acat                    1244
```

<210> SEQ ID NO 34
<211> LENGTH: 46
<212> TYPE: DNA
<213> ORGANISM: Artificial
<220> FEATURE:
<223> OTHER INFORMATION: PCR primer

<400> SEQUENCE: 34

```
tttaagaagg agatatacat gaatgtgtag taaaggcact gccccc                    46
```

<210> SEQ ID NO 35
<211> LENGTH: 42
<212> TYPE: DNA
<213> ORGANISM: Artificial
<220> FEATURE:
<223> OTHER INFORMATION: PCR primer

<400> SEQUENCE: 35

```
gttgctagga tatgtatgtt taacacagtt gagccgcctt gc                        42
```

<210> SEQ ID NO 36
<211> LENGTH: 2041
<212> TYPE: DNA
<213> ORGANISM: Homo sapiens

<400> SEQUENCE: 36

```
acatatccta gcaacgaccg gtgctgccac gagtgcaggc caggtgaggc ctcaggaggg     60

gtcgccacgc acgggcactc cagggactgg gggctggggc agggatgggc cagccaggag    120

gctggtcctg gggagggggc gggtgagggg ccggccaagc ctggcagagg agccgcctgg    180

gggggtccac gggcgcaagc ctggggcctg accgctgcct gacgccggcc tctgctgcag    240

gcaacgggat ggtgagccgc tgcagccgct cccagaacac ggtgtgccgt ccgtgcgggc    300

cgggcttcta caacgacgtg gtcagctcca agccgtgcaa gccctgcacg tggtgtaacc    360

tcagtgagct cccacctggc cccacagccc cacccagcac agggggcggc agcctggcac    420

ccacattccc acgcagcagc atggggctcc cacagccgca gaaacgaacc tcaaaccaca    480

gcggggtctg ctccgccaca ggggtccttc gaggagctga ggcgtctccc aggggcaccc    540

cctctccctc cgggggccca gactcggccc aggccacgtg gagtcgggga gaccacgctg    600

gccatgtggc ctggccttgc tggcctgagc agtgaggctg gggggttggg ccatggagac    660

cctgccgcag gcggggctgg cggctggagg cggtggaggg gtagggaagg gtggctgggg    720

ctgccacgga accagcccca ggttgtggcc aggaagggag ggcccaggag cctcgggggc    780

tgcaggggct ccaagtctca ggggaggccg cagacccctg cccacggccc tctgtgtggt    840

ggggaggcca acctgtcctc cagtgcccac gcttcctgag gaccctgtcc acagccccca    900

cctgaccacc cccccatccg gcccctgctc aggaagtggg agtgagcgga agcagctgtg    960
```

```
cacggccaca caggacacag tctgccgctg ccgggcgggc acccagcccc tggacagcta   1020

caagcctgga gttggtgagc tcggtggctg cggccggcgg ttgggggtgt gcatagcggc   1080

tgtctgtgac gcagatgggc cgtgggccgc agggacctgg ccccaccggt gcctcctctg   1140

gcatcctcaa gaccgagctc ccgggtcagg gcccacgggt gggatgtggg cagggagggc   1200

ttccagaggc caaacccacc acccagccat ggggggcaag tgcctgcccc acaggctctg   1260

ccccatgtcc ccagcacccg gggcctgtgg gcagcccctg accaccctat ctttgttgca   1320

gactgtgccc cctgccctcc agggcacttc tccccaggcg acaaccaggc ctgcaagccc   1380

tggaccaagt gaggggcctg gccaggggct gggaggggct gggggggggt tggggtggtt   1440

aggagggcgg aggagctggg gagctgggag gggctggggg ggcaggtggg gtgggggcag   1500

ttttggggga aggggaggtg ctggtggccc tgggggcctg gctatgtggc tggacctggt   1560

tggggagcag gaagctgctg cctgggggca gcctttccct gtgggtggag ctgggtgtgt   1620

gggaccctca ccctccgcag ctgggaggcc ctgggggcac aggacaggga ggtgctggtg   1680

gggggtgtag atgtgggaga agggtgtgtg gccttggagg cccctgtggg gggcacgtgg   1740

ggctgggcag cgtccttggc tgtcactggc ctggtgtctg tggtagatgc tgcctgtggc   1800

tggccagcgt ggaccctgtt atccccaccg catctcccgg gtcccagggg gtttctggcc   1860

tgagcaacac ctcctgttcc ccaacagctg caccttggct gggaagcaca ccctgcagcc   1920

ggccagcaat agctcggacg caatctgtga ggacagggac cccccagcca cgcagcccca   1980

ggagacccag ggcccccggg ccaggcccat cactgtccag cccactgaag cctggcccag   2040

a                                                                   2041
```

```
<210> SEQ ID NO 37
<211> LENGTH: 40
<212> TYPE: DNA
<213> ORGANISM: Artificial
<220> FEATURE:
<223> OTHER INFORMATION: PCR primer

<400> SEQUENCE: 37

gtgttaaaca tacatatcct agcaacgacc ggtgctgcca                           40


<210> SEQ ID NO 38
<211> LENGTH: 41
<212> TYPE: DNA
<213> ORGANISM: Artificial
<220> FEATURE:
<223> OTHER INFORMATION: PCR primer

<400> SEQUENCE: 38

ctcagaagtt ctgggccagg cttcagtggg ctggacagtg a                         41


<210> SEQ ID NO 39
<211> LENGTH: 1165
<212> TYPE: DNA
<213> ORGANISM: Mus musculus

<400> SEQUENCE: 39

acttctgagt tgccctctcc acccaccttg gtgactcctg agggtaaggg acactggcgc     60

agtggaggat agggagagaa ctcaagggtg agcgagttta ctcagttggc ctctcctcat    120

aggccctgca tttgctgttc tcctaggcct gggcctgggc ctgctggctc ccttgactgt    180

cctgctggcc ttgtacctgc tccggaaggc ttggagattg cctaacactc ccaaaccttg    240

ttgtgagtat cacattgggc tcagtaaagc ctacctcctt cacgatgagc catagctcct    300
```

cactgctctt tccttctgtg cttctcttag ggggaaacag cttcaggacc ccgatccagg 360
aggaacacac agacgcacac tttactctgg ccaagatctg agcattacta caggagtgga 420
ttttatgggg cacggacaac ccatatcctg atgcctgcca gtaccctcca caccgttcta 480
ggtgctgggc tggctctggg ctttcctatg tatgctatgc atactacctg cctggtggtg 540
ctcctaataa acatgctagc agctgtgagt ctgtgactgg cactagggct gaggtggcct 600
cctattctgg ttggggaggg tttggggcca aaatgaaggt ccactcagag acctacactt 660
ggtcacatgt actccagtgt gagtacgggt atggaattca gagacctgaa atgccaaggg 720
gaaagtacct ggggagccaa ctggcaactc gatgagcagt ccagagtctt actctaaggc 780
aggggttctc agccttctta gtgctgtgac ccttttaata cagtttcaca tgttgtggtg 840
gccccaaacc atgaaactgt tttctttgcc tctttttttt tccatctttt attattatta 900
ttattattag gtattttcct cgtttacatt ttcaatgcta tcccaaaggt cccccatacc 960 cacccccccaa tcccctaccc acccttcttt gccttttgat aacaatagtt ttgctactgt 1020
tatgaatcat aatgcaagta ttattgagat agaggtttgc ctaaagggct gcagcacaca 1080
ggttaagaaa cactgctcta agtggaccta agagtcttag ccaaatggaa aagtcctggc 1140
aagcagagcc taagtaccga ggtca 1165

<210> SEQ ID NO 40
<211> LENGTH: 46
<212> TYPE: DNA
<213> ORGANISM: Artificial
<220> FEATURE:
<223> OTHER INFORMATION: PCR primer

<400> SEQUENCE: 40
ccactgaagc ctggcccaga acttctgagt tgccctctcc acccac 46

<210> SEQ ID NO 41
<211> LENGTH: 45
<212> TYPE: DNA
<213> ORGANISM: Artificial
<220> FEATURE:
<223> OTHER INFORMATION: PCR primer

<400> SEQUENCE: 41
gttgttagca gccggatctc agtgacctcg gtacttaggc tctgc 45

<210> SEQ ID NO 42
<211> LENGTH: 25
<212> TYPE: DNA
<213> ORGANISM: Artificial
<220> FEATURE:
<223> OTHER INFORMATION: PCR primer

<400> SEQUENCE: 42
atttccagcc ccagtcctat tccct 25

<210> SEQ ID NO 43
<211> LENGTH: 25
<212> TYPE: DNA
<213> ORGANISM: Artificial
<220> FEATURE:
<223> OTHER INFORMATION: PCR primer

<400> SEQUENCE: 43
ctcggtcttg aggatgccag aggag 25

<210> SEQ ID NO 44
<211> LENGTH: 19
<212> TYPE: DNA
<213> ORGANISM: Artificial
<220> FEATURE:
<223> OTHER INFORMATION: PCR primer

<400> SEQUENCE: 44
ctcaggaggg gtcgccacg 19

<210> SEQ ID NO 45
<211> LENGTH: 27
<212> TYPE: DNA
<213> ORGANISM: Artificial
<220> FEATURE:
<223> OTHER INFORMATION: PCR primer

<400> SEQUENCE: 45
ctcaccattc atgtggctgg agagaaa 27

<210> SEQ ID NO 46
<211> LENGTH: 25
<212> TYPE: DNA
<213> ORGANISM: Artificial
<220> FEATURE:
<223> OTHER INFORMATION: PCR primer

<400> SEQUENCE: 46
tcttccctgc agtttttagg ggcag 25

<210> SEQ ID NO 47
<211> LENGTH: 25
<212> TYPE: DNA
<213> ORGANISM: Artificial
<220> FEATURE:
<223> OTHER INFORMATION: PCR primer

<400> SEQUENCE: 47
agtccccagt cctctcatgg aaaca 25

<210> SEQ ID NO 48
<211> LENGTH: 25
<212> TYPE: DNA
<213> ORGANISM: Artificial
<220> FEATURE:
<223> OTHER INFORMATION: PCR primer

<400> SEQUENCE: 48
gtgagcgagt ttactcagtt ggcct 25

<210> SEQ ID NO 49
<211> LENGTH: 25
<212> TYPE: DNA
<213> ORGANISM: Artificial
<220> FEATURE:
<223> OTHER INFORMATION: PCR primer

<400> SEQUENCE: 49
ctagtgccag tcacagactc acagc 25

<210> SEQ ID NO 50
<211> LENGTH: 20
<212> TYPE: DNA
<213> ORGANISM: Artificial
<220> FEATURE:
<223> OTHER INFORMATION: PCR primer

<400> SEQUENCE: 50
gtcatccgtg tgagactggc 20

<210> SEQ ID NO 51
<211> LENGTH: 20
<212> TYPE: DNA
<213> ORGANISM: Artificial
<220> FEATURE:
<223> OTHER INFORMATION: PCR primer

<400> SEQUENCE: 51
ccagactgtg gtggattgga 20

<210> SEQ ID NO 52
<211> LENGTH: 20
<212> TYPE: DNA
<213> ORGANISM: Artificial
<220> FEATURE:
<223> OTHER INFORMATION: PCR primer

<400> SEQUENCE: 52
gccctgcacg tggtgtaacc 20

<210> SEQ ID NO 53
<211> LENGTH: 20
<212> TYPE: DNA
<213> ORGANISM: Artificial
<220> FEATURE:
<223> OTHER INFORMATION: PCR primer

<400> SEQUENCE: 53
acagtgatgg gcctggccgg 20

<210> SEQ ID NO 54
<211> LENGTH: 25
<212> TYPE: DNA
<213> ORGANISM: Artificial
<220> FEATURE:
<223> OTHER INFORMATION: PCR primer

<400> SEQUENCE: 54
tagggtaggg gtttgaaagg gcaga 25

<210> SEQ ID NO 55
<211> LENGTH: 25
<212> TYPE: DNA
<213> ORGANISM: Artificial
<220> FEATURE:
<223> OTHER INFORMATION: PCR primer

<400> SEQUENCE: 55
cccaggccta ggagaacagc aaatg 25

<210> SEQ ID NO 56
<211> LENGTH: 25
<212> TYPE: DNA
<213> ORGANISM: Artificial
<220> FEATURE:
<223> OTHER INFORMATION: PCR primer

<400> SEQUENCE: 56
gaccctgtta tccccaccgc atctc 25

<210> SEQ ID NO 57

<211> LENGTH: 25
<212> TYPE: DNA
<213> ORGANISM: Artificial
<220> FEATURE:
<223> OTHER INFORMATION: PCR primer

<400> SEQUENCE: 57
cttccacatg agcgtggtca gggcc 25

<210> SEQ ID NO 58
<211> LENGTH: 25
<212> TYPE: DNA
<213> ORGANISM: Artificial
<220> FEATURE:
<223> OTHER INFORMATION: PCR primer

<400> SEQUENCE: 58
ccaagggact attttagatg ggcag 25

<210> SEQ ID NO 59
<211> LENGTH: 26
<212> TYPE: DNA
<213> ORGANISM: Artificial
<220> FEATURE:
<223> OTHER INFORMATION: PCR primer

<400> SEQUENCE: 59
gaagctacaa gctcctaggt aggggg 26

<210> SEQ ID NO 60
<211> LENGTH: 23
<212> TYPE: DNA
<213> ORGANISM: Artificial
<220> FEATURE:
<223> OTHER INFORMATION: PCR primer

<400> SEQUENCE: 60
acgggttggc tcaaaccatt aca 23

<210> SEQ ID NO 61
<211> LENGTH: 25
<212> TYPE: DNA
<213> ORGANISM: Artificial
<220> FEATURE:
<223> OTHER INFORMATION: PCR primer

<400> SEQUENCE: 61
cccagactcc tgtgaaggca gaaag 25

<210> SEQ ID NO 62
<211> LENGTH: 25
<212> TYPE: DNA
<213> ORGANISM: Artificial
<220> FEATURE:
<223> OTHER INFORMATION: PCR primer

<400> SEQUENCE: 62
aggaggtagg ctttactgag cccaa 25

GENETICALLY MODIFIED NON-HUMAN ANIMAL WITH HUMAN OR CHIMERIC OX40

CLAIM OF PRIORITY

This application claims the benefit of Chinese Patent Application App. No. 201610775392.8, filed on Aug. 31, 2016, and App. No. 201710757005.2, filed on Aug. 29, 2017. The entire contents of the foregoing are incorporated herein by reference.

TECHNICAL FIELD

This disclosure relates to genetically modified animal expressing human or chimeric (e.g., humanized) OX40 (TNF Receptor Superfamily Member 4, or TNFRSF4), and methods of use thereof.

BACKGROUND

Cancer is currently one of the diseases that have the highest human mortality. According to the World Health Organization statistical data, in 2012 the number of global cancer incidence and death cases reached 14 million and 8.2 million, respectively. In China, the newly diagnosed cancer cases are 3.07 million, and the death toll is 2.2 million.

In recent years, antibody drug development for immunological checkpoints is considered to be a potential target for the treatment of various types of cancers. The traditional drug research and development typically use in vitro screening approaches. However, these screening approaches cannot provide the body environment (such as tumor microenvironment, stromal cells, extracellular matrix components and immune cell interaction, etc.), resulting in a higher rate of failure in drug development. In addition, in view of the differences between humans and animals, the test results obtained from the use of conventional experimental animals for in vivo pharmacological test may not be able to reflect the real disease state and the identification and interaction at the targeting sites, resulting in that the results in many clinical trials are significantly different from the animal experimental results. Therefore, the development of humanized animal models that are suitable for human antibody screening and evaluation will significantly improve the efficiency of new drug development and reduce the costs for drug research and development.

SUMMARY

This disclosure is related to OX40 humanized animal model. The animal model can express human OX40 or chimeric OX40 (e.g., humanized OX40) protein in its body. It can be used in the studies on the function of OX40 gene, and can be used in the screening and evaluation of anti-human OX40 antibodies. In addition, the animal models prepared by the methods described herein can be used in drug screening, pharmacodynamics studies, treatments for immune-related diseases, and cancer therapy for human OX40 target sites; in addition, they can be used to facilitate the development and design of new drugs, and save time and cost. In summary, this disclosure provides a powerful tool for studying the function of OX40 protein and screening for cancer drugs.

Furthermore, the disclosure also provides OX40 gene knockout mice. Moreover, the mice described in the present disclosure can be mated with the mice containing other human or chimeric genes (e.g., chimeric PD-1 or other immunomodulatory factors), so as to obtain a mouse having a human or chimeric protein at both alleles of the endogenous gene. The mice can also, e.g., be used for screening antibodies in the case of a combined use of drugs, as well as evaluating the efficacy of the combination therapy.

In one aspect, the disclosure relates to genetically-modified, non-human animals whose genome comprises at least one chromosome comprising a sequence encoding a human or chimeric TNF receptor superfamily member 4 (OX40). In some embodiments, the sequence encoding the human or chimeric OX40 is operably linked to an endogenous regulatory element at the endogenous OX40 gene locus in the at least one chromosome. In some embodiments, the sequence encoding a human or chimeric OX40 comprises a sequence encoding an amino acid sequence that is at least 70%, 75%, 80%, 85%, 90%, 95%, 99%, or 100% identical to human OX40 (NP_003318.1 (SEQ ID NO:28)). In some embodiments, the sequence encoding a human or chimeric OX40 comprises a sequence encoding an amino acid sequence that is at least 70%, 75%, 80%, 85%, 90%, 95%, 99%, or 100% identical to SEQ ID NO: 32. In some embodiments, the sequence encoding a human or chimeric OX40 comprises a sequence encoding an amino acid sequence that corresponds to amino acids 35-197 of SEQ ID NO: 28.

In some embodiments, the animal is a mammal, e.g., a monkey, a rodent or a mouse. In some embodiments, the animal is a C57BL/6 mouse. In some embodiments, the animal does not express endogenous OX40. In some embodiments, the animal has one or more cells expressing human or chimeric OX40. In some embodiments, the animal has one or more cells expressing human or chimeric OX40, and human OX40L can bind to the expressed human or chimeric OX40. In some embodiments, the animal has one or more cells expressing human or chimeric OX40, and endogenous OX40L can bind to the expressed human or chimeric OX40.

In one aspect, the disclosure relates to genetically-modified, non-human animals, wherein the genome of the animals comprises a replacement, at an endogenous OX40 gene locus, of a sequence encoding a region of endogenous OX40 with a sequence encoding a corresponding region of human OX40. In some embodiments, the sequence encoding the corresponding region of human OX40 is operably linked to an endogenous regulatory element at the endogenous OX40 locus, and one or more cells of the animal expresses a chimeric OX40. In some embodiments, the animal does not express endogenous OX40. In some embodiments, the region of endogenous OX40 is the extracellular region of OX40. In some embodiments, the animal has one or more cells expressing a chimeric OX40 having an extracellular region, a transmembrane region, and a cytoplasmic region, wherein the extracellular region comprises a sequence that is at least 50%, 60%, 70%, 80%, 90%, 95%, or 99% identical to the extracellular region of human OX40. In some embodiments, the extracellular region of the chimeric OX40 has a sequence that has at least 10, 20, 30, 40, 50, 60, 70, 80, 90, or 100 contiguous amino acids that are identical to a contiguous sequence present in the extracellular region of human OX40. In some embodiments, the animal is a mouse, and the sequence encoding the region of endogenous OX40 is Exon 1, Exon 2, Exon 3, Exon 4, Exon 5, Exon 6, and/or Exon 7 of the endogenous mouse OX40 gene. In some embodiments, the animal is heterozygous with respect to the replacement at the endogenous OX40 gene locus. In some embodiments, the animal is homozygous with respect to the replacement at the endogenous OX40 gene locus.

In one aspect, the disclosure relates to methods for making a genetically-modified, non-human animal, including: replacing in at least one cell of the animal, at an endogenous OX40 gene locus, a sequence encoding a region of an endogenous OX40 with a sequence encoding a corresponding region of human OX40. In some embodiments, the sequence encoding the corresponding region of human OX40 comprises exon 1, exon 2, exon 3, exon 4, exon 5, exon 6, and/or exon 7 of a human OX40 gene. In some embodiments, the sequence encoding the corresponding region of OX40 comprises exon 2 to exon 4 of a human OX40 gene, and/or a part of exon 1 and/or exon 5 of a human OX40 gene. In some embodiments, the sequence encoding the corresponding region of human OX40 encodes amino acids 35-197 of SEQ ID NO: 28. In some embodiments, the region is located within the extracellular region of OX40. In some embodiments, the animal is a mouse, and the sequence encoding the region of the endogenous OX40 locus is Exon 1 to Exon 5 of mouse OX40 gene.

In one aspect, the disclosure relates to non-human animals comprising at least one cell comprising a nucleotide sequence encoding a chimeric OX40 polypeptide, wherein the chimeric OX40 polypeptide comprises at least 50 contiguous amino acid residues that are identical to the corresponding contiguous amino acid sequence of a human OX40, wherein the animal expresses the chimeric OX40. In some embodiments, the chimeric OX40 polypeptide has at least 50 contiguous amino acid residues that are identical to the corresponding contiguous amino acid sequence of a human OX40 extracellular region. In some embodiments, the chimeric OX40 polypeptide comprises a sequence that is at least 90%, 95%, or 99% identical to amino acids 35-197 of SEQ ID NO: 28. In some embodiments, the nucleotide sequence is operably linked to an endogenous OX40 regulatory element of the animal. In some embodiments, the chimeric OX40 polypeptide comprises an endogenous OX40 transmembrane region and/or an endogenous OX40 cytoplasmic region. In some embodiments, the nucleotide sequence is integrated to an endogenous OX40 gene locus of the animal. In some embodiments, the chimeric OX40 has at least one mouse OX40 activity and/or at least one human OX40 activity.

In one aspect, the disclosure relates to methods of making a genetically-modified mouse cell that expresses a chimeric OX40, the method including: replacing, at an endogenous mouse OX40 gene locus, a nucleotide sequence encoding a region of mouse OX40 with a nucleotide sequence encoding a corresponding region of human OX40, thereby generating a genetically-modified mouse cell that includes a nucleotide sequence that encodes the chimeric OX40, wherein the mouse cell expresses the chimeric OX40. In some embodiments, the chimeric OX40 comprises an extracellular region of mouse OX40 comprising a mouse signal peptide sequence, an extracellular region of human OX40, a transmembrane and/or a cytoplasmic region of a mouse OX40. In some embodiments, the nucleotide sequence encoding the chimeric OX40 is operably linked to an endogenous OX40 regulatory region, e.g., promoter.

In some embodiments, the animals further comprise a sequence encoding an additional human or chimeric protein. In some embodiments, the additional human or chimeric protein is programmed cell death protein 1 (PD-1), CTLA-4, Lymphocyte Activating 3 (LAG-3), T-Cell Immunoglobulin And Mucin Domain-Containing Protein 3 (TIM-3), Programmed Cell Death 1 Ligand 1 (PD-L1), TNF Receptor Superfamily Member 9 (4-1BB), CD27, CD28, CD47, T-Cell Immunoreceptor With Ig And ITIM Domains (TIGIT), CD27, Glucocorticoid-Induced TNFR-Related Protein (GITR), or B And T Lymphocyte Associated (BTLA). In some embodiments, the animal or mouse further comprises a sequence encoding an additional human or chimeric protein. In some embodiments, the additional human or chimeric protein is programmed cell death protein 1 (PD-1), CTLA-4, LAG-3, TIM-3, PD-L1, 4-1BB, CD27, CD28, CD47, TIGIT, CD27, GITR, or BTLA.

In one aspect, the disclosure relates to methods of determining effectiveness of an anti-OX40 antibody for the treatment of cancer, including: administering the anti-OX40 antibody to the animal described herein, wherein the animal has a tumor, and determining the inhibitory effects of the anti-OX40 antibody to the tumor. In some embodiments, the tumor comprises one or more tumor cells that express OX40L. In some embodiments, the tumor comprises one or more cancer cells that are injected into the animal. In some embodiments, determining the inhibitory effects of the anti-OX40 antibody to the tumor involves measuring the tumor volume in the animal. In some embodiments, the tumor cells are melanoma cells, non-small cell lung carcinoma (NSCLC) cells, small cell lung cancer (SCLC) cells, bladder cancer cells, and/or prostate cancer cells (e.g., metastatic hormone-refractory prostate cancer).

In one aspect, the disclosure relates to methods of determining effectiveness of an anti-OX40 antibody and an additional therapeutic agent for the treatment of a tumor, including administering the anti-OX40 antibody and the additional therapeutic agent to the animal described herein, wherein the animal has a tumor, and determining the inhibitory effects on the tumor. In some embodiments, the animal further comprises a sequence encoding a human or chimeric programmed cell death protein 1 (PD-1). In some embodiments, the additional therapeutic agent is an anti-PD-1 antibody. In some embodiments, the tumor comprises one or more tumor cells that express OX40L. In some embodiments, the tumor comprises one or more tumor cells that express PD-L1 or PD-L2. In some embodiments, the tumor is caused by injection of one or more cancer cells into the animal. In some embodiments, determining the inhibitory effects of the treatment involves measuring the tumor volume in the animal. In some embodiments, the tumor comprises melanoma cells, non-small cell lung carcinoma (NSCLC) cells, small cell lung cancer (SCLC) cells, bladder cancer cells, and/or prostate cancer cells (e.g., metastatic hormone-refractory prostate cancer cells).

In one aspect, the disclosure relates to proteins comprising an amino acid sequence, wherein the amino acid sequence is one of the following: (a) an amino acid sequence set forth in SEQ ID NO: 32; (b) an amino acid sequence that is at least 90% identical to SEQ ID NO: 32; (c) an amino acid sequence that is at least 91%, 92%, 93%, 94%, 95%, 96%, 97%, 98%, or 99% identical to SEQ ID NO: 32; (d) an amino acid sequence that is different from the amino acid sequence set forth in SEQ ID NO: 32 by no more than 10, 9, 8, 7, 6, 5, 4, 3, 2 or 1 amino acid; and (e) an amino acid sequence that comprises a substitution, a deletion and/or insertion of one, two, three, four, five or more amino acids to the amino acid sequence set forth in SEQ ID NO: 32. In some embodiments, provided herein are cells comprising the proteins disclosed herein. In some embodiments, provided herein are animals having the proteins disclosed herein.

In one aspect, the disclosure relates to nucleic acids comprising a nucleotide sequence, wherein the nucleotide sequence is one of the following: (a) a sequence that encodes the protein described herein; (b) SEQ ID NO: 30; (c) SEQ ID NO: 31; (d) a sequence that is at least 90% identical to SEQ ID NO: 30 or SEQ ID NO: 31; (e) a sequence that is at least 91%, 92%, 93%, 94%, 95%, 96%, 97%, 98%, or 99% identical to SEQ ID NO: 30; and (f) a sequence that is at least 91%, 92%, 93%, 94%, 95%, 96%, 97%, 98%, or 99% identical to SEQ ID NO: 31. In some embodiments, provided herein are cells comprising the nucleic acids disclosed herein. In some embodiments, provided herein are animals having the nucleic acids disclosed herein.

In one aspect, the disclosure relates to a targeting vector, including a) a DNA fragment homologous to the 5' end of a region to be altered (5' arm), which is selected from the OX40 gene genomic DNAs in the length of 100 to 10,000 nucleotides; b) a desired/donor DNA sequence encoding a donor region; and c) a second DNA fragment homologous to the 3' end of the region to be altered (3' arm), which is selected from the OX40 gene genomic DNAs in the length of 100 to 10,000 nucleotides.

In some embodiments, a) the DNA fragment homologous to the 5' end of a region to be altered (5' arm/receptor) is selected from the nucleotide sequences that have at least 90% homology to the NCBI accession number NC_000070.6; c) the DNA fragment homologous to the 3' end of the region to be altered (3' arm/receptor) is selected from the nucleotide sequences that have at least 90% homology to the NCBI accession number NC_000070.6.

In some embodiments, a) the DNA fragment homologous to the 5' end of a region to be altered (5' arm/receptor) is selected from the nucleotides from the position 156012720 to the position 156013963 of the NCBI accession number NC_000070.6; c) the DNA fragment homologous to the 3' end of the region to be altered (3' arm/receptor) is selected from the nucleotides from the position 156016032 to the position 156017196 of the NCBI accession number NC_000070.6.

In some embodiments, a length of the selected genomic nucleotide sequence is 1.2 kb, 1.5 kb or 1 kb. In some embodiments, the region to be altered is exon 1 of OX40 and exon 5 of OX40 gene.

In some embodiments, the sequence of the 5' arm is shown in SEQ ID NO: 33. In some embodiments, the sequence of the 3' arm is shown in SEQ ID NO: 39.

In some embodiments, the targeting vector further includes a selectable gene marker.

In some embodiments, the target region is derived from human. In some embodiments, the target region is a part or entirety of the nucleotide sequence of a humanized OX40. In some embodiments, the nucleotide sequence is shown as one or more of the first exon, the second exon, the third exon, the fourth exon, the fifth exon, the sixth exon, and the seventh exon of the DNA sequence of the human OX40.

In some embodiments, the nucleotide sequence of the human OX40 encodes the human OX40 protein with the NCBI accession number NP_003318.1 (SEQ ID NO:28). In some embodiments, the target region is shown in SEQ ID NO: 18.

The disclosure also relates to a cell including the targeting vector as described herein.

In another aspect, the disclosure relates to an sgRNA sequence for constructing a humanized animal model, wherein the sgRNA sequence targets the OX40 gene, the sgRNA is unique on the target sequence of the OX40 gene to be altered, and meets the sequence arrangement rule of 5'-NNN (20)-NGG3' or 5'-CCN-N (20)-3'. In some embodiments, the targeting site of the sgRNA in the mouse OX40 gene is located on the exon 1 and/or exon 5 of the mouse OX40 gene.

In another aspect, the disclosure relates to an sgRNA sequence for constructing a humanized animal model, wherein an upstream sequence thereof is shown as SEQ ID NO: 16, and a downstream sequence thereof is shown as SEQ ID NO: 18, and the sgRNA sequence recognizes a 5' targeting site.

The disclosure also relates to an sgRNA sequence for constructing a humanized animal model, wherein an upstream sequence thereof is shown as SEQ ID NO: 17, which is obtained by adding TAGG to the 5' end of SEQ ID NO: 16; a downstream sequence thereof is shown as SEQ ID NO: 19, which is obtained by adding AAAC to the 5' end of SEQ ID NO: 18, and the sgRNA sequence recognizes a 5' targeting site.

The disclosure also relates to an sgRNA sequence for constructing a humanized animal model, wherein an upstream sequence thereof is shown as SEQ ID NO: 20, and a downstream sequence thereof is shown as SEQ ID NO: 22, and the sgRNA sequence recognizes a 3' targeting site.

The disclosure further relates to an sgRNA sequence for constructing a humanized animal model, wherein an upstream sequence thereof is shown as SEQ ID NO: 21, which is obtained by adding TAGG to the 5' end of SEQ ID NO: 20; a downstream sequence thereof is shown as SEQ ID NO: 23, which is obtained by adding AAAC to the 5' end of SEQ ID NO: 22, and the sgRNA sequence recognizes a 3' targeting site.

In one aspect, the disclosure relates to a construct including the sgRNA sequence as described herein.

The disclosure also relates to a cell comprising the construct as described herein.

In another aspect, the disclosure relates to a non-human mammalian cell, comprising the targeting vector as described herein, and one or more in vitro transcripts of the sgRNA construct.

In some embodiments, the cell includes Cas9 mRNA or an in vitro transcript thereof.

In some embodiments, the genes in the cell are heterozygous. In some embodiments, the genes in the cell are homozygous.

In some embodiments, the non-human mammalian cell is a mouse cell. In some embodiments, the cell is a fertilized egg cell. In some embodiments, the cell is a germ cell. In some embodiments, the cell is a blastocyst. In some embodiments, the cell is a lymphocyte (e.g., a B-cell or a T-cell).

In another aspect, the disclosure relates to a method for establishing a OX40 gene humanized animal model. The methods include the steps of (a) providing the cell, and preferably the cell is a fertilized egg cell;

(b) culturing the cell in a liquid culture medium;

(c) transplanting the cultured cell to the fallopian tube or uterus of the recipient female non-human mammal, allowing the cell to develop in the uterus of the female non-human mammal;

(d) identifying the germline transmission in the offspring genetically modified humanized non-human mammal of the pregnant female in step (c).

In some embodiments, the establishment of a humanized animal model of OX40 gene using a gene editing technique is based on CRISPR/Cas9.

In some embodiments, the non-human mammal is mouse. In some embodiments, the mouse is a C57BL/6 mouse. In some embodiments, the non-human mammal in step (c) is a female with false pregnancy.

The disclosure also relates to a method for establishing a genetically-modified non-human animal expressing two human or chimeric (e.g., humanized) genes. The method includes the steps of (a) using the method for establishing a OX40 gene humanized animal model to obtain a OX40 gene genetically modified humanized mouse;

(b) mating the OX40 gene genetically modified humanized mouse obtained in step (a) with another humanized mouse, and then screening to obtain a double humanized mouse model.

In some embodiments, in step (b), the OX40 gene genetically modified humanized mouse obtained in step (a) is mated with a PD-1 humanized mouse to obtain a OX40 and PD-1 double humanized mouse model.

The disclosure also relates to non-human mammal generated through the methods as described herein.

In some embodiments, the genome thereof contains human gene(s).

In some embodiments, the non-human mammal is a rodent. In some embodiments, the non-human mammal is a mouse.

In some embodiments, the non-human mammal expresses a protein encoded by a humanized OX40 gene.

The disclosure also relates to an offspring of the non-human mammal.

In another aspect, the disclosure relates to a tumor bearing non-human mammal model, characterized in that the non-human mammal model is obtained through the method as described herein.

In some embodiments, the non-human mammal is a rodent. In some embodiments, the non-human mammal is a mouse.

The disclosure also relates to a cell or cell line, or a primary cell culture thereof derived from the non-human mammal or an offspring thereof, or the tumor bearing non-human mammal.

The disclosure further relates to the tissue, organ or a culture thereof derived from the non-human mammal or an offspring thereof, or the tumor bearing non-human mammal.

In another aspect, the disclosure relates to a tumor tissue derived from the non-human mammal or an offspring thereof when it bears a tumor, or the tumor bearing non-human mammal.

In one aspect, the disclosure relates to a OX40 amino acid sequence of a humanized mouse, wherein the amino acid sequence is selected from the group consisting of:

a) an amino acid sequence shown in SEQ ID NO: 32;

b) an amino acid sequence having a homology of at least 90% with the amino acid sequence shown in SEQ ID NO: 32;

c) an amino acid sequence encoded by a nucleic acid sequence, wherein the nucleic acid sequence is able to hybridize to a nucleotide sequence encoding the amino acid shown in SEQ ID NO: 32 under a low stringency condition;

d) an amino acid sequence having a homology of at least 90%, 91%, 92%, 93%, 94%, 95%, 96%, 97%, 98%, or at least 99% with the amino acid sequence shown in SEQ ID NO: 32;

e) an amino acid sequence that is different from the amino acid sequence shown in SEQ ID NO: 32 by no more than 10, 9, 8, 7, 6, 5, 4, 3, 2 or no more than 1 amino acid; or f) an amino acid sequence that comprises a substitution, a deletion and/or insertion of one or more amino acids to the amino acid sequence shown in SEQ ID NO: 32.

The disclosure also relates to a OX40 DNA sequence of a humanized mouse, wherein the DNA sequence is selected from the group consisting of:

a) a DNA sequence that encodes the OX40 amino acid sequence of a humanized mouse;

b) a DNA sequence that is shown in SEQ ID NO: 36;

c) a DNA sequence having a CDS encoding sequence as shown in SEQ ID NO: 30;

d) a DNA sequence that is able to hybridize to the nucleotide sequence as shown in SEQ ID NO: 36 or SEQ ID NO: 30 under a low stringency condition;

e) a DNA sequence that has a homology of at least 90% with the nucleotide sequence as shown in SEQ ID NO: 30 or SEQ ID NO: 31;

f) a DNA sequence that encodes an amino acid sequence, wherein the amino acid sequence has a homology of at least 90% with the amino acid sequence shown in SEQ ID NO: 32;

g) a DNA sequence that encodes an amino acid sequence, wherein the amino acid sequence has a homology of at least 90%, 91%, 92%, 93%, 94%, 95%, 96%, 97%, 98%, or at least 99% with the amino acid sequence shown in SEQ ID NO: 32;

h) a DNA sequence that encodes an amino acid sequence, wherein the amino acid sequence is different from the amino acid sequence shown in SEQ ID NO: 32 by no more than 10, 9, 8, 7, 6, 5, 4, 3, 2 or no more than 1 amino acid; and/or i) a DNA sequence that encodes an amino acid sequence, wherein the amino acid sequence comprises a substitution, a deletion and/or insertion of 1, 2, 3, 4, 5, 6, 7, 8, 9, or more amino acids to the amino acid sequence shown in SEQ ID NO: 32.

j) and optimized SEQ ID NO:36.

The disclosure further relates to a OX40 genomic DNA sequence of a humanized mouse, a DNA sequence obtained by a reverse transcription of the mRNA obtained by transcription thereof is consistent with or complementary to the DNA sequence; a construct expressing the amino acid sequence thereof; a cell comprising the construct thereof; a tissue comprising the cell thereof.

The disclosure further relates to the use of the non-human mammal or an offspring thereof, or the tumor bearing non-human mammal, the animal model generated through the method as described herein in the development of a product related to an immunization processes of human cells, the manufacture of a human antibody, or the model system for a research in pharmacology, immunology, microbiology and medicine.

The disclosure also relates to the use of the non-human mammal or an offspring thereof, or the tumor bearing non-human mammal, the animal model generated through the method as described herein in the production and utilization of an animal experimental disease model of an immunization processes involving human cells, the study on a pathogen, or the development of a new diagnostic strategy and/or a therapeutic strategy.

The disclosure further relates to the use of the non-human mammal or an offspring thereof, or the tumor bearing non-human mammal, the animal model generated through the methods as described herein, in the screening, verifying, evaluating or studying the OX40 gene function, human OX40 antibodies, the drugs or efficacies for human OX40 targeting sites, and the drugs for immune-related diseases and antitumor drugs.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIGS. 16A and 16B show that the mice numbered 174-189 are homozygous for OX40 gene. FIGS. 16C and 16D show that the mice numbered 174-189 are homozygous for humanized PD-1 gene. The results of the two groups show that the 16 mice numbered 174-189 are homozygous for both humanized genes.

FIG. 21 shows the alignment between mouse OX40 amino acid sequence (NP_035789.1; SEQ ID NO: 26) and human OX40 amino acid sequence (NP_003318.1; SEQ ID NO: 28).

SEQUENCE LISTING

Figures 1A, 1B:
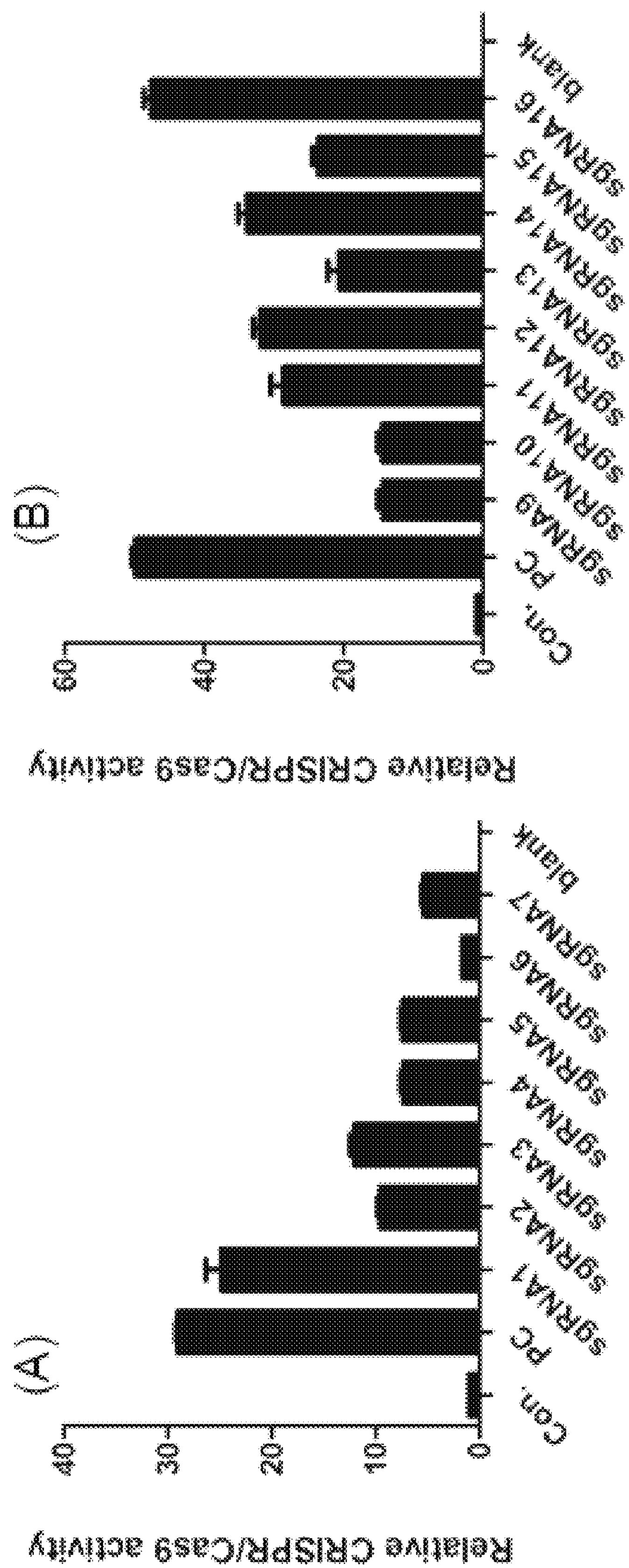
FIG. 1A is a graph showing the 5' terminal target site sgRNA activity test results (sgRNA1-sgRNA7) (Con is a negative control; and PC is a positive control).
FIG. 1B is a graph showing 3' terminal target site sgRNA activity test results (sgRNA9-sgRNA16) (Con is a negative control; and PC is a positive control).

The instant application contains a Sequence Listing which has been submitted electronically in ASCII format and is hereby incorporated by reference in its entirety. Said ASCII copy, created on May 22, 2019, is named UPDATED SEQ.txt and is 31,880 bytes in size.

DETAILED DESCRIPTION

This disclosure relates to transgenic non-human animal with human or chimeric (e.g., humanized) OX40 (TNF Receptor Superfamily Member 4, or TNFRSF4), and methods of use thereof.

In addition to the need for TCR to recognize the MHC-peptide complex as the first signal, the T cell activation process must also be further fully activated by co-stimulatory signals. OX40 is a class of co-stimulatory factors for T cells, which is a member of the tumor necrosis factor receptor (TNFR) superfamily, and a type I transmembrane protein. Under certain conditions, OX40 is able to activate the intracellular PI3K-AKT signal as well as the NFAT signal. These signals have a positive effect on the proliferation and survival of T cells. On the other hand, OX40 can also regulate the function and differentiation direction of T cells.

OX40 is by far the only co-stimulatory molecule that is able to establish peripheral tolerance. It can break the immune tolerance of a tumor and restore immune surveillance. The employment of OX40 as a new target for tumor immunotherapy has already shown certain positive effects. However, since the activation antibody needs to have its epitope for binding and its status to be exactly aligned with the corresponding ligand in order to activate the downstream signaling pathway, which is similar to a key that specifically matches a lock, the development of this type of antibody is very difficult. At present, most of the researches are still in its infancy; and the related drug research and development are still in clinical stage I or II. Therefore, more studies are in urgent need for the OX40 co-stimulatory molecules. Such studies may provide more valuable clues for using these co-stimulatory molecules in tumor immunity and the treatment of other immune diseases. Some of the OX40 antibodies are described e.g., in WO2007/062245A and WO2013/038191A, each of which is incorporated herein by reference in its entirety. It thus can be seen that the OX40 antibody has great application values in the field of tumor immunotherapy. In order to make the clinical trial more effective and minimize treatment failures, the present disclosure provides methods for establishing a humanized OX40 genetically modified animal model.

Experimental animal disease model is an indispensable research tool for studying the etiology, pathogenesis of the disease, as well as the development of prevention and control techniques and therapeutic drugs for the disease. Common experimental animals include mice, rats, guinea pigs, hamsters, rabbits, dogs, monkeys, pigs, fish and so on. However, there are many differences between human and animal genes and protein sequences, and many human proteins cannot bind to the animal's homologous proteins to produce biological activity, leading to that the results of many clinical trials do not match the results obtained from animal experiments. A large number of clinical studies are in urgent need of better animal models. With the continuous development and maturation of genetic engineering technologies, the use of human cells or genes to replace or substitute an animal's endogenous similar cells or genes to establish a biological system or disease model closer to human, and establish the humanized experimental animal models (humanized animal model) has provided an important tool for new clinical approaches or means. In this context, the genetically engineered animal model, that is, the use of genetic manipulation techniques, the use of human normal or mutant genes to replace animal homologous genes, can be used to establish the genetically modified animal models that are closer to human gene systems. The humanized animal models not only have various important applications. Due to the presence of human or humanized genes, the animals can express or express in part of the proteins with human functions, so as to greatly reduce the differences in clinical trials between humans and animals, and provide the possibility of drug screening at animal levels.

Unless otherwise specified, the practice of the methods described herein can take advantage of the techniques of cell biology, cell culture, molecular biology, transgenic biology, microbiology, recombinant DNA and immunology. These techniques are explained in detail in the following literature, for examples: Molecular Cloning A Laboratory Manual, 2nd Ed., ed. By Sambrook, Fritsch and Maniatis (Cold Spring Harbor Laboratory Press: 1989); DNA Cloning, Volumes I and II (D. N. Glovered., 1985); Oligonucleotide Synthesis (M. J. Gaited., 1984); Mullis etal U.S. Pat. No. 4,683,195; Nucleic Acid Hybridization (B. D. Hames& S. J. Higginseds. 1984); Transcription And Translation (B. D. Hames& S. J. Higginseds. 1984); Culture Of Animal Cell (R. I. Freshney, Alan R. Liss, Inc., 1987); Immobilized Cells And Enzymes (IRL Press, 1986); B. Perbal, A Practical Guide To Molecular Cloning (1984), the series, Methods In ENZYMOLOGY (J. Abelson and M. Simon, eds.-in-chief, Academic Press, Inc., New York), specifically, Vols. 154 and 155 (Wu etal. eds.) and Vol. 185, "Gene Expression Technology" (D. Goeddel, ed.); Gene Transfer Vectors For Mammalian Cells (J. H. Miller and M. P. Caloseds., 1987, Cold Spring Harbor Laboratory); Immunochemical Methods In Cell And Molecular Biology (Mayer and Walker, eds., Academic Press, London, 1987); Hand book Of Experimental Immunology, Volumes V (D. M. Weir and C. C. Blackwell, eds., 1986); and Manipulating the Mouse Embryo, (Cold Spring Harbor Laboratory Press, Cold Spring Harbor, N. Y., 1986), each of which is incorporated herein in its entirety by reference.

OX40 (TNF Receptor Superfamily Member 4, or TNFRSF4)

Tumor necrosis factor receptor superfamily, member 4 (TNFRSF4), also known as CD134 and OX40, is a member of the TNFR-superfamily of receptors which is not constitutively expressed on resting naïve T cells. OX40 is a secondary co-stimulatory immune checkpoint molecule, expressed after 24 to 72 hours following activation; its ligand, OX40L, is also not expressed on resting antigen presenting cells, but is following their activation. Expression of OX40 is dependent on full activation of the T cell; without CD28, expression of OX40 is delayed and of fourfold lower levels.

In human genomes, OX40 gene locus has 7 exons, exon 1, exon 2, exon 3, exon 4, exon 5, exon 6, and exon 7 (FIG.

3). The OX40 protein also has an extracellular region, a transmembrane region, and a cytoplasmic region, and the signal peptide is located at the extracellular region of OX40. The nucleotide sequence for human OX40 mRNA is NM_003327.3 (SEQ ID NO: 27), the amino acid sequence for human OX40 is NP_003318.1 (SEQ ID NO:28). The location for each exon and each region in human OX40 nucleotide sequence and amino acid sequence is listed below:

TABLE 1

| Human OX40 (approximate location) | NM_003327.3 (SEQ ID NO: 27) | NP_003318.1 (SEQ ID NO: 28) |
|---|---|---|
| Exon 1 | 1-186 | 1-48 |
| Exon 2 | 187-309 | 49-89 |
| Exon 3 | 310-411 | 90-123 |
| Exon 4 | 412-478 | 124-146 |
| Exon 5 | 479-675 | 147-211 |
| Exon 6 | 676-804 | 212-254 |
| Exon 7 | 805-1104 | 255-277 |
| Signal peptide | 42-125 | 1-28 |
| Extracellular region (excluding signal peptide region) | 126-683 | 29-214 |
| Transmembrane region | 684-746 | 215-235 |
| Cytoplasmic region | 747-872 | 236-277 |
| Donor region | 144-632 with mutations at positions 146, 149, and 152 | 35-197 |

Figure 3:
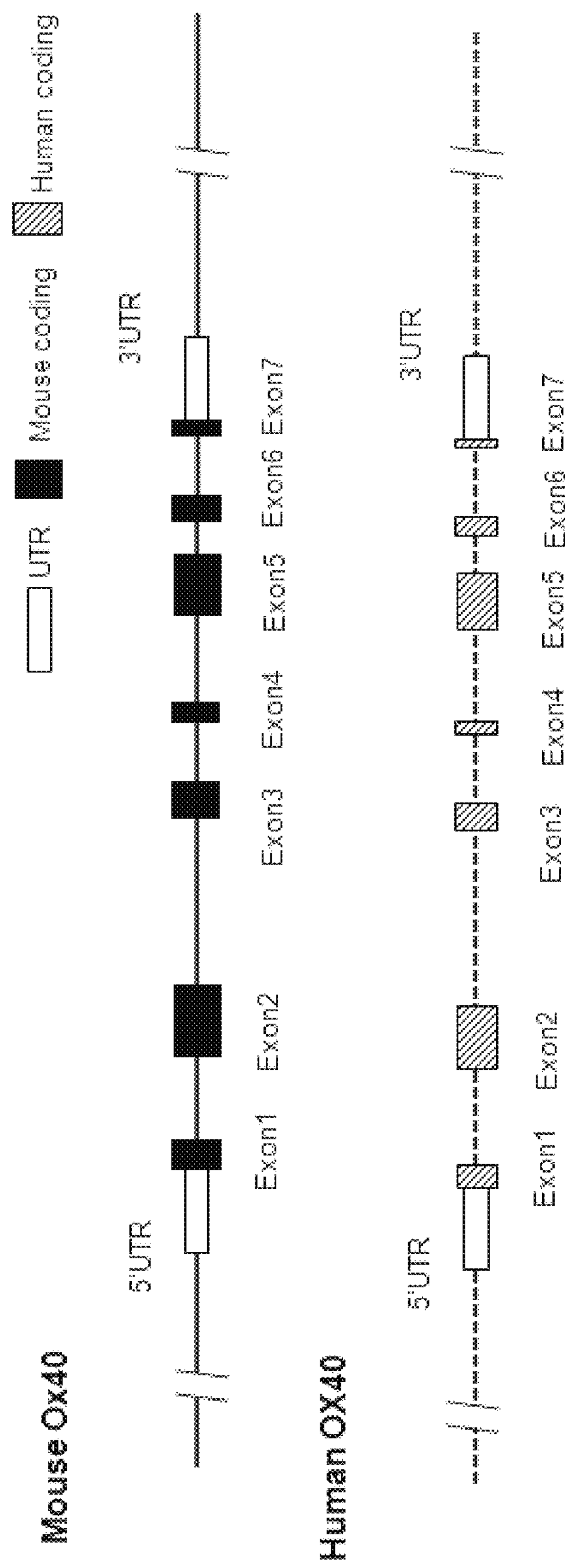
FIG. 3 is a schematic diagram showing comparison of human and mouse OX40 genes.

Similarly, in mice, OX40 gene locus has 7 exons, exon 1, exon 2, exon 3, exon 4, exon 5, exon 6, and exon 7 (FIG. 3). The OX40 protein also has an extracellular region, a transmembrane region, and a cytoplasmic region, and the signal peptide is located at the extracellular region of OX40. The nucleotide sequence for mouse OX40 cDNA is NM_011659.2 (SEQ ID NO: 25), the amino acid sequence for mouse OX40 is NP_035789.1 (SEQ ID NO: 26). The location for each exon and each region in the mouse OX40 nucleotide sequence and amino acid sequence is listed below:

TABLE 2

| Mouse OX40 (approximate location) | NM_011659.2 (SEQ ID NO: 25) | NP_035789.1 (SEQ ID NO: 26) |
|---|---|---|
| Exon 1 | 1-312 | 1-44 |
| Exon 2 | 313-435 | 45-85 |
| Exon 3 | 436-543 | 86-121 |
| Exon 4 | 544-610 | 122-144 |
| Exon 5 | 611-807 | 145-209 |
| Exon 6 | 808-927 | 210-249 |
| Exon 7 | 928-1155 | 250-272 |
| Signal peptide | 180-236 | 1-19 |
| Extracellular region (excluding signal peptide region) | 237-812 | 20-211 |
| Transmembrane region | 813-887 | 212-236 |
| Cytoplasmic region | 888-995 | 237-272 |
| Replaced region | 270-764 | 31-195 |

The mouse OX40 gene (Gene ID: 22163) is located in Chromosome 4 of the mouse genome, which is located from 156013595 to 156016613 of NC_000070.6 (GRCm38.p4 (GCF_000001635.24)). The 5'-UTR is from 156013843 to 156013873, exon 1 is from 156013874 to 156014006, the first intron is from 156014007 to 156014227, exon 2 is from 156014228 to 156014350, the second intron is from 156014351 to 156014901, exon 3 is from 156014902 to 156015009, the third intron is from 156015010 to 156015385, exon 4 is from 156015386 to 156015452, the fourth intron is from 156015453 to 156015877, exon 5 is from 156015878 to 156016074, the fifth intron is from 156016075 to 156016153, exon 6 is from 156016154 to 156016273, the sixth intron is from 156016274 to 156016361, exon 7 is from 156016362 to 156016432, the 3'-UTR is from 156016433 to 156016612, base on transcript NM_011659.2. All relevant information for mouse OX40 locus can be found in the NCBI website with Gene ID: 22163, which is incorporated by reference herein in its entirety.

FIG. 21 shows the alignment between mouse OX40 amino acid sequence (NP_035789.1; SEQ ID NO: 26) and human OX40 amino acid sequence (NP_003318.1 (SEQ ID NO:28). Thus, the corresponding amino acid residue or region between human and mouse OX40 can also be found in FIG. 21.

OX40 genes, proteins, and locus of the other species are also known in the art. For example, the gene ID for OX40 in Rattusnorvegicusis 25572, the gene ID for OX40 in Macacamulatta (Rhesus monkey) is 699674, the gene ID for OX40 in Susscrofa (pig) is 100524628. The relevant information for these genes (e.g., intron sequences, exon sequences, amino acid residues of these proteins) can be found, e.g., in NCBI database.

The present disclosure provides human or chimeric (e.g., humanized) OX40 nucleotide sequence and/or amino acid sequences. In some embodiments, the entire sequence of mouse exon 1, exon 2, exon 3, exon 4, exon 5, exon 6, exon 7, signal peptide, extracellular region, transmembrane region, and/or cytoplasmic region are replaced by the corresponding human sequence. In some embodiments, a "region" or "portion" of mouse exon 1, exon 2, exon 3, exon 4, exon 5, exon 6, exon 7, signal peptide, extracellular region, transmembrane region, and/or cytoplasmic region are replaced by the corresponding human sequence. The term "region" or "portion" can refer to at least 1, 2, 3, 4, 5, 6, 7, 8, 9, 10, 20, 30, 40, 50, 60, 70, 80, 90, 100, 110, 120, 130, 150, 200, 250, 300, 350, or 400 nucleotides, or at least 1, 2, 3, 4, 5, 6, 7, 8, 9, 10, 20, 30, 40, 50, 60, 70, 80, 90, 100, 110, 120, 130, or 150 amino acid residues. In some embodiments, the "region" or "portion" can be at least 50%, 55%, 60%, 65%, 70%, 75%, 80%, 85%, 90%, 95%, or 99% identical to exon 1, exon 2, exon 3, exon 4, exon 5, exon 6, exon 7, signal peptide, extracellular region, transmembrane region, or cytoplasmic region. In some embodiments, a region, a portion, or the entire sequence of mouse exon 1, exon 2, exon 3, exon 4, and/or exon 5 (e.g., exon 1 to exon 5) are replaced by the human exon1, exon 2, exon 3, exon 4, and/or exon 5 (e.g., exon 1 to exon 5) sequence.

In some embodiments, the present disclosure also provides a chimeric (e.g., humanized) OX40 nucleotide sequence and/or amino acid sequences, wherein in some embodiments, at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% of the sequence are identical to or derived from mouse OX40 mRNA sequence (e.g., SEQ ID NO: 25), or mouse OX40 amino acid sequence (e.g., SEQ ID NO: 26); and in some embodiments, at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% of the sequence are identical to or derived from human OX40 mRNA sequence (e.g., SEQ ID NO: 27), or human OX40 amino acid sequence (e.g., SEQ ID NO: 28).

In some embodiments, the sequence encoding amino acids 31-195 of mouse OX40 (SEQ ID NO: 26) is replaced. In some embodiments, the sequence is replaced by a sequence encoding a corresponding region of human OX40 (e.g., amino acids 35-197 of human OX40 (SEQ ID NO: 28)).

In some embodiments, the nucleic acids as described herein are operably linked to a promotor or regulatory element, e.g., an endogenous mouse OX40 promotor, an inducible promoter, an enhancer, and/or mouse or human regulatory elements.

In some embodiments, the nucleic acid sequence has at least a portion (e.g., at least 1, 2, 3, 4, 5, 6, 7, 8, 9, 10, 11, 12, 13, 14, 15, 20, 30, 40, 50, 60, 70, 80, 90, or 100 nucleotides, e.g., contiguous or non-contiguous nucleotides) that are different from a portion of or the entire mouse OX40 nucleotide sequence (e.g., NM_011659.2 (SEQ ID NO: 25)).

In some embodiments, the nucleic acid sequence has at least a portion (e.g., at least 1, 2, 3, 4, 5, 6, 7, 8, 9, 10, 11, 12, 13, 14, 15, 20, 30, 40, 50, 60, 70, 80, 90, or 100 nucleotides, e.g., contiguous or non-contiguous nucleotides) that is the same as a portion of or the entire mouse OX40 nucleotide sequence (e.g., NM_011659.2 (SEQ ID NO: 25)).

In some embodiments, the nucleic acid sequence has at least a portion (e.g., at least 1, 2, 3, 4, 5, 6, 7, 8, 9, 10, 11, 12, 13, 14, 15, 20, 30, 40, 50, 60, 70, 80, 90, or 100 nucleotides, e.g., contiguous or non-contiguous nucleotides) that is different from a portion of or the entire human OX40 nucleotide sequence (e.g., NM_003327.3 (SEQ ID NO: 27)).

In some embodiments, the nucleic acid sequence has at least a portion (e.g., at least 1, 2, 3, 4, 5, 6, 7, 8, 9, 10, 11, 12, 13, 14, 15, 20, 30, 40, 50, 60, 70, 80, 90, or 100 nucleotides, e.g., contiguous or non-contiguous nucleotides) that is the same as a portion of or the entire human OX40 nucleotide sequence (e.g., NM_003327.3 (SEQ ID NO: 27)).

In some embodiments, the amino acid sequence has at least a portion (e.g., at least 1, 2, 3, 4, 5, 6, 7, 8, 9, 10, 11, 12, 13, 14, 15, 20, 30, 40, 50, 60, 70, 80, 90, or 100 amino acid residues, e.g., contiguous or non-contiguous amino acid residues) that is different from a portion of or the entire mouse OX40 amino acid sequence (e.g., NP_035789.1 (SEQ ID NO: 26)).

In some embodiments, the amino acid sequence has at least a portion (e.g., at least 1, 2, 3, 4, 5, 6, 7, 8, 9, 10, 11, 12, 13, 14, 15, 20, 30, 40, 50, 60, 70, 80, 90, or 100 amino acid residues, e.g., contiguous or non-contiguous amino acid residues) that is the same as a portion of or the entire mouse OX40 amino acid sequence (e.g., NP_035789.1 (SEQ ID NO: 26)).

In some embodiments, the amino acid sequence has at least a portion (e.g., at least 1, 2, 3, 4, 5, 6, 7, 8, 9, 10, 11, 12, 13, 14, 15, 20, 30, 40, 50, 60, 70, 80, 90, or 100 amino acid residues, e.g., contiguous or non-contiguous amino acid residues) that is different from a portion of or the entire human OX40 amino acid sequence (e.g., NP_003318.1 (SEQ ID NO:28)).

In some embodiments, the amino acid sequence has at least a portion (e.g., at least 1, 2, 3, 4, 5, 6, 7, 8, 9, 10, 11, 12, 13, 14, 15, 20, 30, 40, 50, 60, 70, 80, 90, or 100 amino acid residues, e.g., contiguous or non-contiguous amino acid residues) that is the same as a portion of or the entire human OX40 amino acid sequence (e.g., NP_003318.1 (SEQ ID NO:28)).

The present disclosure also provides a humanized OX40 mouse amino acid sequence, wherein the amino acid sequence is selected from the group consisting of:

a) an amino acid sequence shown in SEQ ID NO: 32;

b) an amino acid sequence having a homology of at least 90% with or at least 90% identical to the amino acid sequence shown in SEQ ID NO: 32;

c) an amino acid sequence encoded by a nucleic acid sequence, wherein the nucleic acid sequence is able to hybridize to a nucleotide sequence encoding the amino acid shown in SEQ ID NO: 32 under a low stringency condition;

d) an amino acid sequence having a homology of at least 90%, 91%, 92%, 93%, 94%, 95%, 96%, 97%, 98%, or 99%, or at least 90%, 91%, 92%, 93%, 94%, 95%, 96%, 97%, 98%, or 99% identical to the amino acid sequence shown in SEQ ID NO: 32;

e) an amino acid sequence that is different from the amino acid sequence shown in SEQ ID NO: 32 by no more than 10, 9, 8, 7, 6, 5, 4, 3, 2 or no more than 1 amino acid; or f) an amino acid sequence that comprises a substitution, a deletion and/or insertion of one or more amino acids to the amino acid sequence shown in SEQ ID NO: 32.

The present disclosure also relates to a OX40 DNA sequence, wherein the DNA sequence can be selected from the group consisting of:

a) a DNA sequence as shown in SEQ ID NO: 30, or a DNA sequence encoding a homologous OX40 amino acid sequence of a humanized mouse;

b) a DNA sequence that is shown in SEQ ID NO: 31;

c) a DNA sequence that is able to hybridize to the nucleotide sequence as shown in SEQ ID NO: 30 or SEQ ID NO: 31 under a low stringency condition;

d) a DNA sequence that has a homology of at least 90% or at least 90% identical to the nucleotide sequence as shown in SEQ ID NO: 30 or SEQ ID NO: 31;

e) a DNA sequence that encodes an amino acid sequence, wherein the amino acid sequence has a homology of at least 90% with or at least 90% identical to the amino acid sequence shown in SEQ ID NO: 32;

f) a DNA sequence that encodes an amino acid sequence, wherein the amino acid sequence has a homology of at least 90%, 91%, 92%, 93%, 94%, 95%, 96%, 97%, 98%, or 99% with, or at least 90%, 91%, 92%, 93%, 94%, 95%, 96%, 97%, 98%, or 99% identical to the amino acid sequence shown in SEQ ID NO: 32;

g) a DNA sequence that encodes an amino acid sequence, wherein the amino acid sequence is different from the amino acid sequence shown in SEQ ID NO: 32 by no more than 10, 9, 8, 7, 6, 5, 4, 3, 2 or no more than 1 amino acid; and/or h) a DNA sequence that encodes an amino acid sequence, wherein the amino acid sequence comprises a substitution, a deletion and/or insertion of one or more amino acids to the amino acid sequence shown in SEQ ID NO: 32.

The present disclosure further relates to a OX40 genomic DNA sequence of a humanized mouse. The DNA sequence is obtained by a reverse transcription of the mRNA obtained by transcription thereof is consistent with or complementary to the DNA sequence homologous to the sequence shown in SEQ ID NO: 31 or SEQ ID NO: 30.

The disclosure also provides an amino acid sequence that has a homology of at least 90% with, or at least 90% identical to the sequence shown in SEQ ID NO: 32, and has protein activity. In some embodiments, the homology with the sequence shown in SEQ ID NO: 32 is at least about 90%, 91%, 92%, 93%, 94%, 95%, 96%, 97%, 98%, or at least 99%. In some embodiments, the foregoing homology is at least bout 50%, 51%, 52%, 53%, 54%, 55%, 56%, 57%, 58%, or at least about 59%.

In some embodiments, the percentage identity with the sequence shown in SEQ ID NO: 32 is at least about 90%, 91%, 92%, 93%, 94%, 95%, 96%, 97%, 98%, or at least 99%. In some embodiments, the foregoing percentage identity is at least bout 50%, 51%, 52%, 53%, 54%, 55%, 56%, 57%, 58%, or at least about 59%.

In some embodiments, the amino acid sequence (i) comprises an amino acid sequence; or (ii) consists of an amino acid sequence, wherein the amino acid sequence comprises any one of the sequences mentioned above.

The disclosure also provides a nucleotide sequence that has a homology of at least 90%, or at least 90% identical to the sequence shown in SEQ ID NO: 31, and encodes a polypeptide that has protein activity. In some embodiments, the homology with the sequence shown in SEQ ID NO: 31 is at least about 90%, 91%, 92%, 93%, 94%, 95%, 96%, 97%, 98%, or at least 99%. In some embodiments, the foregoing homology is at least bout 50%, 51%, 52%, 53%, 54%, 55%, 56%, 57%, 58%, or at least about 59%.

In some embodiments, the percentage identity with the sequence shown in SEQ ID NO: 31 is at least about 90%, 91%, 92%, 93%, 94%, 95%, 96%, 97%, 98%, or at least 99%. In some embodiments, the foregoing percentage identity is at least about 50%, 51%, 52%, 53%, 54%, 55%, 56%, 57%, 58%, or at least about 59%.

The disclosure also provides a nucleic acid sequence that is at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% identical to any nucleotide sequence as described herein, and an amino acid sequence that is at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% identical to any amino acid sequence as described herein. In some embodiments, the disclosure relates to nucleotide sequences encoding any peptides that are described herein, or any amino acid sequences that are encoded by any nucleotide sequences as described herein. In some embodiments, the nucleic acid sequence is less than 10, 20, 30, 40, 50, 60, 70, 80, 90, 100, 110, 120, 130, 150, 200, 250, 300, 350, 400, or 500 nucleotides. In some embodiments, the amino acid sequence is less than 5, 6, 7, 8, 9, 10, 20, 30, 40, 50, 60, 70, 80, 90, 100, 110, 120, 130, or 150 amino acid residues.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). The length of a reference sequence aligned for comparison purposes is at least 80% of the length of the reference sequence, and in some embodiments is at least 90%, 95%, or 100%. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences, taking into account the number of gaps, and the length of each gap, which need to be introduced for optimal alignment of the two sequences. For purposes of the present disclosure, the comparison of sequences and determination of percent identity between two sequences can be accomplished using a Blossum 62 scoring matrix with a gap penalty of 12, a gap extend penalty of 4, and a frameshift gap penalty of 5.

The term "percent homology" is often used to mean "sequence similarity." The percentage of identical residues (percent identity) and the percentage of residues conserved with similar physicochemical properties (percent similarity), e.g. leucine and isoleucine, are both used to "quantify the homology". Residues conserved with similar physicochemical properties are well known in the art. The percent homology, in many cases, is higher than the percent identity.

Cells, tissues, and animals (e.g., mouse) are also provided that comprise the nucleotide sequences as described herein, as well as cells, tissues, and animals (e.g., mouse) that express human or humanized OX40 from an endogenous non-human OX40 locus.

Genetically Modified Animals

As used herein, the term "genetically-modified non-human animal" refers to a non-human animal having exogenous DNA in at least one chromosome of the animal's genome. In some embodiments, at least one or more cells, e.g., at least 1%, 2%, 3%, 4%, 5%, 10%, 20%, 30%, 40%, 50% of cells of the genetically-modified non-human animal have the exogenous DNA in its genome. The cell having exogenous DNA can be various kinds of cells, e.g., an endogenous cell, a somatic cell, an immune cell, a T cell, a B cell, a germ cell, a blastocyst, or an endogenous tumor cell. In some embodiments, genetically-modified non-human animals are provided that comprise a modified endogenous OX40 locus that comprises an exogenous sequence (e.g., a human sequence), e.g., a replacement of one or more non-human sequences with one or more human sequences. The animals are generally able to pass the modification to progeny, i.e., through germline transmission.

As used herein, the term "chimeric gene" or "chimeric nucleic acid" refers to a gene or a nucleic acid, wherein two or more portions of the gene or the nucleic acid are from different species, or at least one of the sequences of the gene or the nucleic acid does not correspond to the wildtype nucleic acid in the animal. In some embodiment, the chimeric gene or chimeric nucleic acid has at least one portion of the sequence that is derived from two or more different sources, e.g., sequences encoding different proteins or sequences encoding the same (or homologous) protein of two or more different species. In some embodiments, the chimeric gene or the chimeric nucleic acid is a humanized gene or humanized nucleic acid.

As used herein, the term "chimeric protein" or "chimeric polypeptide" refers to a protein or a polypeptide, wherein two or more portions of the protein or the polypeptide are from different species, or at least one of the sequences of the protein or the polypeptide does not correspond to wildtype amino acid sequence in the animal. In some embodiments, the chimeric protein or the chimeric polypeptide has at least one portion of the sequence that is derived from two or more different sources, e.g., same (or homologous) proteins of different species. In some embodiments, the chimeric protein or the chimeric polypeptide is a humanized protein or a humanized polypeptide.

In some embodiments, the chimeric gene or the chimeric nucleic acid is a humanized OX40 gene or a humanized OX40 nucleic acid. In some embodiments, at least one or more portions of the gene or the nucleic acid is from the human OX40 gene, at least one or more portions of the gene or the nucleic acid is from a non-human OX40 gene. In some embodiments, the gene or the nucleic acid comprises a sequence that encodes a OX40 protein. The encoded OX40 protein is functional or has at least one activity of the human OX40 protein or the non-human OX40 protein, e.g., binding to human or non-human OX40L and/or TRAF2, regulating immune response, and/or preventing T cells from dying, and increasing cytokine production when bound to OX40L.

In some embodiments, the chimeric protein or the chimeric polypeptide is a humanized OX40 protein or a humanized OX40 polypeptide. In some embodiments, at least one or more portions of the amino acid sequence of the protein or the polypeptide is from a human OX40 protein, and at least one or more portions of the amino acid sequence of the protein or the polypeptide is from a non-human OX40 protein. The humanized OX40 protein or the humanized OX40 polypeptide is functional or has at least one activity of the human OX40 protein or the non-human OX40 protein The genetically modified non-human animal can be various animals, e.g., a mouse, rat, rabbit, pig, bovine (e.g., cow, bull, buffalo), deer, sheep, goat, chicken, cat, dog, ferret, primate (e.g., marmoset, rhesus monkey). For the non-human animals where suitable genetically modifiable ES cells are not readily available, other methods are employed to make a non-human animal comprising the genetic modification. Such methods include, e.g., modifying a non-ES cell genome (e.g., a fibroblast or an induced pluripotent cell) and employing nuclear transfer to transfer the modified genome to a suitable cell, e.g., an oocyte, and gestating the modified cell (e.g., the modified oocyte) in a non-human animal under suitable conditions to form an embryo. These methods are known in the art, and are described, e.g., in A. Nagy, et al., "Manipulating the Mouse Embryo: A Laboratory Manual (Third Edition)," Cold Spring Harbor Laboratory Press, 2003, which is incorporated by reference herein in its entirety.

In one aspect, the animal is a mammal, e.g., of the superfamily Dipodoidea or Muroidea. In some embodiments, the genetically modified animal is a rodent. The rodent can be selected from a mouse, a rat, and a hamster. In some embodiment, the rodent is selected from the superfamily Muroidea. In some embodiments, the genetically modified animal is from a family selected from Calomyscidae (e.g., mouse-like hamsters), Cricetidae (e.g., hamster, New World rats and mice, voles), Muridae (true mice and rats, gerbils, spiny mice, crested rats), Nesomyidae (climbing mice, rock mice, with-tailed rats, *Malagasy* rats and mice), Platacanthomyidae (e.g., spiny dormice), and Spalacidae (e.g., mole rates, bamboo rats, and zokors). In some embodiments, the genetically modified rodent is selected from a true mouse or rat (family Muridae), a gerbil, a spiny mouse, and a crested rat. In one embodiment, the non-human animal is a mouse.

In some embodiments, the animal is a mouse of a C57BL strain selected from C57BL/A, C57BL/An, C57BL/GrFa, C57BL/KaLwN, C57BL/6, C57BL/6J, C57BL/6ByJ, C57BL/6NJ, C57BL/10, C57BL/10ScSn, C57BL/10Cr, and C57BL/Ola. In some embodiments, the mouse is a 129 strain selected from the group consisting of a strain that is 129P1, 129P2, 129P3, 129X1, 129S1 (e.g., 129S1/SV, 129S1/SvIm), 129S2, 129S4, 129S5, 129S9/SvEvH, 129S6 (129/SvEvTac), 129S7, 129S8, 129T1, 129T2. These mice are described, e.g., in Festing et al., Revised nomenclature for strain 129 mice, Mammalian Genome 10:836 (1999); Auerbach et al., Establishment and Chimera Analysis of 129/SvEv- and C57BL/6-Derived Mouse Embryonic Stem Cell Lines (2000), which is incorporated by reference in its entirety. In some embodiments, the genetically modified mouse is a mix of the 129 strain and the C57BL/6 strain. In some embodiments, the mouse is a mix of the 129 strains, or a mix of the BL/6 strains. In some embodiment, the mouse is a BALB strain, e.g., BALB/c strain. In some embodiments, the mouse is a mix of a BALB strain and another strain. In some embodiments, the mouse is from a hybrid line (e.g., 50% BALB/c-50% 12954/Sv; or 50% C57BL/6-50% 129).

In some embodiments, the animal is a rat. The rat can be selected from a Wistar rat, an LEA strain, a Sprague Dawley strain, a Fischer strain, F344, F6, and Dark Agouti. In some embodiments, the rat strain is a mix of two or more strains selected from the group consisting of Wistar, LEA, Sprague Dawley, Fischer, F344, F6, and Dark Agouti.

The animal can have one or more other genetic modifications, and/or other modifications, that are suitable for the particular purpose for which the humanized OX40 animal is made. For example, suitable mice for maintaining a xenograft (e.g., a human cancer or tumor), can have one or more modifications that compromise, inactivate, or destroy the immune system of the non-human animal in whole or in part. Compromise, inactivation, or destruction of the immune system of the non-human animal can include, for example, destruction of hematopoietic cells and/or immune cells by chemical means (e.g., administering a toxin), physical means (e.g., irradiating the animal), and/or genetic modification (e.g., knocking out one or more genes). Non-limiting examples of such mice include, e.g., NOD mice, SCID mice, NON/SCID mice, IL2Rγ knockout mice, NOD/SCID/γcnull mice (Ito, M. et al., NOD/SCID/γcnull mouse: an excellent recipient mouse model for engraftment of human cells, Blood 100(9):3175-3182, 2002), nude mice, and Rag1 and/or Rag2 knockout mice. These mice can optionally be irradiated, or otherwise treated to destroy one or more immune cell type. Thus, in various embodiments, a genetically modified mouse is provided that can include a humanization of at least a portion of an endogenous non-human OX40 locus, and further comprises a modification that compromises, inactivates, or destroys the immune system (or one or more cell types of the immune system) of the non-human animal in whole or in part. In some embodiments, modification is, e.g., selected from the group consisting of a modification that results in NOD mice, SCID mice, NOD/SCID mice, IL-2Rγ knockout mice, NOD/SCID/γc null mice, nude mice, Rag1 and/or Rag2 knockout mice, and a combination thereof. These genetically modified animals are described, e.g., in US20150106961, which is incorporated by reference in its entirety. In some embodiments, the mouse can include a replacement of all or part of mature OX40 coding sequence with human mature OX40 coding sequence.

Genetically modified non-human animals that comprise a modification of an endogenous non-human OX40 locus. In some embodiments, the modification can comprise a human nucleic acid sequence encoding at least a portion of a mature OX40 protein (e.g., at least 10%, 20%, 30%, 40%, 50%, 60%, 70%, 80%, 90%, 95%, 96%, 97%, 98%, or 99% identical to the mature OX40 protein sequence). Although genetically modified cells are also provided that can comprise the modifications described herein (e.g., ES cells, somatic cells), in many embodiments, the genetically modified non-human animals comprise the modification of the endogenous OX40 locus in the germline of the animal.

Genetically modified animals can express a human OX40 and/or a chimeric (e.g., humanized) OX40 from endogenous mouse loci, wherein the endogenous mouse OX40 gene has been replaced with a human OX40 gene and/or a nucleotide sequence that encodes a region of human OX40 sequence or an amino acid sequence that is at least 10%, 20%, 30%, 40%, 50%, 60%, 70&, 80%, 90%, 95%, 96%, 97%, 98%, or 99% identical to the human OX40 sequence. In various embodiments, an endogenous non-human OX40 locus is modified in whole or in part to comprise human nucleic acid sequence encoding at least one protein-coding sequence of a mature OX40 protein.

In some embodiments, the genetically modified mice express the human OX40 and/or chimeric OX40 (e.g., humanized OX40) from endogenous loci that are under control of mouse promoters and/or mouse regulatory elements. The replacement(s) at the endogenous mouse loci provide non-human animals that express human OX40 or chimeric OX40 (e.g., humanized OX40) in appropriate cell types and in a manner that does not result in the potential pathologies observed in some other transgenic mice known in the art. The human OX40 or the chimeric OX40 (e.g., humanized OX40) expressed in animal can maintain one or more functions of the wildtype mouse or human OX40 in the animal. For example, human or non-human CD80 and/or CD86 can bind to the expressed OX40 and downregulate immune response, e.g., downregulate immune response by at least 10%, 20%, 30%, 40%, or 50%. Furthermore, in some embodiments, the animal does not express endogenous OX40. As used herein, the term "endogenous OX40" refers to OX40 protein that is expressed from an endogenous OX40 nucleotide sequence of the genetically modified non-human animal (e.g., mouse) before the genetic modification.

The genome of the animal can comprise a sequence encoding an amino acid sequence that is at least 70%, 75%, 80%, 85%, 90%, 95%, 99%, or 100% identical to human OX40 (NP_003318.1) (SEQ ID NO: 28). In some embodiments, the genome comprises a sequence encoding an amino acid sequence that is at least 70%, 75%, 80%, 85%, 90%, 95%, 99%, or 100% identical to SEQ ID NO: 32.

The genome of the genetically modified animal can comprise a replacement at an endogenous OX40 gene locus of a sequence encoding a region of endogenous OX40 with a sequence encoding a corresponding region of human OX40. In some embodiments, the sequence that is replaced is any sequence within the endogenous OX40 gene locus, e.g., exon 1, exon 2, exon 3, exon 4, exon 5, exon 6, exon 7, 5'-UTR, 3'UTR, the first intron, the second intron, and the third intron, the fourth intron, the fifth intron, the sixth intron etc. In some embodiments, the sequence that is replaced is within the regulatory region of the endogenous OX40 gene. In some embodiments, the sequence that is replaced is exon 1, exon 2, exon 3, exon 4, and/or exon 5 of an endogenous mouse OX40 gene locus.

The genetically modified animal can have one or more cells expressing a human or chimeric OX40 (e.g., humanized OX40) having an extracellular region and a cytoplasmic region, wherein the extracellular region comprises a sequence that is at least 50%, 60%, 70%, 80%, 90%, 95%, 99% identical to the extracellular region of human OX40. In some embodiments, the extracellular region of the humanized OX40 has a sequence that has at least 10, 20, 30, 40, 50, 60, 70, 80, 90, or 100 amino acids (e.g., contiguously or non-contiguously) that are identical to human OX40. Because human OX40 and non-human OX40 (e.g., mouse OX40) sequences, in many cases, are different, antibodies that bind to human OX40 will not necessarily have the same binding affinity with mouse OX40 or have the same effects to mouse OX40. Therefore, the genetically modified animal having a human or a humanized extracellular region can be used to better evaluate the effects of anti-human OX40 antibodies in an animal model. In some embodiments, the genome of the genetically modified animal comprises a sequence encoding an amino acid sequence that corresponds to part or the entire sequence of exon 1, exon 2, exon 3, exon 4, and/or exon 5 of human OX40, part or the entire sequence of extracellular region of human OX40 (with or without signal peptide), or part or the entire sequence of amino acids 35-197 of SEQ ID NO: 28.

In some embodiments, the non-human animal can have, at an endogenous OX40 gene locus, a nucleotide sequence encoding a chimeric human/non-human OX40 polypeptide, wherein a human portion of the chimeric human/non-human OX40 polypeptide comprises a portion of human OX40 extracellular domain, and wherein the animal expresses a functional OX40 on a surface of a cell of the animal. The human portion of the chimeric human/non-human OX40 polypeptide can comprise a portion of exon 1, exon 2, exon 3, exon 4, exon 5 of human OX40. In some embodiments, the human portion of the chimeric human/non-human OX40 polypeptide can comprise a sequence that is at least 80%, 85%, 90%, 95%, or 99% identical to amino acids 35-197 of SEQ ID NO: 28.

In some embodiments, the non-human portion of the chimeric human/non-human OX40 polypeptide comprises transmembrane and/or cytoplasmic regions of an endogenous non-human OX40 polypeptide. There may be several advantages that are associated with the transmembrane and/or cytoplasmic regions of an endogenous non-human OX40 polypeptide. For example, once OX40L binds to OX40, they can properly transmit extracellular signals into the cells and regulate the downstream pathway. The binding can prevent T cells from dying and increase cytokine production. A human or humanized transmembrane and/or cytoplasmic regions may not function properly in non-human animal cells. In some embodiments, a few extracellular amino acids that are close to the transmembrane region of OX40 are also derived from endogenous sequence.

Furthermore, the genetically modified animal can be heterozygous with respect to the replacement at the endogenous OX40 locus, or homozygous with respect to the replacement at the endogenous OX40 locus.

In some embodiments, the humanized OX40 locus lacks a human OX40 5'-UTR. In some embodiment, the humanized OX40 locus comprises a rodent (e.g., mouse) 5'-UTR. In some embodiments, the humanization comprises a human 3'-UTR. In appropriate cases, it may be reasonable to presume that the mouse and human OX40 genes appear to be similarly regulated based on the similarity of their 5'-flanking sequence. As shown in the present disclosure, humanized OX40 mice that comprise a replacement at an endogenous mouse OX40 locus, which retain mouse regulatory elements but comprise a humanization of OX40 encoding sequence, do not exhibit pathologies. Both genetically modified mice that are heterozygous or homozygous for human OX40 are grossly normal.

The present disclosure further relates to a non-human mammal generated through the method mentioned above. In some embodiments, the genome thereof contains human gene(s).

In some embodiments, the non-human mammal is a rodent, and preferably, the non-human mammal is a mouse.

In some embodiments, the non-human mammal expresses a protein encoded by a humanized OX40 gene.

In addition, the present disclosure also relates to a tumor bearing non-human mammal model, characterized in that the non-human mammal model is obtained through the methods as described herein. In some embodiments, the non-human mammal is a rodent (e.g., a mouse).

The present disclosure further relates to a cell or cell line, or a primary cell culture thereof derived from the non-human mammal or an offspring thereof, or the tumor bearing non-human mammal; the tissue, organ or a culture thereof derived from the non-human mammal or an offspring thereof, or the tumor bearing non-human mammal; and the tumor tissue derived from the non-human mammal or an offspring thereof when it bears a tumor, or the tumor bearing non-human mammal.

The present disclosure also provides non-human mammals produced by any of the methods described herein. In some embodiments, a non-human mammal is provided; and the genetically modified animal contains the DNA encoding human OX40 in the genome of the animal.

Figure 2:
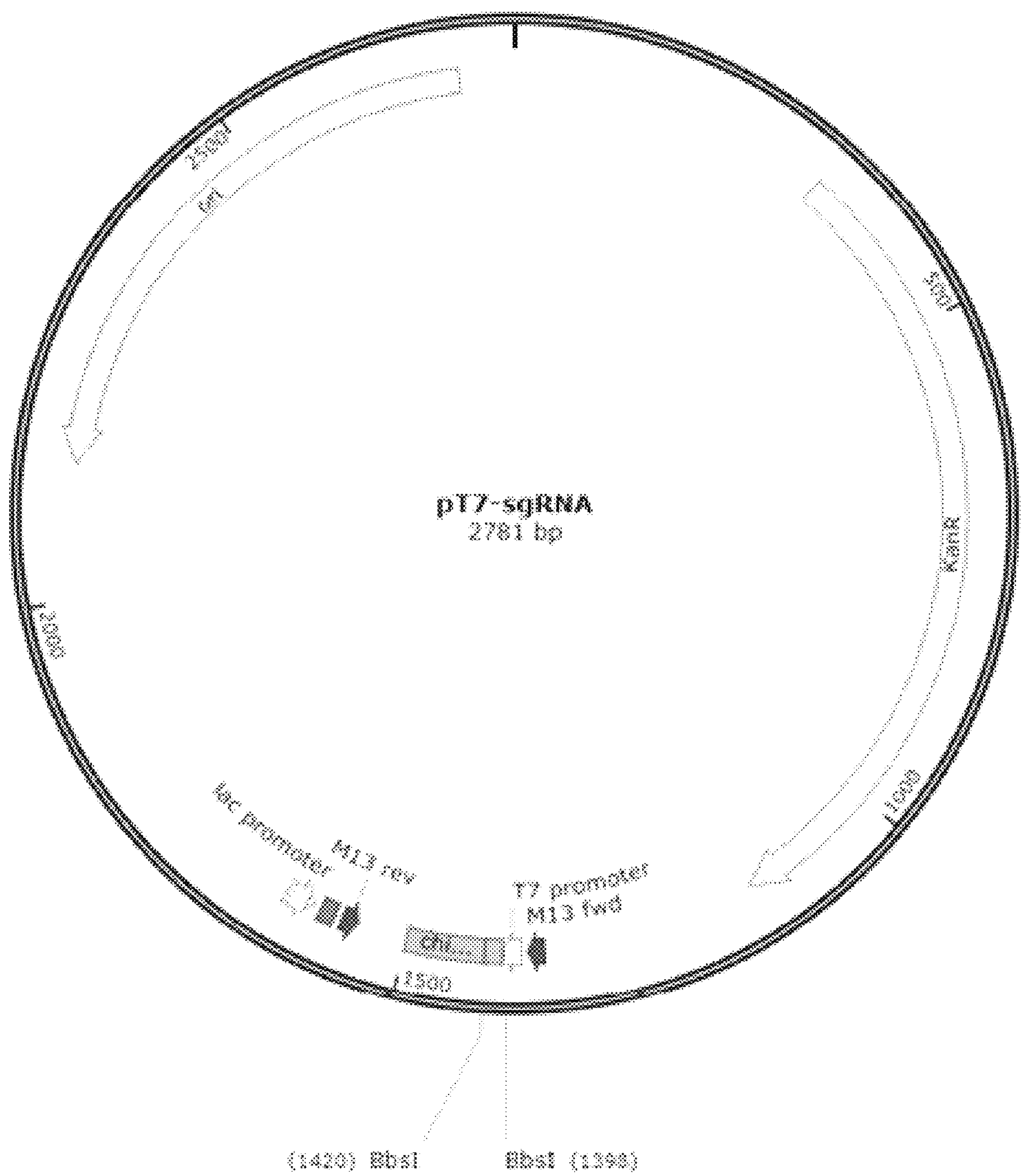
FIG. 2 is a schematic diagram showing pT7-sgRNA plasmid map.

In some embodiments, the non-human mammal comprises the genetic construct as shown in FIG. 2. In some embodiments, a non-human mammal expressing human OX40 is provided. In some embodiments, the tissue-specific expression of human OX40 protein is provided.

In some embodiments, the expression of human OX40 in a genetically modified animal is controllable, as by the addition of a specific inducer or repressor substance.

Non-human mammals can be any non-human animal known in the art and which can be used in the methods as described herein. Preferred non-human mammals are mammals, (e.g., rodents). In some embodiments, the non-human mammal is a mouse.

Genetic, molecular and behavioral analyses for the non-human mammals described above can performed. The present disclosure also relates to the progeny produced by the non-human mammal provided by the present disclosure mated with the same or other genotypes.

The present disclosure also provides a cell line or primary cell culture derived from the non-human mammal or a progeny thereof. A model based on cell culture can be prepared, for example, by the following methods. Cell cultures can be obtained by way of isolation from a non-human mammal, alternatively cell can be obtained from the cell culture established using the same constructs and the standard cell transfection techniques. The integration of genetic constructs containing DNA sequences encoding human OX40 protein can be detected by a variety of methods.

There are many analytical methods that can be used to detect exogenous DNA expression, including methods at the level of RNA (including the mRNA quantification approaches using reverse transcriptase polymerase chain reaction (RT-PCR) or Southern blotting, and in situ hybridization) and methods at the protein level (including histochemistry, immunoblot analysis and in vitro binding studies). In addition, the expression level of the gene of interest can be quantified by ELISA techniques well known to those skilled in the art. Many standard analysis methods can be used to complete quantitative measurements. For example, transcription levels can be measured using RT-PCR and hybridization methods including RNase protection, Southern blot analysis, RNA dot analysis (RNAdot) analysis. Immunohistochemical staining, flow cytometry, Western blot analysis can also be used to assess the presence of human OX40 protein.

Vectors

The present disclosure relates to a targeting vector, comprising: a) a DNA fragment homologous to the 5' end of a region to be altered (5' arm), which is selected from the OX40 gene genomic DNAs in the length of 100 to 10,000 nucleotides; b) a desired/donor DNA sequence encoding a donor region; and c) a second DNA fragment homologous to the 3' end of the region to be altered (3' arm), which is selected from the OX40 gene genomic DNAs in the length of 100 to 10,000 nucleotides.

In some embodiments, a) the DNA fragment homologous to the 5' end of a conversion region to be altered (5' arm) is selected from the nucleotide sequences that have at least 90% homology to the NCBI accession number NC_000070.6; c) the DNA fragment homologous to the 3' end of the region to be altered (3' arm) is selected from the nucleotide sequences that have at least 90% homology to the NCBI accession number NC_000070.6.

In some embodiments, a) the DNA fragment homologous to the 5' end of a region to be altered (5' arm) is selected from the nucleotides from the position 156012720 to the position 156013963 of the NCBI accession number NC_000070.6; c) the DNA fragment homologous to the 3' end of the region to be altered (3' arm) is selected from the nucleotides from the position 156016032 to the position 156017196 of the NCBI accession number NC 000070.6.

In some embodiments, the length of the selected genomic nucleotide sequence in the targeting vector can be 1.2 kb, 1.5 kb, or 1 kb.

In some embodiments, the region to be altered is exon 1, exon 2, exon 3, exon 4, exon 5, exon 6, and/or exon 7 of OX40 gene (e.g., exon 1, exon 2, exon 3, exon 4, and/or exon 5 of OX40 gene).

The targeting vector can further include a selected gene marker.

In some embodiments, the sequence of the 5' arm is shown in SEQ ID NO: 33; and the sequence of the 3' arm is shown in SEQ ID NO: 39.

In some embodiments, the target region is derived from human. For example, the target region in the targeting vector is a part or entirety of the nucleotide sequence of a human OX40, preferably the nucleotide sequence is shown as a first exon, a second exon, a third exon, a fourth exon, a fifth exon, a sixth exon, and/or a seventh exon of the DNA sequence of the human OX40. In some embodiments, the nucleotide sequence of the humanized OX40 encodes the humanized OX40 protein with the NCBI accession number NP_003318.1 (SEQ ID NO:28). For example, the sequence of the target region can have the sequence as shown in SEQ ID NO: 39.

The disclosure also relates to a cell comprising the targeting vectors as described above.

Moreover, the disclosure also relates to an sgRNA sequence for constructing a humanized animal model, wherein the sgRNA sequence targets the OX40 gene, the sgRNA is unique on the target sequence of the OX40 gene to be altered, and meets the sequence arrangement rule of 5'-NNN (20)-NGG3' or 5'-CCN-N (20)-3'; and in some embodiments, the targeting site of the sgRNA in the mouse OX40 gene is located on the exon 1, exon 2, exon 3, exon 4, exon 5, exon 6, or exon 7 of the mouse OX40 gene (e.g., exon 1 or exon 7 of the mouse OX40 gene).

In some embodiments, an upstream sequence thereof is shown as SEQ ID NO: 16, and a downstream sequence thereof is shown as SEQ ID NO: 18, and the sgRNA sequence recognizes a 5' targeting site. In some embodiments, the forward oligonucleotide sequence is obtained by adding TAGG to the 5' end of SEQ ID NO: 16; and the reverse oligonucleotide sequence is obtained by adding AAAC to the 5' end of SEQ ID NO: 18.

In some embodiments, the disclosure provides an sgRNA sequence for constructing a humanized animal model, wherein an upstream sequence thereof is shown as SEQ ID NO: 20, and a downstream sequence thereof is shown as SEQ ID NO: 22, and the sgRNA sequence recognizes a 3' targeting site. In some embodiments, the forward oligonucleotide sequence is obtained by adding TAGG to the 5' end of SEQ ID NO: 20; and the reverse oligonucleotide sequence is obtained by adding AAAC to the 5' end of SEQ ID NO: 22.

In some embodiments, the disclosure relates to a construct including the sgRNA sequence, and/or a cell including the construct.

In addition, the present disclosure further relates to a non-human mammalian cell, having any one of the foregoing targeting vectors, and one or more in vitro transcripts of the sgRNA construct as described herein. In some embodiments, the cell includes Cas9 mRNA or an in vitro transcript thereof.

In some embodiments, the genes in the cell are heterozygous. In some embodiments, the genes in the cell are homozygous.

In some embodiments, the non-human mammalian cell is a mouse cell. In some embodiments, the cell is a fertilized egg cell.

Methods of Making Genetically Modified Animals

Genetically modified animals can be made by several techniques that are known in the art, including, e.g., non-homologous end-joining (NHEJ), homologous recombination (HR), zinc finger nucleases (ZFNs), transcription activator-like effector-based nucleases (TALEN), and the clustered regularly interspaced short palindromic repeats (CRISPR)-Cas system. In some embodiments, homologous recombination is used. In some embodiments, CRISPR-Cas9 genome editing is used to generate genetically modified animals. Many of these genome editing techniques are known in the art, and is described, e.g., in Yin, Hao, Kevin J. Kauffman, and Daniel G. Anderson. "Delivery technologies for genome editing." Nature Reviews Drug Discovery 16.6 (2017): 387-399, which is incorporated by reference in its entirety. Many other methods are also provided and can be used in genome editing, e.g., micro-injecting a genetically modified nucleus into an enucleated oocyte, and fusing an enucleated oocyte with another genetically modified cell.

Thus, in some embodiments, the disclosure provides replacing in at least one cell of the animal, at an endogenous OX40 gene locus, a sequence encoding a region of an endogenous OX40 with a sequence encoding a corresponding region of human or chimeric OX40. In some embodiments, the replacement occurs in a germ cell, a somatic cell, a blastocyst, or a fibroblast, etc. The nucleus of a somatic cell or the fibroblast can be inserted into an enucleated oocyte.

Figure 5:
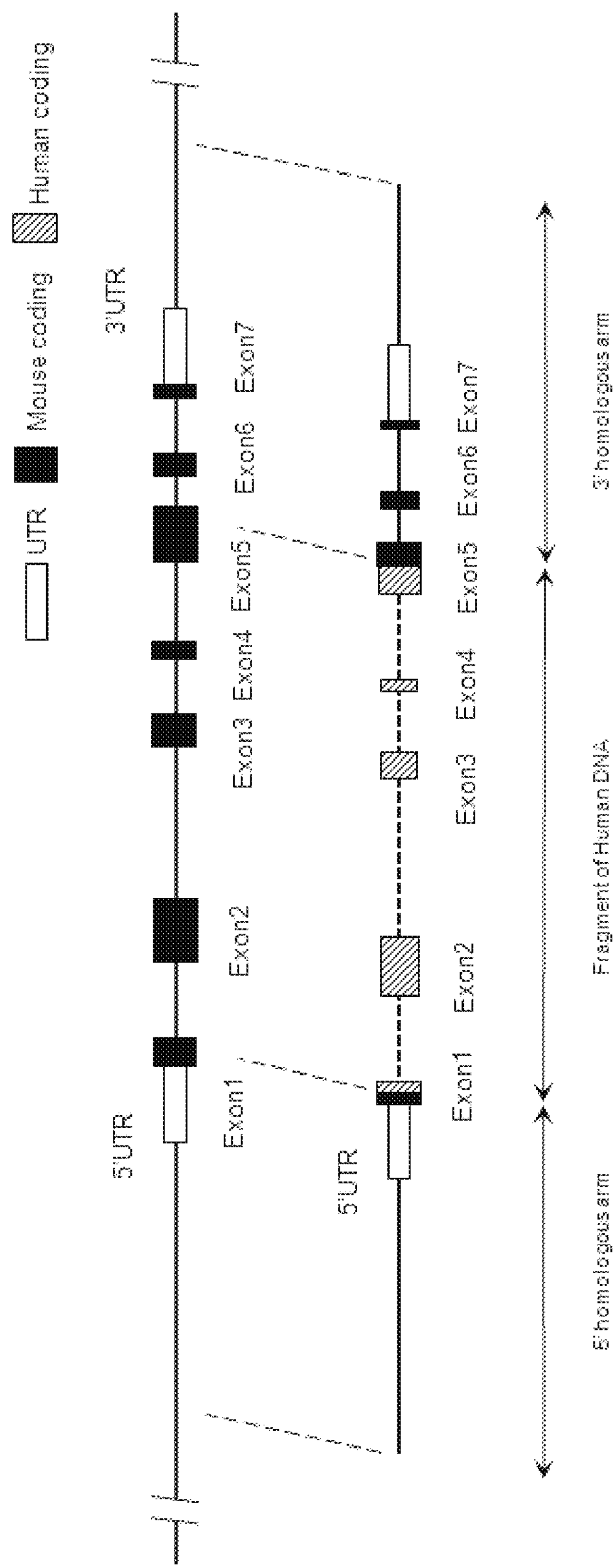
FIG. 5 is a schematic diagram showing mouse OX40 gene targeting strategy.

FIG. 5 shows a humanization strategy for a mouse OX40 locus. In FIG. 5, the targeting strategy involves a vector comprising the 5' end homologous arm, human OX40 gene fragment, 3' homologous arm. The process can involve replacing endogenous OX40 sequence with human sequence by homologous recombination. In some embodiments, the cleavage at the upstream and the downstream of the target site (e.g., by zinc finger nucleases, TALEN or CRISPR) can result in DNA double strands break, and the homologous recombination is used to replace endogenous OX40 sequence with human OX40 sequence.

Thus, in some embodiments, the methods for making a genetically modified, humanized animal, can include the step of replacing at an endogenous OX40 locus (or site), a nucleic acid encoding a sequence encoding a region of endogenous OX40 with a sequence encoding a corresponding region of human OX40. The sequence can include a region (e.g., a part or the entire region) of exon 1, exon 2, exon 3, exon 4, exon 5, exon 6, and/or exon 7 of a human OX40 gene. In some embodiments, the sequence includes a region of exon 1, exon 2, exon 3, exon 4, and/or exon 5 of a human OX40 gene (e.g., amino acids 35-197 of SEQ ID NO: 28). In some embodiments, the region is located within the extracellular region of OX40. In some embodiments, the endogenous OX40 locus is exon 1 to exon 5 of mouse OX40.

In some embodiments, the methods of modifying a OX40 locus of a mouse to express a chimeric human/mouse OX40 peptide can include the steps of replacing at the endogenous mouse OX40 locus a nucleotide sequence encoding a mouse OX40 with a nucleotide sequence encoding a human OX40, thereby generating a sequence encoding a chimeric human/mouse OX40.

In some embodiments, the nucleotide sequence encoding the chimeric human/mouse OX40 can include a first nucleotide sequence encoding an extracellular region of mouse OX40 (with or without the mouse signal peptide sequence); a second nucleotide sequence encoding an extracellular region of human OX40; a third nucleotide sequence encoding a transmembrane and a cytoplasmic region of a mouse OX40.

In some embodiments, the nucleotide sequences as described herein do not overlap with each other (e.g., the first nucleic tide sequence, the second nucleotide sequence, and/or the third nucleotide sequence do not overlap). In some embodiments, the amino acid sequences as described herein do not overlap with each other.

The present disclosure further provides a method for establishing a OX40 gene humanized animal model, comprising the following steps:

(a) providing the cell (e.g. a fertilized egg cell) based on the methods described herein;

(b) culturing the cell in a liquid culture medium;

(c) transplanting the cultured cell to the fallopian tube or uterus of the recipient female non-human mammal, allowing the cell to develop in the uterus of the female non-human mammal;

(d) identifying the germline transmission in the offspring genetically modified humanized non-human mammal of the pregnant female in step (c).

In some embodiments, the non-human mammal in the foregoing method is a mouse (e.g., a C57BL/6 mouse).

In some embodiments, the non-human mammal in step (c) is a female with pseudopregnancy (or false pregnancy).

In some embodiments, the fertilized eggs for the methods described above are C57BL/6 fertilized eggs. Other fertilized eggs that can also be used in the methods as described herein include, but are not limited to, FVB/N fertilized eggs, BALB/c fertilized eggs, DBA/1 fertilized eggs and DBA/2 fertilized eggs.

Fertilized eggs can come from any non-human animal, e.g., any non-human animal as described herein. In some embodiments, the fertilized egg cells are derived from rodents. The genetic construct can be introduced into a fertilized egg by microinjection of DNA. For example, by way of culturing a fertilized egg after microinjection, a cultured fertilized egg can be transferred to a false pregnant non-human animal, which then gives birth of a non-human mammal, so as to generate the non-human mammal mentioned in the method described above.

Methods of Using Genetically Modified Animals

Replacement of non-human genes in a non-human animal with homologous or orthologous human genes or human sequences, at the endogenous non-human locus and under control of endogenous promoters and/or regulatory elements, can result in a non-human animal with qualities and characteristics that may be substantially different from a typical knockout-plus-transgene animal. In the typical knockout-plus-transgene animal, an endogenous locus is removed or damaged and a fully human transgene is inserted into the animal's genome and presumably integrates at random into the genome. Typically, the location of the integrated transgene is unknown; expression of the human protein is measured by transcription of the human gene and/or protein assay and/or functional assay. Inclusion in the human transgene of upstream and/or downstream human sequences are apparently presumed to be sufficient to provide suitable support for expression and/or regulation of the transgene.

In some cases, the transgene with human regulatory elements expresses in a manner that is unphysiological or otherwise unsatisfactory, and can be actually detrimental to the animal. The disclosure demonstrates that a replacement with human sequence at an endogenous locus under control of endogenous regulatory elements provides a physiologically appropriate expression pattern and level that results in a useful humanized animal whose physiology with respect to the replaced gene are meaningful and appropriate and context of the humanized animal's physiology.

Genetically modified animals that express human or humanized OX40 protein, e.g., in a physiologically appropriate manner, provide a variety of uses that include, but are not limited to, developing therapeutics for human diseases and disorders, and assessing the efficacy of these human therapeutics in the animal models.

In various aspects, genetically modified animals are provided that express human or humanized OX40, which are useful for testing agents that can decrease or block the interaction between OX40 and OX40L, testing whether an agent can increase or decrease the immune response, and/or determining whether an agent is an OX40 agonist or antagonist. The genetically modified animals can be, e.g., an animal model of a human disease, e.g., the disease is induced genetically (a knock-in or knockout). In various embodiments, the genetically modified non-human animals further comprise an impaired immune system, e.g., a non-human animal genetically modified to sustain or maintain a human xenograft, e.g., a human solid tumor or a blood cell tumor (e.g., a lymphocyte tumor, e.g., a B or T cell tumor).

In some embodiments, the genetically modified animals can be used for determining effectiveness of an anti-OX40 antibody for the treatment of cancer. The methods involving administering the anti-OX40 antibody to the animal as described herein, wherein the animal has a tumor; and determining the inhibitory effects of the anti-OX40 antibody to the tumor. The inhibitor effects that can be determined include, e.g., a decrease of tumor size or tumor volume, a decrease of tumor growth, a reduction of the increase rate of tumor volume in a subject (e.g., as compared to the rate of increase in tumor volume in the same subject prior to treatment or in another subject without such treatment), a decrease in the risk of developing a metastasis or the risk of developing one or more additional metastasis, an increase of survival rate, and an increase of life expectancy, etc. The tumor volume in a subject can be determined by various methods, e.g., as determined by direct measurement, MRI or CT.

In some embodiments, the tumor comprises one or more tumor cells that express OX40L. In some embodiments, the tumor comprises one or more cancer cells (e.g., human or mouse cancer cells) that are injected into the animal. In some embodiments, the anti-OX40 antibody or anti-OX40L antibody prevents OX40 from binding to OX40L. In some embodiments, the anti-OX40 antibody or anti-OX40L antibody does not prevent OX40 binding to OX40L.

In some embodiments, the genetically modified animals can be used for determining whether an anti-OX40 antibody is an OX40 agonist or antagonist. In some embodiments, the methods as described herein are also designed to determine the effects of the agent (e.g., anti-OX40 antibodies) on OX40, e.g., whether the agent can stimulate T cells or inhibit T cells, whether the agent can upregulate the immune response or downregulate immune response. In some embodiments, the genetically modified animals can be used for determining the effective dosage of a therapeutic agent for treating a disease in the subject, e.g., cancer.

The inhibitory effects on tumors can also be determined by methods known in the art, e.g., measuring the tumor volume in the animal, and/or determining tumor (volume) inhibition rate ($TGI_{TV}$). The tumor growth inhibition rate can be calculated using the formula $TGI_{TV}$ (%)=(1−TVt/TVc)×100, where TVt and TVc are the mean tumor volume (or weight) of treated and control groups.

In some embodiments, the anti-OX40 antibody is designed for treating various cancers. As used herein, the term "cancer" refers to cells having the capacity for autonomous growth, i.e., an abnormal state or condition characterized by rapidly proliferating cell growth. The term is meant to include all types of cancerous growths or oncogenic processes, metastatic tissues or malignantly transformed cells, tissues, or organs, irrespective of histopathologic type or stage of invasiveness. The term "tumor" as used herein refers to cancerous cells, e.g., a mass of cancerous cells. Cancers that can be treated or diagnosed using the methods described herein include malignancies of the various organ systems, such as affecting lung, breast, thyroid, lymphoid, gastrointestinal, and genito-urinary tract, as well as adenocarcinomas which include malignancies such as most colon cancers, renal-cell carcinoma, prostate cancer and/or testicular tumors, non-small cell carcinoma of the lung, cancer of the small intestine and cancer of the esophagus. In some embodiments, the agents described herein are designed for treating or diagnosing a carcinoma in a subject. The term "carcinoma" is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. In some embodiments, the cancer is renal carcinoma or melanoma. Exemplary carcinomas include those forming from tissue of the cervix, lung, prostate, breast, head and neck, colon and ovary. The term also includes carcinosarcomas, e.g., which include malignant tumors composed of carcinomatous and sarcomatous tissues. An "adenocarcinoma" refers to a carcinoma derived from glandular tissue or in which the tumor cells form recognizable glandular structures. The term "sarcoma" is art recognized and refers to malignant tumors of mesenchymal derivation.

In some embodiments, the anti-OX40 antibody is designed for the treating melanoma, non-small cell lung carcinoma (NSCLC), small cell lung cancer (SCLC), bladder cancer, and/or prostate cancer (e.g., metastatic hormone-refractory prostate cancer). Anti-OX40 antibodies are known in the art, and are described in, e.g., U.S. Pat. No. 9,006,399, WO 2015153513, and WO 2013038191, each of which is incorporated by reference in its entirety.

The present disclosure also relates to the use of the animal model generated through the method as described herein in the development of a product related to an immunization processes of human cells, the manufacturing of a human antibody, or the model system for a research in pharmacology, immunology, microbiology and medicine.

In some embodiments, the disclosure provides the use of the animal model generated through the method as described herein in the production and utilization of an animal experimental disease model of an immunization processes involving human cells, the study on a pathogen, or the development of a new diagnostic strategy and/or a therapeutic strategy.

The disclosure also relates to the use of the animal model generated through the method mentioned above in the screening, verifying, evaluating or studying the OX40 gene function, human OX40 antibodies, drugs for human OX40 targeting sites, the drugs or efficacies for human OX40 targeting sites, the drugs for immune-related diseases and antitumor drugs.

Genetically Modified Animal Model with Two or More Human or Chimeric Genes

The present disclosure further relates to methods for genetically modified animal model with two or more human or chimeric genes. The animal can comprise a human or chimeric OX40 gene and a sequence encoding an additional human or chimeric protein.

In some embodiments, the additional human or chimeric protein can be programmed cell death protein 1 (PD-1), cytotoxic T-lymphocyte-associated protein 4 (CTLA-4), Lymphocyte Activating 3 (LAG-3), T-Cell Immunoglobulin And Mucin Domain-Containing Protein 3 (TIM-3), Programmed Cell Death 1 Ligand 1 (PD-L1), TNF Receptor Superfamily Member 9 (4-1BB), CD27, CD28, CD47, T-Cell Immunoreceptor With Ig And ITIM Domains (TIGIT), CD27, Glucocorticoid-Induced TNFR-Related Protein (GITR), or B And T Lymphocyte Associated (BTLA).

The methods of generating genetically modified animal model with two or more human or chimeric genes (e.g., humanized genes) can include the following steps:

(a) using the methods of introducing human OX40 gene or chimeric OX40 gene as described herein to obtain a genetically modified non-human animal;

(b) mating the genetically modified non-human animal with another genetically modified non-human animal, and then screening the progeny to obtain a genetically modified non-human animal with two or more human or chimeric genes.

In some embodiments, in step (b) of the method, the genetically modified animal can be mated with a genetically modified non-human animal with human or chimeric PD-1, CTLA-4, LAG-3, TIM-3, PD-L1, 4-1BB, CD27, CD28, CD47, TIGIT, CD27, GITR, or BTLA.

In some embodiments, the OX40 humanization is directly performed on a genetically modified animal having a human or chimeric PD-1, CTLA-4, LAG-3, TIM-3, PD-L1, 4-1BB, CD27, CD28, CD47, TIGIT, CD27, GITR, or BTLA gene.

As these proteins may involve different mechanisms, a combination therapy that targets two or more of these proteins thereof may be a more effective treatment. In fact, many related clinical trials are in progress and have shown a good effect. The genetically modified animal model with two or more human or humanized genes can be used for determining effectiveness of a combination therapy that targets two or more of these proteins, e.g., an anti-OX40 antibody and an additional therapeutic agent for the treatment of cancer. The methods include administering the anti-OX40 antibody and the additional therapeutic agent to the animal, wherein the animal has a tumor; and determining the inhibitory effects of the combined treatment to the tumor.

In some embodiments, the animal further comprises a sequence encoding a human or humanized programmed cell death protein 1 (PD-1). In some embodiments, the additional therapeutic agent is an anti-PD-1 antibody (e.g., nivolumab, pembrolizumab, avelumab, durvalumab, atezolizumab). In some embodiments, the tumor comprises one or more tumor cells that express OX40L, CD80, CD86, PD-L1 or PD-L2.

In some embodiments, the combination treatment is designed for treating various cancer as described herein, e.g., melanoma, non-small cell lung carcinoma (NSCLC), small cell lung cancer (SCLC), bladder cancer, and/or prostate cancer (e.g., metastatic hormone-refractory prostate cancer).

In some embodiments, the methods described herein can be used to evaluate the combination treatment with some other methods. The methods of treating a cancer that can be used alone or in combination with methods described herein, include, e.g., treating the subject with chemotherapy, e.g., campothecin, doxorubicin, cisplatin, carboplatin, procarbazine, mechlorethamine, cyclophosphamide, adriamycin, ifosfamide, melphalan, chlorambucil, bisulfan, nitrosurea, dactinomycin, daunorubicin, bleomycin, plicomycin, mitomycin, etoposide, verampil, podophyllotoxin, tamoxifen, taxol, transplatinum, 5-flurouracil, vincristin, vinblastin, and/or methotrexate. Alternatively or in addition, the methods can include performing surgery on the subject to remove at least a portion of the cancer, e.g., to remove a portion of or all of a tumor(s), from the patient.

EXAMPLES

The invention is further described in the following examples, which do not limit the scope of the invention described in the claims.

Materials and Methods

The following materials were used in the following examples.

Ambion™ in vitro transcription kit was purchased from Ambion.Catalog number is AM1354.

*E. coli* TOP10 competent cells were purchased from the TiangenBiotech (Beijing) Co. Catalog number is CB104-02.

EcoRI, ScaI, HindIII, BglII, BamHI were purchased from NEB. Catalog numbers are R3101M, R3122M, R3104M, R0144M, R3136M.

Kanamycin was purchased from Amresco.Catalog number is 0408.

Cas9 mRNA was obtained from SIGMA.Catalog number is CAS9MRNA-1EA.

AIO kit was obtained from Beijing Biocytogen Co., Ltd. Catalog number is BCG-DX-004.

UCA kit was obtained from Beijing Biocytogen Co., Ltd. Catalog number is BCG-DX-001.

C57BL/6 mice were purchased from the China Food and Drugs Research Institute National Rodent Experimental Animal Center.

Reverse Transcription Kit was obtained from TakaRa-.Catalog number is 6110A.

Mouse colon cancer cell line MC38 was purchased from Shanghai Enzyme Research Biotechnology Co., Ltd.

Mouse CD3 antibody was obtained from BD.Catalog number is 563123.

mTcRβPerCP was obtained from Biolegend.Catalog number is 109228.

mPD-1_PE was obtained from Biolegend.Catalog number is 109104.

mOX40 APC was obtained from Biolegend.Catalog number is 119414.

hOX40 PE was obtained from Biolegend.Catalog number is 350004.

hPD-1 FITC was obtained from Biolegend.Catalog number is 329904.

Example 1: Construction of pT7-OX-6 and pT7-OX-12

The target sequence determines the targeting specificity of small guide RNA (sgRNA) and the efficiency of Cas9 cleavage at the target gene. Therefore, target sequence selection is important for sgRNA vector construction.

The 5'-terminal targeting sites (sgRNA1 to sgRNA7) and the 3'-terminal targeting sites (sgRNA9 to sgRNA16) were designed and synthesized. The 5'-terminal targeting sites and the 3'-terminal targeting sites are located on exon 2 and exon 5 of mouse OX40 gene respectively, and the targeting site sequence on OX40 of each sgRNA is as follows:

sgRNA-1 targeting sequence (SEQ ID NO: 1):
5'-GTTAAACATACCTACCCCAGTGG-3' sgRNA-2 targeting sequence (SEQ ID NO: 2):
5'-CGACAGCACTTGTGACCACTGGG-3' sgRNA-3 targeting sequence (SEQ ID NO: 3):
5'-TCAAAGCCAGGCTACTCACCTGG-3' sgRNA-4 targeting sequence (SEQ ID NO: 4):
5'-TGCTGTCGTGAGTGCCAGCCAGG-3' sgRNA-5 targeting sequence (SEQ ID NO: 5):
5'-TGCCAGCCAGGTGAGTAGCCTGG-3'

-continued sgRNA-6 targeting sequence (SEQ ID NO: 6):
5'-AGCCAGGCTACTCACCTGGCTGG-3' sgRNA-7 targeting sequence (SEQ ID NO: 7):
5'-GCACTTGTGACCACTGGGGTAGG-3' sgRNA-9 targeting sequence (SEQ ID NO: 8):
5'-TTGGCCTGAATGTAGGGCGCTGG-3' sgRNA-10 targeting sequence (SEQ ID NO: 9):
5'-AGACCCAGCGCCCTACATTCAGG-3' sgRNA-11 targeting sequence (SEQ ID NO: 10):
5'-ACAGTGGTTGGCCTGAATGTAGG-3' sgRNA-12 targeting sequence (SEQ ID NO: 11):
5'-GACTGTGGTGGATTGGACAGTGG-3' sgRNA-13 targeting sequence (SEQ ID NO: 12):
5'-CTGTCCAATCCACCACAGTCTGG-3' sgRNA-14 targeting sequence (SEQ ID NO: 13):
5'-TGGGCCAGACTGTGGTGGATTGG-3 sgRNA-15 targeting sequence (SEQ ID NO: 14):
5'-AATCCACCACAGTCTGGCCCAGG-3' sgRNA-16 targeting sequence (SEQ ID NO: 15):
5'-GAGGGCAACTCAGAAGTCCTGGG-3'

The UCA kit was used to detect the activities of sgRNAs (FIGS. 1A and 1B). The results show that the guide sgRNAs have different activities. Two of them (sgRNA1 and sgRNA12, respectively) were selected for follow-up experiments. TAGG was added to the 5' end to obtain a forward oligonucleotide sequence, and its complementary strand was added with AAAC to obtain a reverse oligonucleotide sequence. After annealing, they were respectively digested by restriction enzyme (BbsI) and ligated to pT7-sgRNA plasmid to obtain the expression vectors pT7-OX-1 and pT7-OX-12.

TABLE 3

| sgRNA1 and sgRNA12 sequences | |
|---|---|
| sgRNA1 sequences | |
| SEQ ID NO: 16 | Upstream: 5'-TTAAACATACCTACCCCAG-3' |
| SEQ ID NO: 17 (adding TAGG to obtain a forward oligonucleotide sequence) | Upstream: 5'-TAGGTTAAACATACCTACCCCAG-3' |
| SEQ ID NO: 18 | Downstream: 5'-CTGGGGTAGGTATGTTTAA-3' |
| SEQ ID NO: 19 (complementary strand was added with AAAC to obtain a reverse oligonucleotide sequence) | Downstream: 5'-AAACCTGGGGTAGGTATGTTTAA-3' |
| sgRNA12 | |
| SEQ ID NO: 20 | Upstream: 5'-ACTGTGGTGGATTGGACAG-3' |
| SEQ ID NO: 21 (adding TAGG to obtain a forward oligonucleotide sequence) | Upstream: 5'-TAGGACTGTGGTGGATTGGACAG-3' |
| SEQ ID NO: 22 | Downstream: 5'-CTGTCCAATCCACCACAGT-3' |
| SEQ ID NO: 23 (complementary strand was added with AAAC to obtain a reverse oligonucleotide sequence) | Downstream: 5'-AAACCTGTCCAATCCACCACAGT-3' |

TABLE 4

| The ligation reaction conditions | |
|---|---|
| Double stranded fragment | 1 μL (0.5 μM) |
| pT7-sgRNA vector | 1 μL (10 ng) |
| T4 DNA Ligase | 1 μL (5U) |
| 10 × T4 DNA Ligase buffer | 1 μL |
| 50% PEG4000 | 1 μL |
| $H_2O$ | Add to 10 μL |

Reaction Conditions:

The ligation reaction was carried out at room temperature for 10 to 30 min. The ligation product was then transferred to 30 μL of TOP10 competent cells. The cells were then plated on a petri dish with Kanamycin, and then cultured at 37° C. for at least 12 hours and then two clones were selected and added to LB medium with Kanamycin (5 ml), and then cultured at 37° C. at 250 rpm for at least 12 hours.

Randomly selected clones were sequenced, so as to verify their sequences. The correct expression vectors pT7-OX-1 and pT7-OX-12 were selected for subsequent experiments.

Source of pT7-sgRNA Plasmid

PT7-sgRNA vector map is shown in FIG. 2. The plasmid backbone was obtained from Takara (Catalog No. 3299). The DNA fragment containing T7 promoter and sgRNA scaffold was synthesized by a plasmid synthesis company, and linked to the backbone vector by restriction enzyme digestion (EcoRI and BamHI) and ligation. The target plasmid was confirmed by the sequencing results.

The DNA fragment containing the T7 promoter and sgRNA scaffold (SEQ ID NO: 24):

```
gaattctaatacgactcactataggggtcttcgagaagacctgttttag
agctagaaatagcaagttaaaataaggctagtccgttatcaacttgaaaa
agtggcaccgagtcggtgcttttaaaggatcc
```

Example 2. Construction of Vector pClon-4G-OX40

Figure 4:
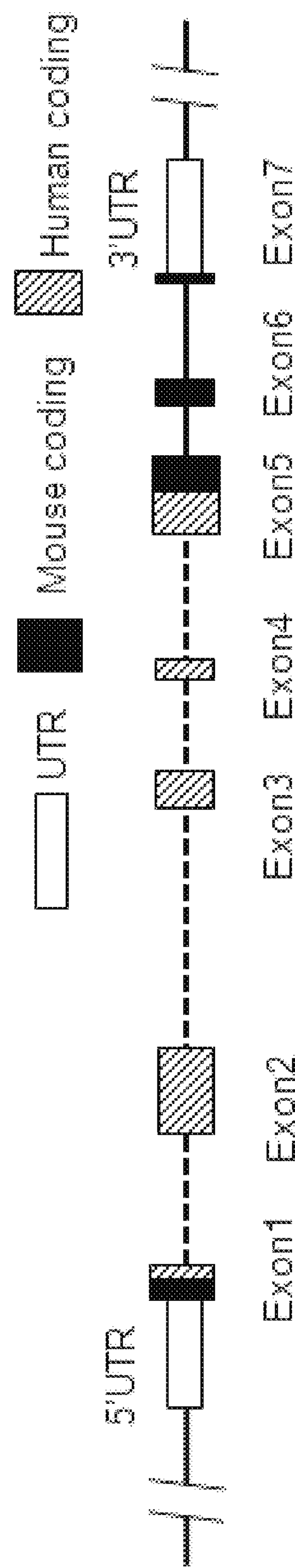
FIG. 4 is a schematic diagram showing humanized OX40 mouse gene map.

A partial coding sequence of the mouse OX40 gene (Gene ID: 22163) from exon 2 to exon 5 (based on the transcript of NCBI accession number NM_011659.2→NP_035789.1 whose mRNA sequence is shown in SEQ ID NO: 25, and the corresponding protein sequence is shown in SEQ ID NO: 26) was replaced with a corresponding coding sequence of human homologous OX40 gene (Gene ID: 7293) (based on the transcript of NCBI accession number NM_003327.3→NP_003318.1, whose mRNA sequence was shown in SEQ ID NO: 27, and the corresponding protein sequence is shown in SEQ ID NO: 28). The comparison between the mouse OX40 and human OX40 is shown in FIG. 3, and the finally obtained humanized OX40 gene is shown in FIG. 4, the humanized mouse OX40 gene DNA sequence (chimeric OX40 gene DNA) is shown in SEQ ID NO: 29.

```
TGTTAAACATacatatcctagcaacgaccggtgctgccacgagtgcaggc
caggtgaggcctcaggaggggtcgccacgcacgggcactccagggactgg
gggctggggcagggatgggccagccaggaggctggtcctggggaggggc
gggtgaggggccggccaagcctggcagaggagccgcctggggggtccac
gggcgcaagcctggggcctgaccgctgcctgacgccggcctctgctgcag
gcaacgggatggtgagccgctgcagccgctcccagaacacggtgtgccgt
```

-continued

```
ccgtgcgggccgggcttctacaacgacgtggtcagctccaagccgtgcaa
gccctgcacgtggtgtaacctcagtgagctcccacctggccccacagccc
cacccagcacaggggggcggcagcctggcacccacattcccacgcagcagc
atggggctcccacagccgcagaaacgaacctcaaaccacagcggggtctg
ctccgccacaggggtccttcgaggagctgaggcgtctcccaggggcaccc
cctctccctccgggggcccagactcggcccaggccacgtggagtcgggga
gaccacgctggccatgtggcctggccttgctggcctgagcagtgaggctg
gggggttgggccatggagaccctgccgcaggcggggctggcggctggagg
cggtggaggggtagggaagggtggctggggctgccacggaaccagcccca
ggttgtggccaggaagggagggcccaggagcctcgggggctgcaggggct
ccaagtctcaggggaggccgcagacccctgcccacggccctctgtgtggt
ggggaggccaacctgtcctccagtgcccacgcttcctgaggaccctgtcc
acagcccccacctgaccacccccccatccggcccctgctcaggaagtggg
agtgagcggaagcagctgtgcacggccacacaggacacagtctgccgctg
ccgggcgggcacccagcccctggacagctacaagcctggagttggtgagc
tcggtggctgcggccggcggttgggggtgtgcatagcggctgtctgtgac
gcagatgggccgtgggccgcagggacctggccccaccggtgcctcctctg
gcatcctcaagaccgagctcccgggtcagggcccacgggtgggatgtggg
cagggagggcttccagaggccaaacccaccacccagccatgggggcaag
tgcctgccccacaggctctgccccatgtccccagcacccggggcctgtgg
gcagcccctgaccaccctatattgttgcagactgtgcccccctgccctcca
gggcacttctccccaggcgacaaccaggcctgcaagccctggaccaagtg
aggggcctggccaggggctgggaggggctgggggggggttggggtggtta
ggagggcggaggagctggggagctgggaggggctgggggggcaggtgggg
tgggggcagttttgggggaaggggaggtgctggtggccctgggggcctgg
ctatgtggctggacctggttggggagcaggaagctgctgcctgggggcag
cattccctgtgggtggagctgggtgtgtgggaccctcaccctccgcagct
gggaggccctgggggcacaggacagggaggtgctggtgggggtgtagat
gtgggagaagggtgtgtggccttggaggcccctgtgggggcacgtgggg
ctgggcagcgtccttggctgtcactggcctggtgtctgtggtagatgctg
cctgtggctggccagcgtggaccctgttatccccaccgcatctcccgggt
cccaggggctctggcctgagcaacacctcctgaccccaacagctgcacct
tggctgggaagcacaccctgcagccggccagcaatagctcggacgcaatc
tgtgaggacagggacccccccagccacgcagccccaggagacccagggccc
cccggccaggcccatcactgtccagcccactgaagcctggcccagaACTT
CTGAGTTGCC
```

SEQ ID NO: 29 lists only the portion of DNA sequence involved in the modification, wherein the italicized underlined region is the human OX40 gene sequence fragment.

The coding region sequence, mRNA sequence and the encoded protein sequence thereof of the modified human OX40 are respectively shown in SEQ ID NO: 30, SEQ ID NO: 31, and SEQ ID NO: 32.

A targeting strategy involving a vector comprising the 5' end homologous arm, human OX40 gene fragment, 3' homologous arm as shown in FIG. 5 is also developed. The process is as follows:

(1). Design upstream primers of homologous recombination fragments, and downstream primers matching therewith, as well as other related sequences. Specifically:

5' end homologous arm (SEQ ID NO: 33), nucleotide sequence of the positions from 156012720 to 156013963 of the NCBI accession number NC 000070.6 as follows:

```
aatgtgtagtaaaggcactgcccccctgctaactcatttcctccttcagtg
cagtggtttgagtgtaagaaaagaaggcccgcgttgagctcactgacaca
cacctgtcgtcgcagcatttgggaggtggaggcaggaagatggggggtac
aaggtcatcgagatggttcactcagtagaactacttgccacaacccaaat
ttggtcctcagtatcaacaccatgcagctcacaactgcctataatctagc
tctaggggggatcagacatctctggcctcctagggccacgtgtaagtcccc
tcccccaacatacacacacacacacacacacacacacagagttaaaaata
aatctattttaaaaatctaagcatgggctacagaatgagttcaaatgtta
gcctgggcaacttagtgaaactgttaaaagaaaacatgaagagagctgtg
gctctagctcagtggtcgaacgctgcccagcaagtaaaacgcttaggctc
ttagcattataaaaaaggaaggagaataaatccactggcacggagagatg
gctaagtagttaagcttgtactgctctcttgggtgtttttgtttttgaga
caaagtctctcttatacaatctggctgccctgagacttaactatgtagac
tgggcagagctgcctgcttccatctcctgagtactggctttaaagaagtg
tactgccatgcccagtggtaagagcatgcgttcttgcagagaaccaaagt
tcagtttccagcactcatgatggtggttcaccactgcctataactctagc
tcttctgacttccctgggcattatacttaccatacatataccttccccc
tcaaaaaagaaataaaattaaaaataaatttttttcttaatgcctgtgtg
cacgtgtgtgtttctttgtgtgcttcgtgtgcatatgttgggtatctgca
cctctcttcacgttccccagcggcccaaagcacttcttagcttatcatgg
gactctgcatacgcctgtgccaaatacacaggaacacgttcacatacctt
cttgcctgtccgcctactcttcttgccccacctccatagttcttatagcc
acaccctgcaaggaaaaaccccagactcctgtgaaggcagaaagcagaca
aggatgtatgtgtgggttcagcagcccacagcccttctgctgctgggact
cacacttggagttacagcaaggcggctcaactgtgttaaacat
```

```
Upstream primer (SEQ ID NO: 34):
F: 5'-TTTAAGAAGGAGATATACATGAATGTGTAGTAAAGGCACTGCCC
CC-3'

Downstream primer (SEQ ID NO: 35):
R: 5'-GTTGCTAGGATATGTATGTTTAACACAGTTGAGCCGCCTTGC-
3'
```

(2). Design the primers and related sequences of the desired conversion region. Human DNA fragment (SEQ ID NO: 36). As compared to the nucleotide sequence from positions 1211985 to 1214025 of the NCBI accession number NC_000001.11, the following nucleotides are different: 3C→A, 6C→T, 9C→T

```
acatatcctagcaacgaccggtgctgccacgagtgcaggccaggtgaggc
ctcaggaggggtcgccacgcacgggcactccagggactgggggctggggc
agggatgggccagccaggaggctggtcctggggagggggcgggtgagggg
ccggccaagcctggcagaggagccgcctggggggtccacgggcgcaagc
ctggggcctgaccgctgcctgacgccggcctctgctgcaggcaacgggat
ggtgagccgctgcagccgctcccagaacacggtgtgccgtccgtgcgggc
cgggcttctacaacgacgtggtcagctccaagccgtgcaagccctgcacg
tggtgtaacctcagtgagctcccacctggccccacagccccacccagcac
agggggcggcagcctggcacccacattcccacgcagcagcatggggctcc
cacagccgcagaaacgaacctcaaaccacagcggggtctgctccgccaca
ggggtccttcgaggagctgaggcgtctcccaggggcacccccctctccctc
cgggggcccagactcggcccaggccacgtggagtcggggagaccacgctg
gccatgtggcctggccttgctggcctgagcagtgaggctgggggttggg
ccatggagaccctgccgcaggcggggctggcggctggaggcggtggaggg
gtagggaagggtggctggggctgccacggaaccagccccaggttgtggcc
aggaagggagggcccaggagcctcgggggctgcaggggctccaagtctca
ggggaggccgcagacccctgcccacggccctctgtgtggtggggaggcca
acctgtcctccagtgcccacgcttcctgaggaccctgtccacagcccccca
cctgaccacccccccatccggcccctgctcaggaagtgggagtgagcgga
agcagctgtgcacggccacacaggacacagtctgccgctgccgggcgggc
acccagcccctggacagctacaagcctggagttggtgagctcggtggctg
cggccggcggttgggggtgtgcatagcggctgtctgtgacgcagatgggc
cgtgggccgcagggacctggccccaccggtgcctcctctggcatcctcaa
gaccgagctcccgggtcagggcccacgggtgggatgtgggcagggagggc
ttccagaggccaaacccaccacccagccatgggggggcaagtgcctgcccc
acaggctctgccccatgtccccagcacccggggcctgtgggcagcccctg
accaccctatctttgttgcagactgtgcccccctgccctccagggcacttc
tccccaggcgacaaccaggcctgcaagccctggaccaagtgaggggcctg
gccaggggctgggaggggctgggggggggttggggtggttaggagggcgg
aggagctggggagctgggaggggctgggggggcaggtggggtgggggcag
ttttgggggaaggggaggtgctggtggccctgggggcctggctatgtggc
tggacctggttggggagcaggaagctgctgcctgggggcagcctttccct
gtgggtggagctgggtgtgtgggaccctcaccctccgcagctgggaggcc
ctgggggcacaggacagggaggtgctggtggggggtgtagatgtgggaga
agggtgtgtggccttggaggcccctgtgggggggcacgtggggctgggcag
cgtccttggctgtcactggcctggtgtctgtggtagatgctgcctgtggc
tggccagcgtggaccctgttatccccaccgcatctcccgggtcccagggg
gtttctggcctgagcaacacctcctgttccccaacagctgcaccttggct
gggaagcacaccctgcagccggccagcaatagctcggacgcaatctgtga
ggacagggacccccccagccacgcagccccaggagacccagggcccccccgg
ccaggcccatcactgtccagcccactgaagcctggcccaga
```

-continued

```
The upstream primer (SEQ ID NO: 37) is:
F: 5'-GTGTTAAACATACATATCCTAGCAACGACCGGTGCTGCCA-3'

The downstream primer (SEQ ID NO: 38) is:
R: 5'-CTCAGAAGTTCTGGGCCAGGCTTCAGTGGGCTGGACAGTGA-3'
```

(3). Design the upstream primers of the homologous recombination fragment and the downstream primers matching therewith, as well as other related sequences. Specifically:

3' homologous arm (SEQ ID NO: 39), which was the nucleotide sequence from positions 156016032 to 156017196 of the NCBI accession number NC_000070.6:

```
ACTTCTGAGTTGCCCTCTCCACCCACcttggtgactcctgagggtaaggg

acactggcgcagtggaggatagggagagaactcaagggtgagcgagttta

ctcagttggcctctcctcataggccctgcatttgctgttctcctaggcct

gggcctgggcctgctggctcccttgactgtcctgctggccttgtacctgc

tccggaaggcttggagattgcctaacactcccaaaccttgttgtgagtat

cacattgggctcagtaaagcctacctccttcacgatgagccatagctcct

cactgctctttccttctgtgcttctcttaggggaaacagcttcaggacc

ccgatccaggaggaacacacagacgcacactttactctggccaagatctg

agcattactacaggagtggattttatggggcacggacaacccatatcctg

atgcctgccagtaccctccacaccgttctaggtgctgggctggctctggg

attcctatgtatgctatgcatactacctgcctggtggtgctcctaataaa

catgctagcagctgtgagtctgtgactggcactagggctgaggtggcctc

ctattctggttggggagggtttggggccaaaatgaaggtccactcagaga

cctacacttggtcacatgtactccagtgtgagtacgggtatggaattcag

agacctgaaatgccaaggggaaagtacctggggagccaactggcaactcg

atgagcagtccagagtatactctaaggcaggggttctcagccttcttagt

gctgtgacccttttaatacagtttcacatgttgtggtggccccaaaccat

gaaactgttttctttgcctattttttttccatcttttattattattatta

ttattaggtattttcctcgtttacattttcaatgctatcccaaaggtccc

ccatacccacccccccaatcccctacccacccttctttgccttttgataac

aatagttttgctactgttatgaatcataatgcaagtattattgagataga

ggtttgcctaaagggctgcagcacacaggttaagaaacactgctctaagt

ggacctaagagtcttagccaaatggaaaagtcctggcaagcagagcctaa

gtaccgaggtca

Upstream primer (SEQ ID NO: 40):
F: 5'-CCACTGAAGCCTGGCCCAGAACTTCTGAGTTGCCCTCTCCACCC
AC-3'

Downstream primer (SEQ ID NO: 41):
R: 5'-GTTGTTAGCAGCCGGATCTCAGTGACCTCGGTACTTAGGCTCTG
C-3'
```

C57BL/6 mouse DNA or BAC library is used as the template to carry out PCR amplification for the 5'-terminal homologous arm fragment (SEQ ID NO: 33) and the 3'-terminal homologous arm fragment (SEQ ID NO: 39). Human DNA is used as the template to carry out PCR amplification for the DNA fragment (SEQ ID NO: 36), and the AIO kit is used to ligate the fragments to the pClon-4G plasmid provided by the kit, so as to obtain the vector pClon-4G-OX40.

Example 3. Verification of vector pClon-4G-OX40

Figures 6A, 6B:
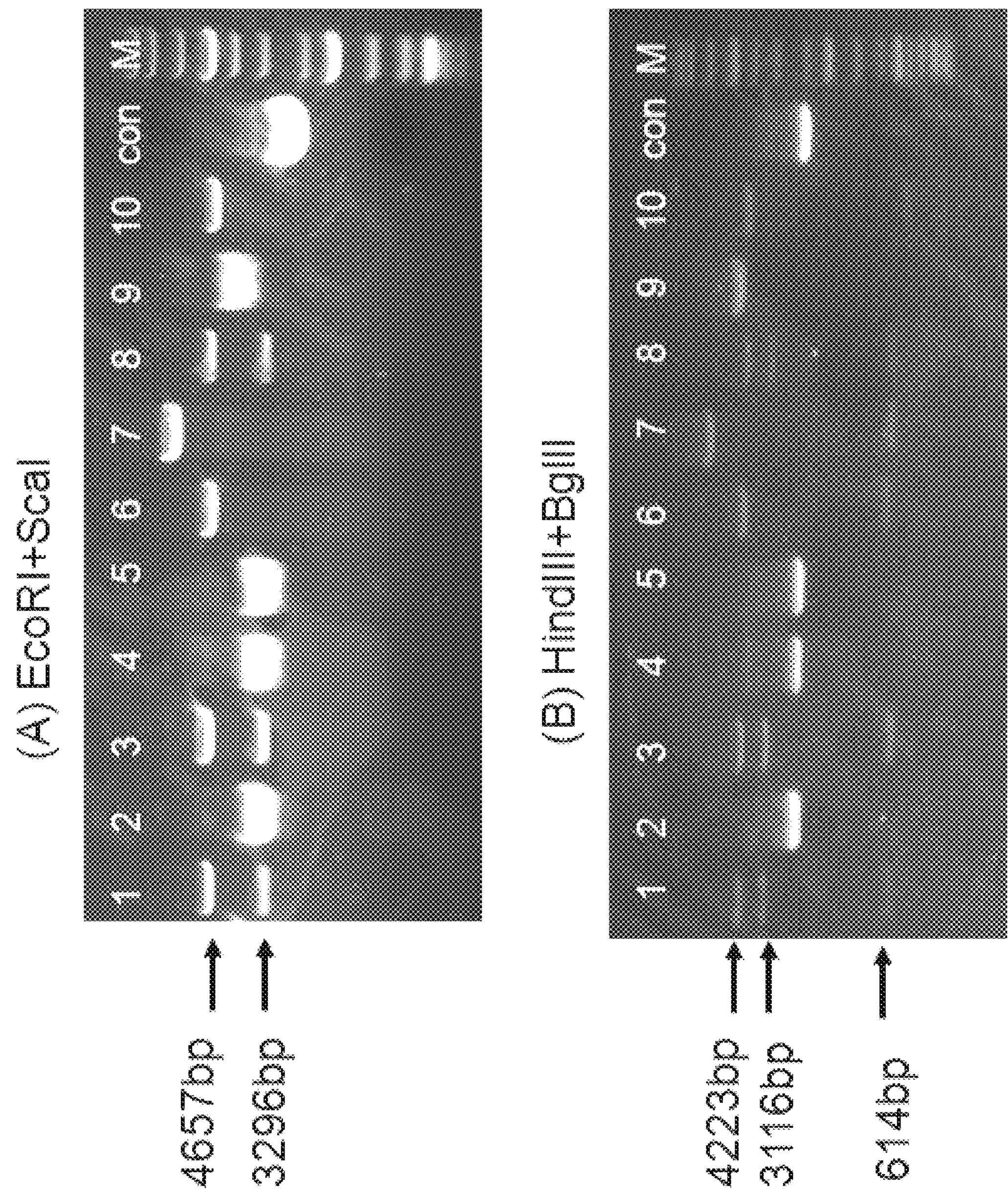
FIGS. 6A-6B show pClon-4G-OX40 plasmid digestion result (M is the Marker, con is the positive control). The results for Plasmids 1, 3, 8 are in line with the expected results.

Ten pClon-4G-OX40 clones were randomly selected and identified by two sets of enzymes. Among them, EcoRI+ScaI should generate 4657 bp+3296 bp fragments, HindIII+BglII should generate 4223 bp+3116 bp+614 bp fragments. The results for Plasmids 1, 3, and 8 were in line with the expectations (FIG. 6). The sequences of Plasmids 1 and 3 were verified by sequencing. Plasmid 3 was selected for subsequent experiments.

Example 4. Microinjection and Embryo Transfer

The pre-mixed Cas9 mRNA, pClon-4G-OX40 plasmid and in vitro transcription products of pT7-OX-1, pT7-OX-12 plasmids were injected into the cytoplasm or nucleus of mouse fertilized eggs (C57BL/6 background) with a microinjection instrument (using in vitro transcription kit to carry out the transcription according to the method provided in the product instruction). The embryo microinjection was carried out according to the method described, e.g., in A. Nagy, et al., "Manipulating the Mouse Embryo: A Laboratory Manual (Third Edition)," Cold Spring Harbor Laboratory Press, 2003. The injected fertilized eggs were then transferred to a culture medium for a short time culture, and then was transplanted into the oviduct of the recipient mouse to produce the genetically modified humanized mice. The mice population was further expanded by cross-mating and self-mating to establish stable mouse lines. The humanized mouse obtained was named B-hOX40.

Example 5. Identification of Genetically Modified Humanized Mouse Model

1. Genotype Detection

PCR analysis was performed for mouse tail genomic DNA of 8 mice. The primers for PCR-1 were located on the left side of the 5' homologous arm, the primers for PCR-4 were located on the right side of the 3' homologous arm; in addition, the primers for PCR-2 and PCR-3 were located on the humanized fragment, which are shown below:

```
5' terminus primers:
PCR-1 (SEQ ID NO: 42):
5'-ATTTCCAGCCCCAGTCCTATTCCCT-3';

PCR-2 (SEQ ID NO: 43):
5'-CTCGGTCTTGAGGATGCCAGAGGAG-3'

3' terminus primers:
PCR-3 (SEQ ID NO: 44):
5'-CTCAGGAGGGGTCGCCACG-3';

PCR-4 (SEQ ID NO: 45):
5'-CTCACCATTCATGTGGCTGGAGAGAAA-3'
```

If the recombinant vector has the correct insertion, there should be only one PCR band. The length of the 5' terminus product should be 2604 bp, and the length of the 3' terminus product should be 3251 bp.

TABLE 5

| The PCR reaction system (20 μL) | |
|---|---|
| 10 × buffer | 2 μL |
| dNTP (2 mM) | 2 μL |
| $MgSO_4$ (25 mM) | 0.8 μL |
| Upstream primer (10 μM) | 0.6 μL |
| Downstream primer (10 μM) | 0.6 μL |
| Mouse tail gDNA | 200 ng |
| KOD-Plus- (1 U/μL) | 0.6 μL |

TABLE 6

| The PCR reaction conditions | | |
|---|---|---|
| Temperature | Time | Cycle |
| 94° C. | 5 min | 1 |
| 94° C. | 30 sec | 15 |
| 67° C. (−0.7° C./cycle) | 30 sec | |
| 68° C. | 1 kb/min | |
| 94° C. | 30 sec | 25 |
| 56° C. | 30 sec | |
| 68° C. | 1 kb/min | |
| 68° C. | 10 min | 1 |
| 4° C. | 10 min | 1 |

Figures 7A, 7B:
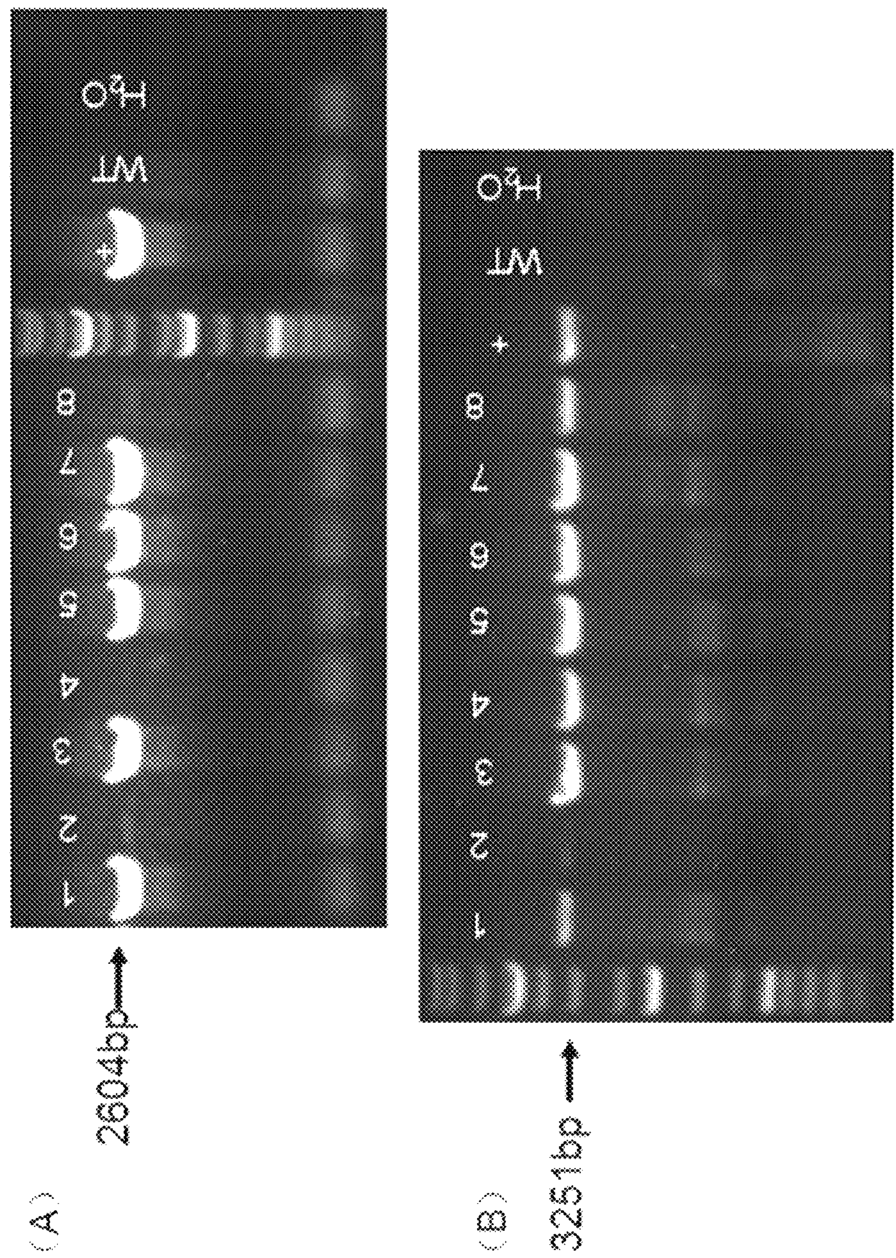
FIGS. 7A-7B show PCR identification result of samples from mouse tails (WT is wild type, mice with No. 1, 3, 5, 6 and 7 are positive mice).

Among the 8 mice, 5 of them were identified as positive mice. The identification number for these mice are 1, 3, 5, 6 and 7. The identification results are provided in FIG. 7.

Furthermore, these 5 mice were further examined by Southern blotting to determine whether they had a random insertion. The genomic DNA was extracted from the mouse tail, and BamH and NcoI were used to digest the genomic DNA, the digestion products were transferred to membrane and hybridized. The probes P1 and P2 were located respectively on the outside of the 5' homologous arm and the humanized fragment. The primers for probe synthesis are as follows:

```
P1-F (SEQ ID NO: 46):
5'-tcttccctgcagtttttaggggcag-3'

P1-R (SEQ ID NO: 47):
5'-agtccccagtcctctcatggaaaca-3'

P2-F (SEQ ID NO: 48):
5'-gtgagcgagtttactcagttggcct-3'

P2-R (SEQ ID NO: 49):
5'-ctagtgccagtcacagactcacagc-3'
```

The genetically engineered mice should have the 18.1 kb or 7.2 kb band with probe hybridization; whereas the wild type C56BL/6 mice would have the 12.2 kb or 8.2 kb band, and no hybrid band should be generated.

Figure 8:
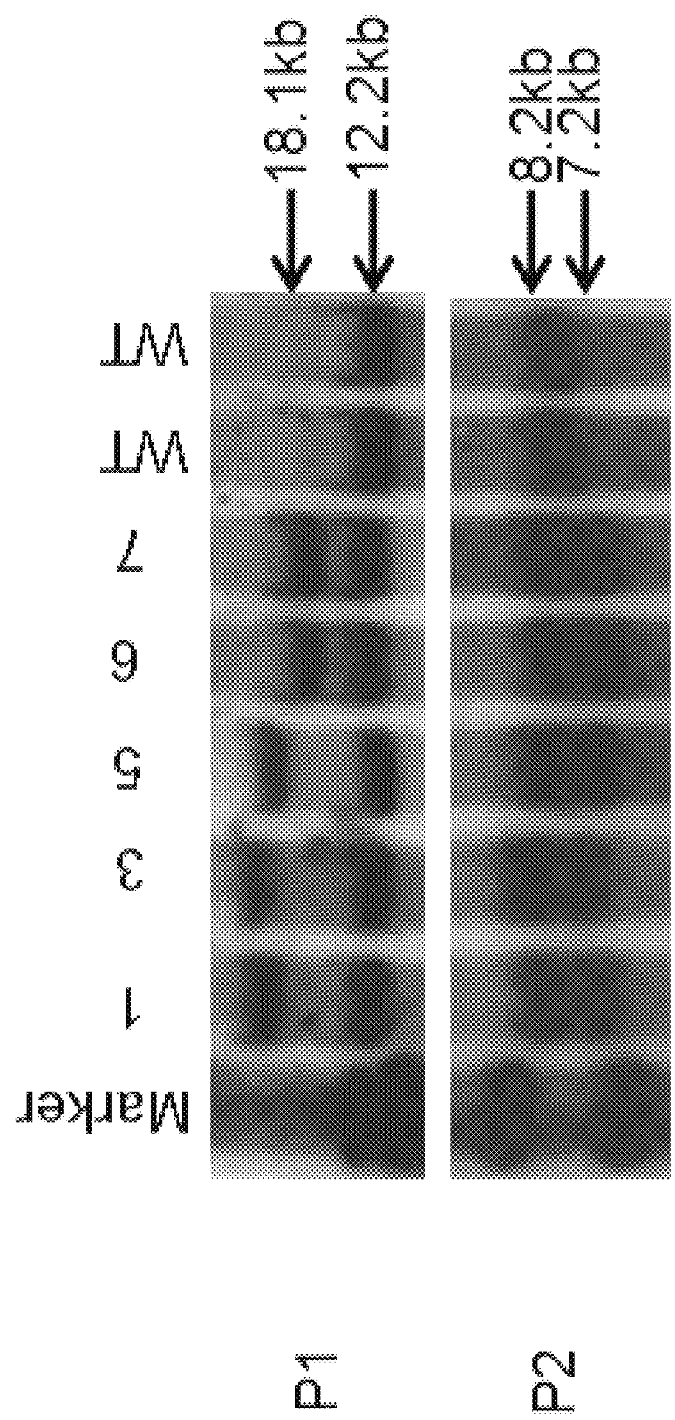
FIG. 8 shows Southern blot results for F1 generation mice (M is the maker; WT is wild type; mice with No. 6 and 7 have no random insertion).

The results showed that the bands were consistent with the expected results. It was confirmed that the 2 mice were positive hybrids that did not have random insertions. They were the mice with identification number 6 and 7. Southern blot results are shown in FIG. 8.

It thus shows that this method can be used to construct humanized B-hOX40 mice that have no random insertion.

2. Protein Identification

One of the humanized mice identified by PCR was selected for the study. One wild type C57BL/6 mouse was used as the control. 15 μg of CD3 were injected intraperitoneally to the mice, and in 24 h 15 μg of CD3 were further injected intraperitoneally to the mice. The spleens were collected at the end of 39 h, and the spleen samples were grinded. The ground samples were then passed through 70 μm cell mesh, the filtered cell suspensions were centrifuged and the supernatants were discarded; the erythrocyte lysis solution was added for lysis of 5 min, and then PBS solution was added to neutralize the lysis reaction. The solution was centrifuged again and the supernatants were discarded. The cells were washed once with PBS.

Figures 9A, 9B, 9C, 9D, 9E:
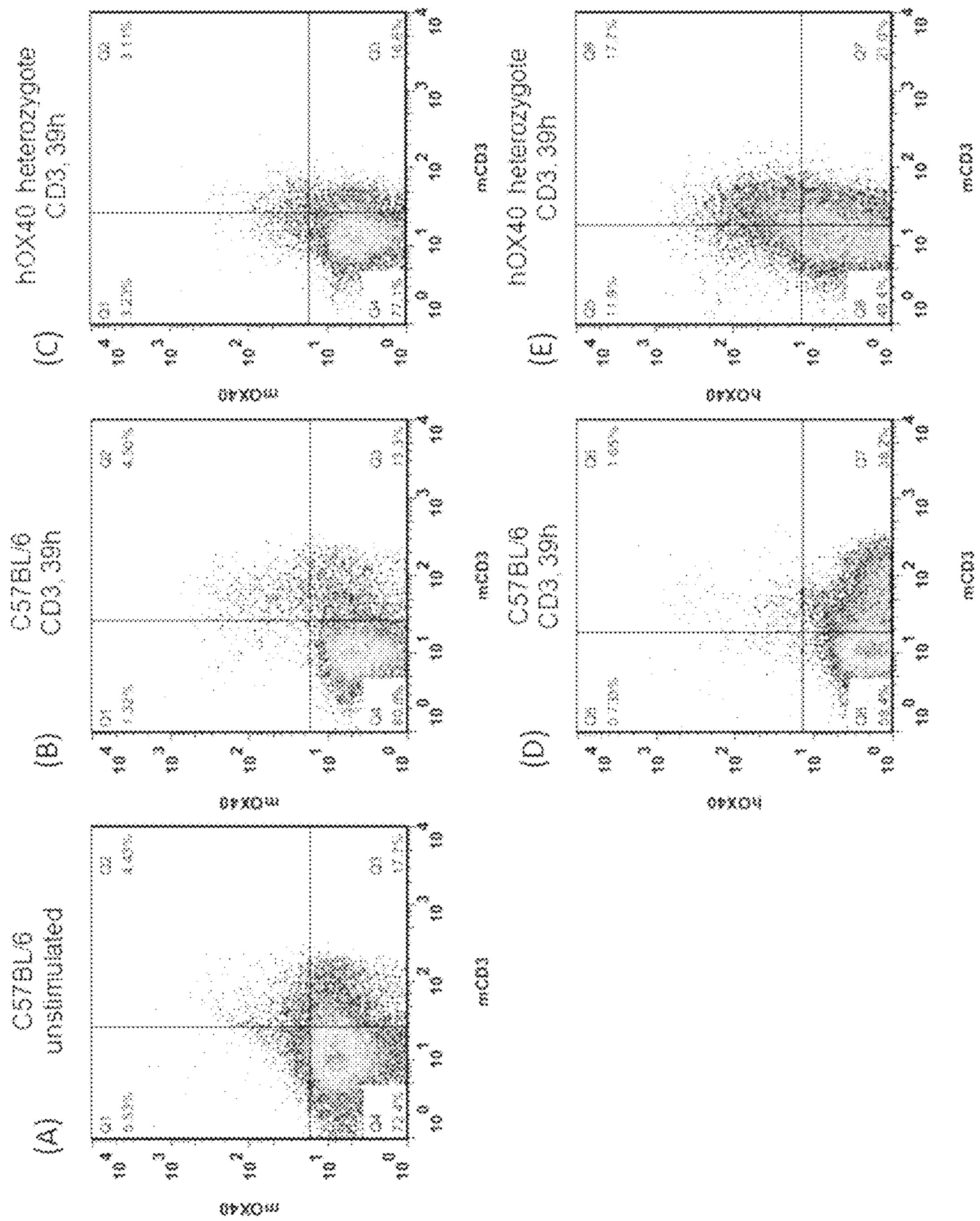
FIG. 9 shows flow cytometry analysis results for C57BL/6 mice and OX40 humanized mice. The anti-mouse CD3 antibody was used to stimulate the T cell activation in the spleen, and then anti-mouse (FIGS. 9B and 9C) and anti-human (FIGS. 9D and 9E) OX40 antibodies with fluorescent labels were used, which were then detected in the flow cytometry analysis. Compared to the control group, the cells with the expression of human OX40 protein can be detected in the spleen of OX40 humanized F1 hybrids; whereas in the spleen of C57BL/6 mice, no cells expressing human OX40 protein were detected.

Anti-mCD3 antibodies were used for staining extracellular proteins, and anti-hOX40 antibodies were used for staining extracellular proteins. The cells were washed once again with PBS. Flow cytometry was carried out to detect protein expression. Flow cytometry analysis results (FIG. 9) show when compared with the C57BL/6 mice with or without the stimulation of CD3 antibody for T cell activation in spleen, the humanized mouse spleen has the cells of human OX40 protein expression as detected by anti-human OX40 antibody, while the spleen of the C57BL/6 control mice does not have detectable cells of human OX40 protein expression. The foregoing results indicate that the OX40 genetically modified humanized mouse is able to express human OX40 protein, which can be detected by an anti-human antibody. The model mice will be useful for screening and detection of anti-human OX40 antibodies.

The B-hOX40 humanized genetically engineered homozygous mice were obtained by mating the previously obtained heterozygous mice with each other. One homozygous B-hOX40 mouse (4-6 weeks old) was selected, and two wild type C57BL/6 mouse were selected as a control. 7.5 μs of mouse CD3 antibody was injected intraperitoneally to the mice, and the spleens of the mice were collected after 24 h. The spleen samples were ground and then filtered through a 70 μm cell filter, the obtained cell suspensions were centrifuged and the resulting supernatants were discarded. The cell samples were added with erythrocyte lysis solution for lysis of 5 min, and then added PBS solution to neutralize the lysis reaction, centrifuged again and the supernatants were discarded, the cells were washed once with PBS. The obtained samples were used in FACS detection and RT-PCR detection.

Figures 10A, 10B, 10C, 10D, 10E, 10F:
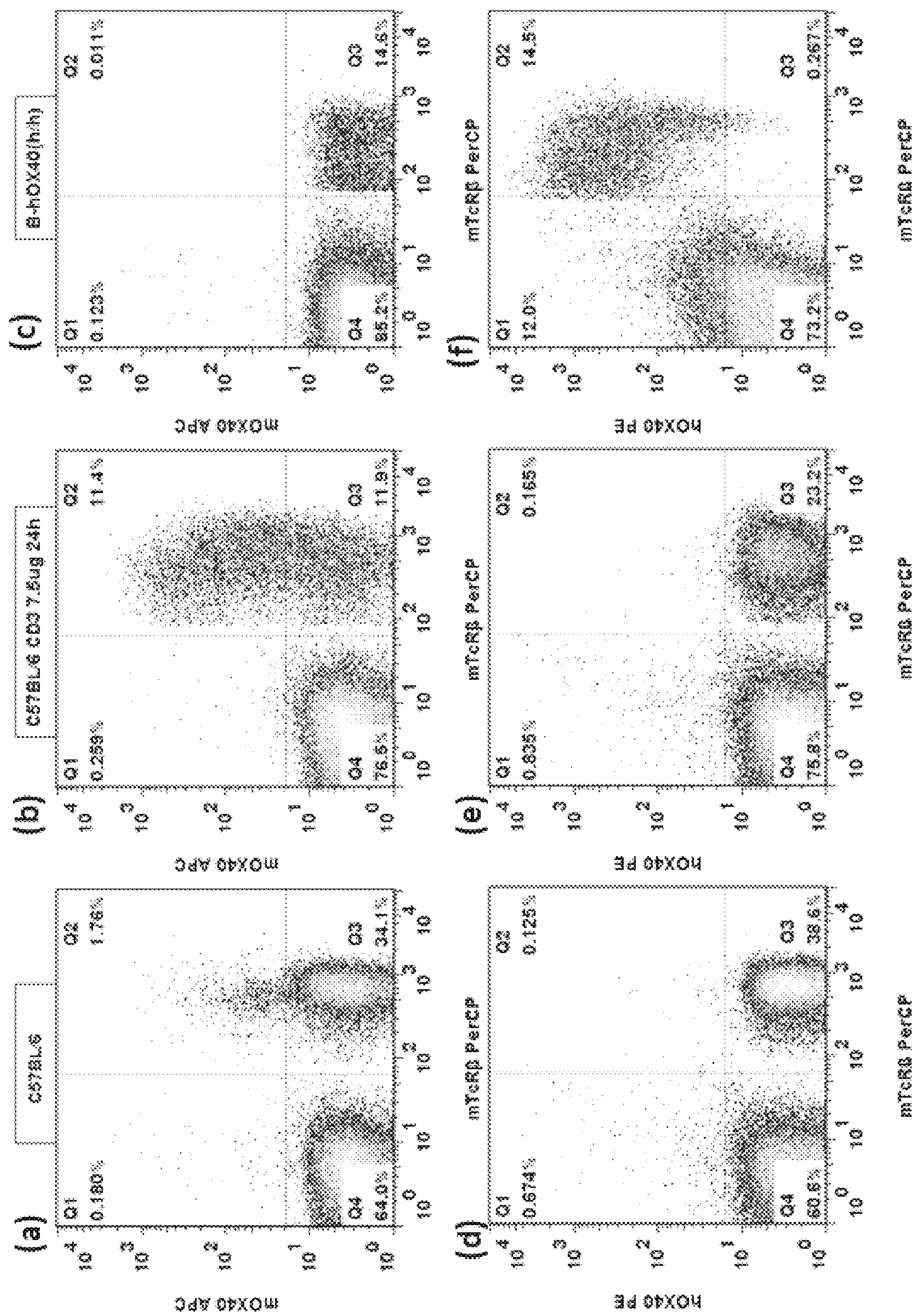
FIGS. 10A-10F show flow cytometry analysis results for two wild type C57BL/6 mice and a B-hOX40 homozygous mouse, which were respectively stimulated by anti-mouse CD3 antibody to stimulate T cell activation in their spleens, and then anti-mouse OX40 antibody mOX40 APC (FIGS. 10A, 10B, 10C) and anti-human OX40 antibody hOX40 PE (FIGS. 10D, 10E, 10F) were used for cell labeling. Compared to the control group (FIGS. 10A, 10D), the cells with the expression of human OX40 protein can be detected in the spleens of B-hOX40 homozygous mouse (FIG. 10F); whereas in the spleen of C57BL/6 mouse, no cells expressing human OX40 protein were detected (FIGS. 10D and 10E).

FACS detection: The T cells extracellular proteins were simultaneously stained with mouse OX40 antibody mOX40 APC and mouse T cell surface antibody mTcRβ, as well as human OX40 antibody hOX40PE and mouse T cell surface antibody mTcRβ; the cells were then washed with PBS and then detected for protein expression by FACS detection. Flow cytometry analysis results are shown in FIG. 10, when compared with the C57BL/6 mice with or without the stimulation of CD3 antibody for T cell activation in spleen, the mouse OX40 antibody was able to detect the cells expressing mouse OX40 protein in the spleen samples from the C57BL/6 control mice (FIG. 10B); while the mouse OX40 antibody was unable to detect the cells expressing mouse OX40 protein in the spleen samples from B-hOX40 homozygote (FIG. 10C). Moreover, the human OX40 antibody was able to detect the cells expressing human OX40 protein in the spleen samples from B-hOX40 homozygote (FIG. 10F); while the human OX40 antibody was unable to detect the cells expressing human OX40 protein in the spleen samples from the C57BL/6 control mice (FIG. 10E).

RT-PCR detection: total RNA was extracted from the spleen cells of B-hOX40 homozygotes, and cDNA were then obtained by reverse transcription using a reverse transcription kit.

Primers for mOX40 RT-PCR:

mOX40 RT-PCR F4: 5'-GTCATCCGTGTGAGACTGGC-3' (SEQ ID NO:50), and mOX40 RT-PCR R4: 5'-CCAGACTGTGGTGGATTGGA-3' (SEQ ID NO:51) were used to amplify mouse OX40 fragment of 401 bp.

Primers for hOX40 RT-PCR:

hOX40 RT-PCR F1: 5'-GCCCTGCACGTGGTGTAACC-3' (SEQ ID NO:52), and hOX40 RT-PCR R1: 5'-ACAGTGATGGGCCTGGCCGG-3' (SEQ ID NO:53) were used amplify human OX40 fragment of 321 bp.

PCR reaction system was 20 μL, reaction conditions: 95° C., 5 min; (95° C., 30 sec; 60° C., 30 sec; 72° C., 30 sec, 35 cycles); 72° C., 10 min; and 4° C. GAPDH was used as an internal reference.

Figure 11:
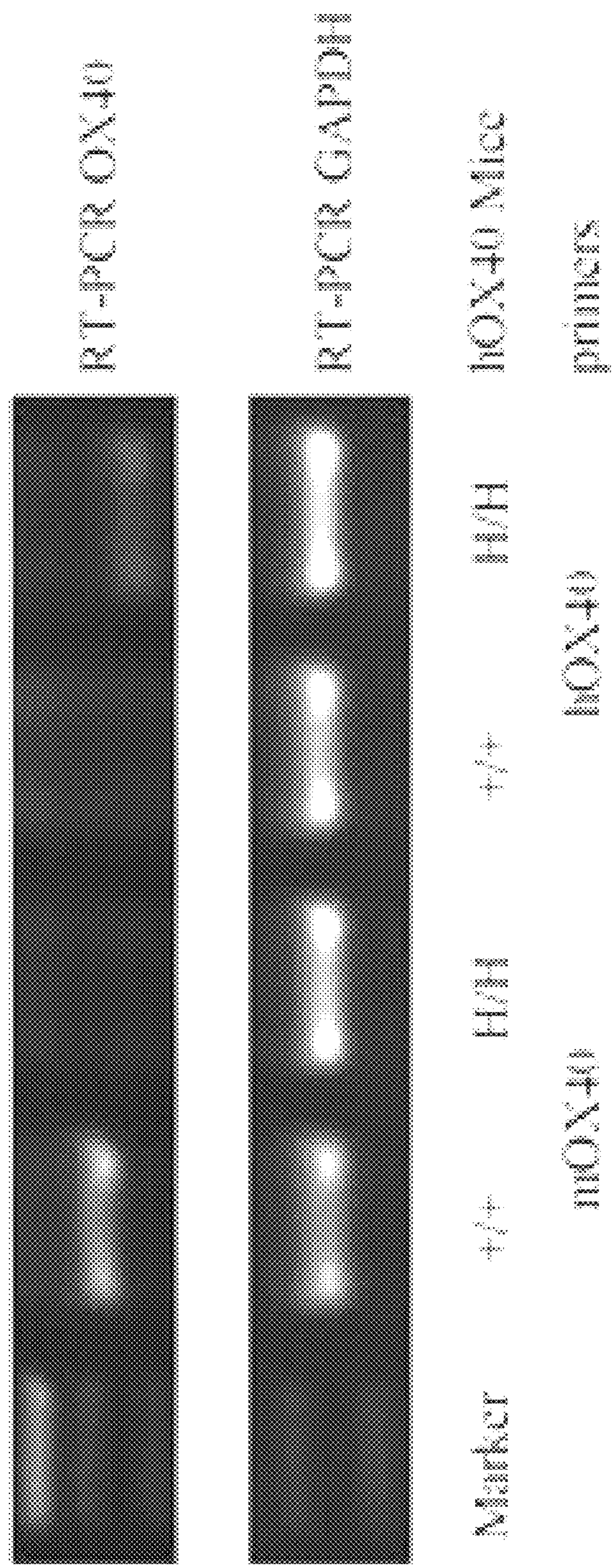
FIG. 11 shows RT-PCR detection results, wherein +/+ is wild type C57BL/6 mouse; H/H is B-hOX40 homozygous mouse; and GAPDH is an internal control.

The results are shown in FIG. 11. The mRNA expression of mouse OX40 could be detected in the activated cells of wild-type C57BL/6 mice; while the mRNA expression of human OX40 could be detected in the activated cells of the B-hOX40 homozygous mouse.

Example 6 Anti-Human OX40 Antibody In Vivo Efficacy Verification

Mice containing humanized OX40 gene (for example, the B-hOX40 mice prepared by the methods described herein) were injected subcutaneously on right body side with $5\times10^5$ mice colon cancer cell MC38. When the tumor volume has reached about 100 $mm^3$, the mice were randomly divided into control group and treatment group (n=5 animals/group). The control group (G1) was injected with blank solvent in an equal volume. The treatment group (G2) was intraperitoneally injected with 3 mg/kg of anti-human OX40 antibody (OX40 agonist full human Ab), the injections were administered on day 0, 3, 6, 9, 12 and 15. The tumor volume was measured twice a week and the body weight was measured for each mouse. Moreover, euthanasia was performed when the tumor volume of a single mouse reached 3000 $mm^3$.

Figure 12:
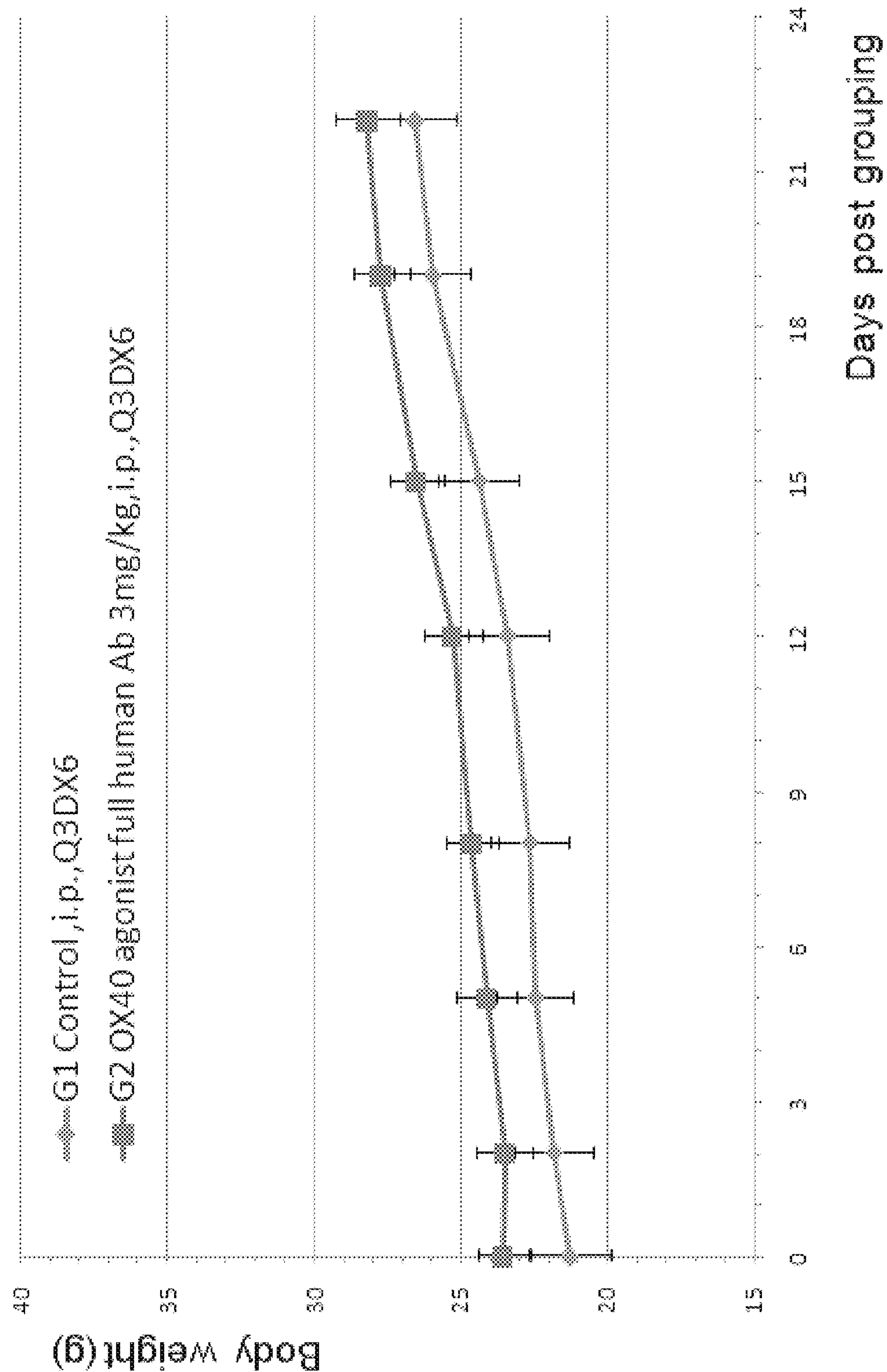
FIG. 12. Mouse colon cancer cells MC38 were injected into B-hOX40 mice and antitumor efficacy studies were performed using anti-human OX40 antibody (OX40 agonist full human Ab). There was no significant difference in average weight gain between the control group and the treatment group.
Figure 13:
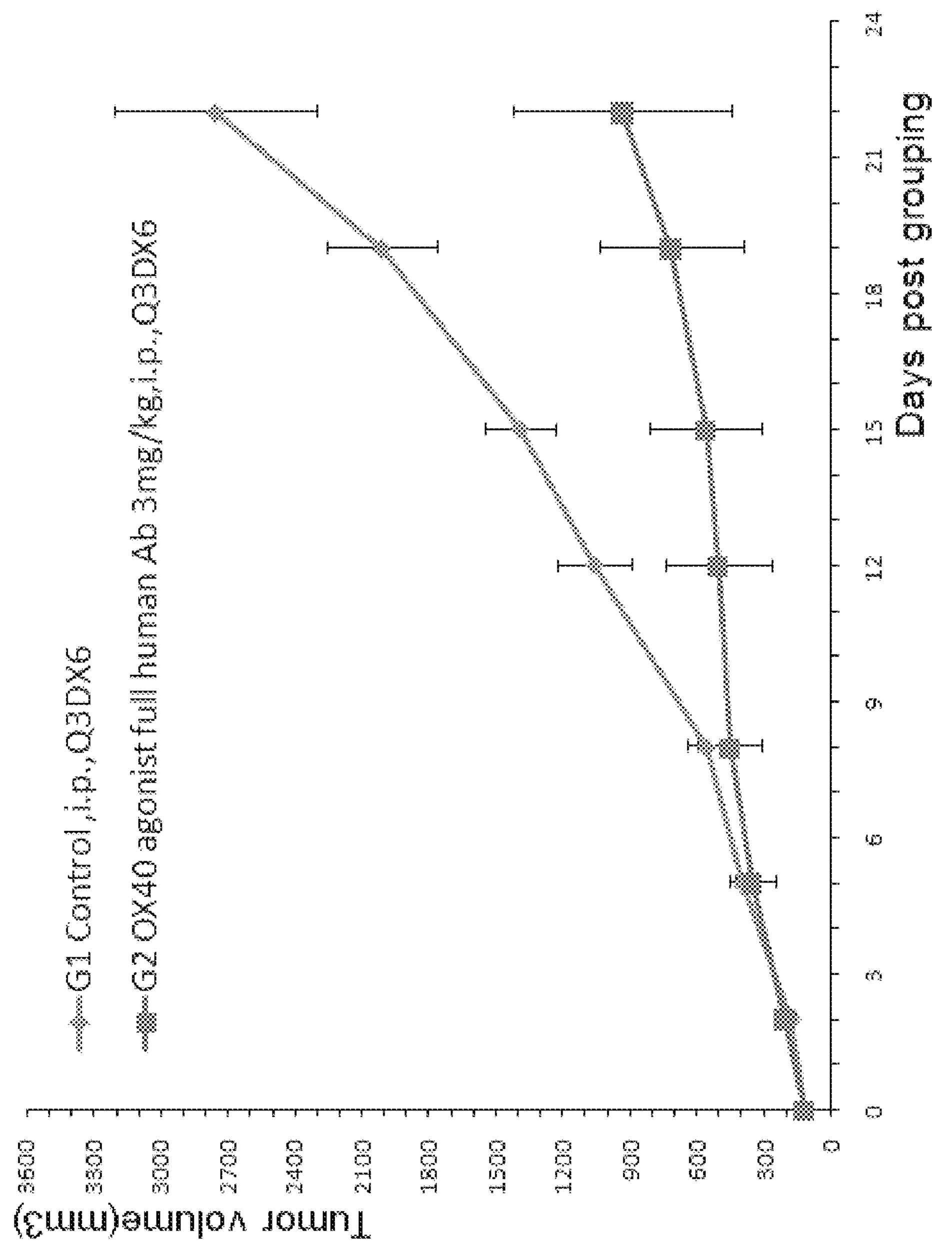
FIG. 13. Mouse colon cancer cells MC38 were injected into B-hOX40 mice and antitumor efficacy studies were performed using anti-human OX40 antibody (OX40 agonist full human Ab). The average volume of tumor in the G2 treatment group was significantly smaller than that in the G1 control group, and the differences were significant.
Figure 14:
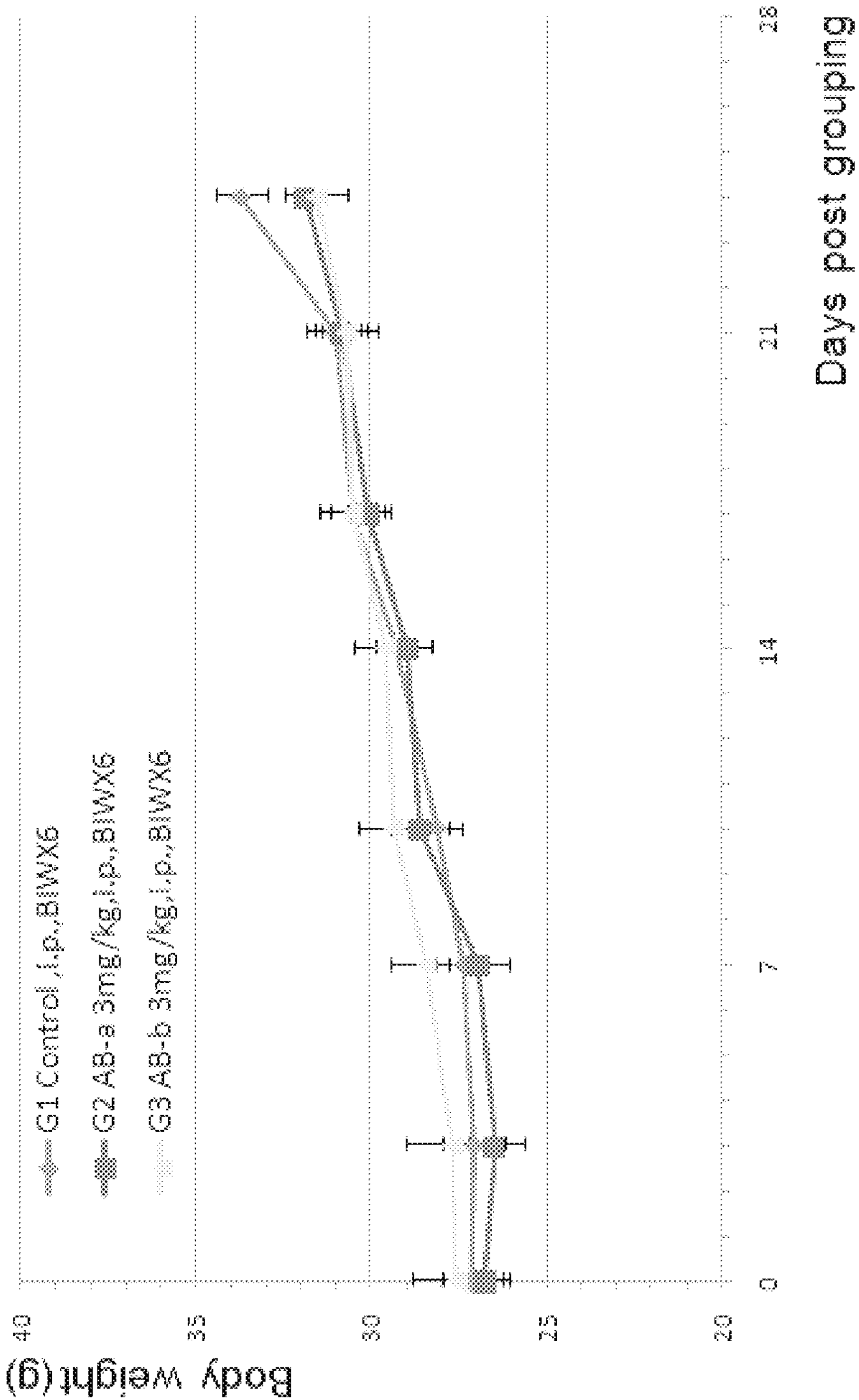
FIG. 14. Mouse colon cancer cells MC38 were injected into B-hOX40 mice. The anti-tumor efficacy test was performed using two anti-human OX40 antibodies Ab-a and Ab-b. There was no significant difference in the average body weight between the G1 control group and the G2 or G3 treatment group.
Figure 15:
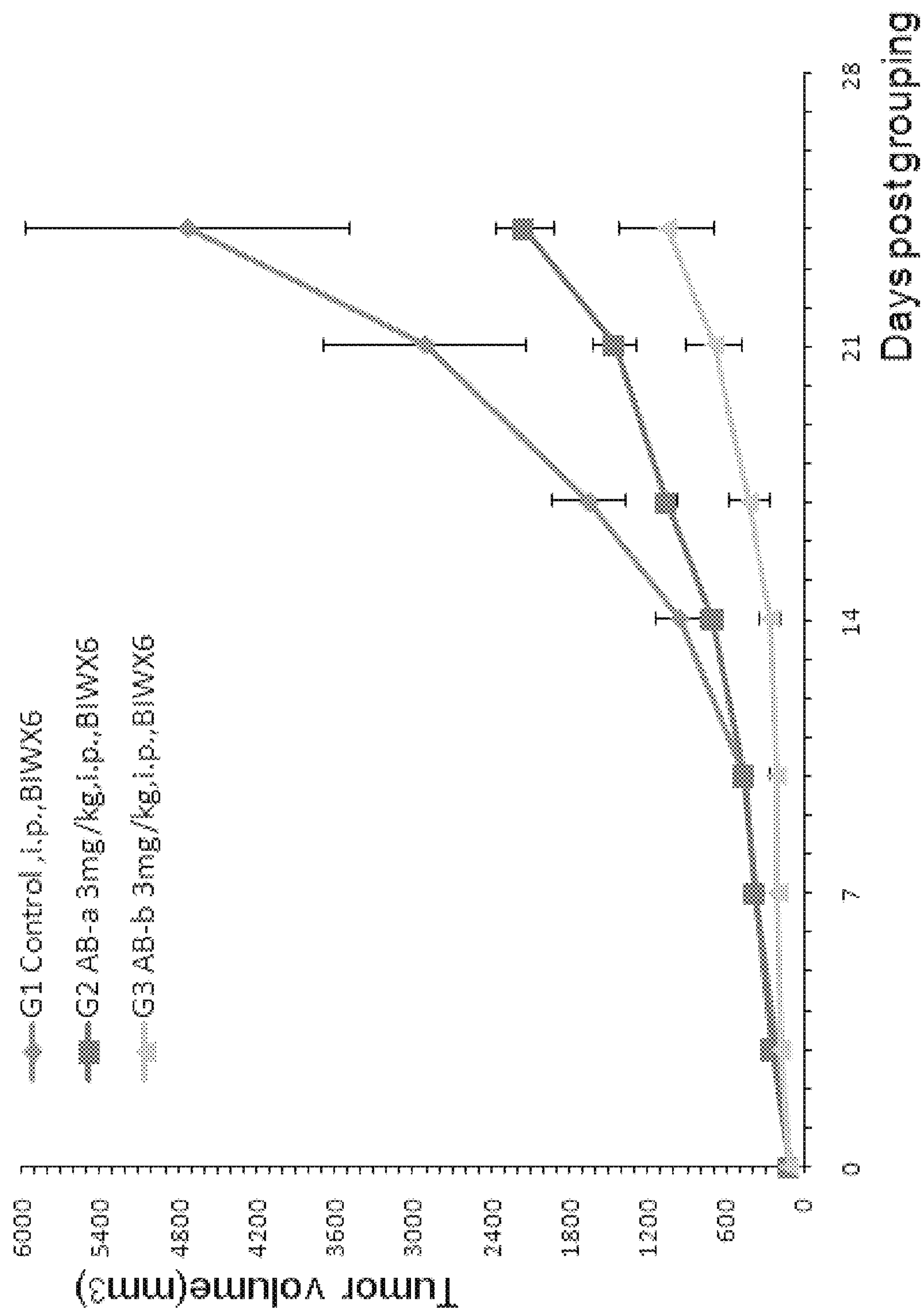
FIG. 15. Mouse colon cancer cells MC38 were injected into B-hOX40 mice. The anti-tumor efficacy test was performed using two anti-human OX40 antibodies Ab-a and Ab-b. The average volume of tumor in the G2 and G3 treatment groups was significantly smaller than that in the G1 control group, and the differences were significant, indicating both Ab-a and Ab-b are effective in inhibiting tumor growth. Furthermore, the average volume of tumor in G2 is significantly larger than the average volume of tumor in G3, indicating that under the same dose regimen, Ab-b is more effective than Ab-a.

Overall, the animals in each group were healthy, and the body weights of all the treatment and control mice did not significantly change throughout the experimental period (FIG. 12). The tumor in the control group continued growing during the experimental period; when compared with the control group mice, the tumor volumes in the treatment group were smaller by a certain degree (FIG. 13). It thus can be determined that the use of anti-human OX40 antibody (OX40 agonist full humanAb) can significantly inhibit the tumor growth in mice.

Table 7 shows the tumor volumes on the day of grouping, 12 days after the grouping, and at the end of experiment (22 days after the grouping), the survival rate of the mice, the tumor (volume) inhibition rate (Tumor Growth Inhibition Value, $TGI_{TV}$), and the statistical differences (P value) in mouse body weights and tumor volume between the treatment and control groups.

TABLE 7

| | Tumor volume ($mm^3$) | | | | | P value | |
|---|---|---|---|---|---|---|---|
| | Day 0 | Day 12 | Day 22 | Survival | $TGI_{TV}$ % | Body weight | Tumor volume |
| Control | 119 ± 47 | 1064 ± 372 | 2754 ± 1009 | 5/5 | N/A | N/A | N/A |
| Treatment | 119 ± 50 | 508 ± 530 | 934 ± 1094 | 5/5 | 69.1 | 0.4 | 0.026 |

All animals in both treatment and control group were alive at the end of the experiments (22 days after the grouping), and had normal weight gain. The body weight between the treatment and control groups were not significantly different (P>0.05), indicating that anti-human OX40 antibodies were well tolerated in the mice. The tumor in the control group continued growing during the experimental period. At the end of the experiment, the average tumor volume in the control group is 2754 $mm^3$; and the average tumor volume in the treatment group is 934 $mm^3$. The tumor volumes in the treatment group were significantly smaller (P<0.05). $TGI_{TV}$ is 69.1%. This example has demonstrated that the anti-human OX40 antibodies can effectively inhibit tumor growth in the the B-hOX40 mouse model ($TGI_{TV}$>60%), and is relatively safe, and well tolerated by the animals.

Example 7. Screening of Anti-Human OX40 Modulators

The examples above have demonstrated that anti-human OX40 antibody (OX40 agonist full human Ab) has a significant inhibitory effect on tumor growth in B-hOX40 mouse model, and thus can be used to assess the efficacy of OX40 drugs in vivo and to assess the treatment efficacy of targeting OX40. This example selected multiple anti-human OX40 antibodies to further verify that B-hOX40 mice can be used as a live substitution model in in vivo studies, which can be used for screening, evaluating and treating with human OX40 signaling pathway modulators.

Similar to the procedure in Example 6, mice with humanized OX40 gene (for example, the B-hOX40 mice prepared by the methods described herein) were injected subcutaneously on right body side with $5\times10^5$ mice colon cancer cell MC38. When the tumor volume has reached about 100 $mm^3$, the mice were randomly divided into control group and treatment group (n=5 animals/group) (day 0). The control group (G1) was injected with blank solvent in an equal volume. The treatment group (G2) was intraperitoneally injected with 3 mg/kg of anti-human OX40 antibody (AB-a), and the treatment group (G3) was intraperitoneally injected with 3 mg/kg of anti-human OX40 antibody (AB-b). The injections were administered on day 0, 3, 7, 10, 14 and 17. The tumor volume was measured twice a week and the body weight was also measured for each mouse. Euthanasia was performed when the tumor volume of the mouse reached 3000 $mm^3$.

TABLE 8

| | | Tumor Volume (mm$^3$) | | | | | P value | |
|---|---|---|---|---|---|---|---|---|
| | | Day 0 | Day 14 | Day 24 | Survival | $TGI_{TV}$% | Body weight | Tumor Volume |
| Control G1 | | 120 ± 25 | 964 ± 423 | 4739 ± 2467 | 5/5 | N/A | N/A | N/A |
| Treatment | G2 (AB-a) | 120 ± 24 | 705 ± 95 | 2150 ± 498 | 5/5 | 56.0 | 0.093 | 0.073 |
| | G3 (AB-b) | 120 ± 27 | 267 ± 180 | 1059 ± 818 | 5/5 | 79.7 | 0.107 | 0.021 |

As shown in Table 8, at the end of the experiment (24 days after the grouping), all mice in both the control group and the treatment group were alive and had normal weight gains. In addition, there was no significant difference in body weight between the treatment group mice and the control group mice (P>0.05), confirming that the animals had good tolerance to the anti-human OX40 antibodies AB-a and AB-b. The foregoing two antibodies are not significantly toxic to the mice, and thus are safe. Moreover, the tumors of all of the control mice were growing continuously during the experimental period. At the end of the experiment, the average tumor volume in the control group was 4739 mm$^3$, the average tumor volume in the treatment group with AB-a antibody (G2) was 2150 mm$^3$, and the average tumor volume in the treatment group with AB-b antibody (G3) was 1059±818 mm$^3$. Hence, the tumor volumes of the mice in each treatment group were significantly smaller than that in the control group, and the differences in tumor volume between treatment group and control group were significant (p<0.05). The $TGI_{TV}$ values were 56.0% and 79.7%, indicating that under the condition of the same dose and frequency, anti-human AB-a and AB-b antibodies have an inhibitory effect on tumor growth ($TGI_{TV}$>60%), but AB-b is more effective than AB-a ($TGI_{TV}$ value: G2<G3). This study demonstrates that B-hOX40 mice can be used in screening modulators targeting human OX40 (e.g., antibodies) and in vivo efficacy testing.

Example 8. Preparation and Identification of Mice with Double Humanized or Multiple Humanized Genes Mice with the humanized OX40 gene (such as the B-hOX40 animal model prepared using the methods as described in the present disclosure) can also be used to prepare a double-humanized or multi-humanized animal model. For example, in Example 4, the fertilized egg cells used in the microinjection and embryo transfer process can be selected from the fertilized egg cells of other genetically modified mice or the fertilized egg cells of B-hOX40 mice, so as to obtain OX40 humanized and other gene modified double or multiple gene modified mouse models.

In addition, the B-hOX40 animal model homozygote or heterozygote can be mated with other genetically modified homozygous or heterozygous animal models, and the progeny is then screened; according to the Mendelian law, there is a chance to obtain the OX40 humanized and other gene modified double genes or multiple genes modified heterozygous animal models, and then the obtained heterozygous can be mated with each other to finally obtain the double genes or multiple genes modified homozygote.

In the case of the generating double humanized OX40/PD-1 mouse, since the mouse OX40 gene and Pd-1 gene are located on different chromosomes, the double humanized OX40/PD-1 mouse was obtained by mating the B-hOX40 heterozygous mouse with B-hPD-1 homozygous mouse.

Figures 16A, 16B, 16C, 16D:
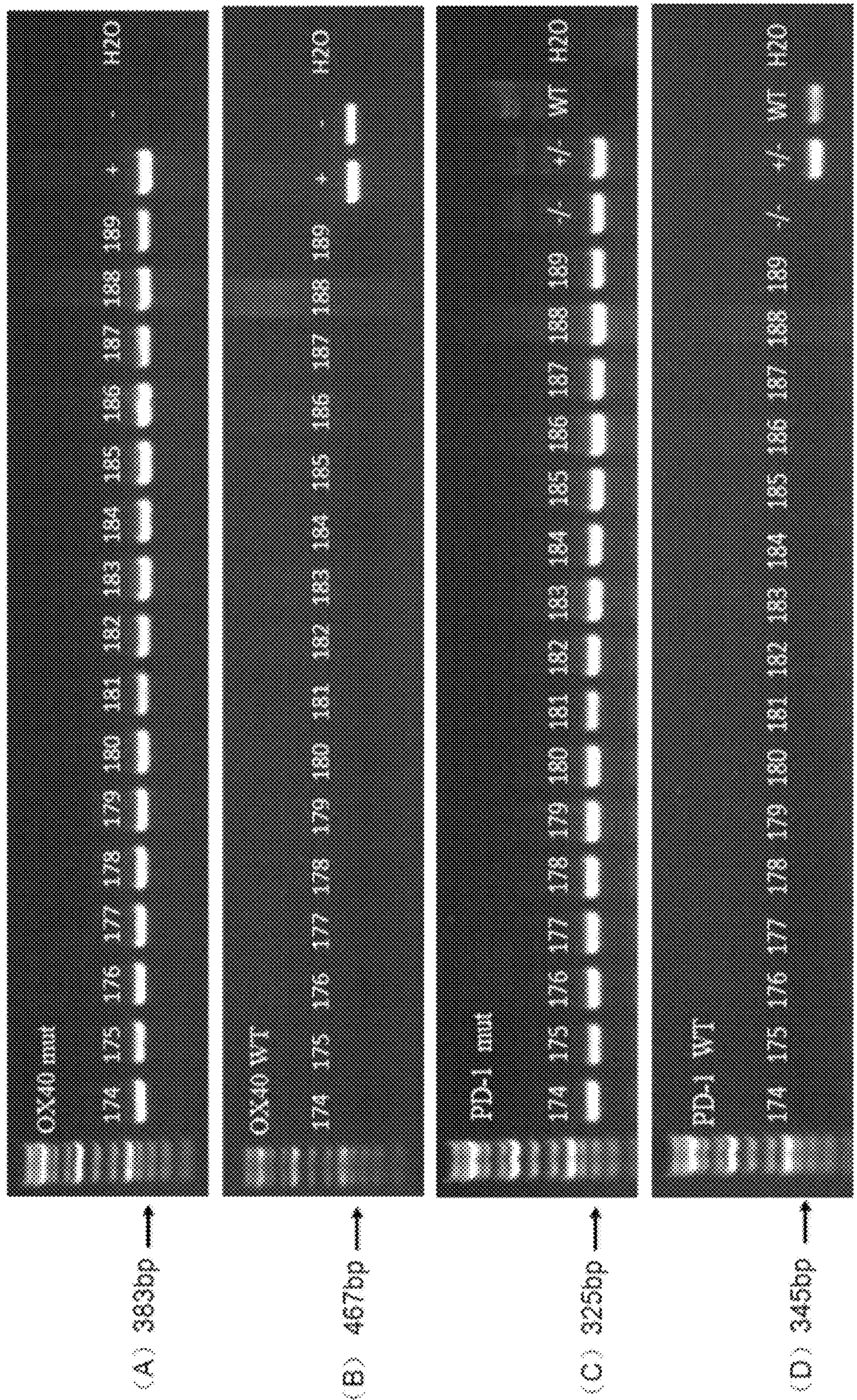
FIGS. 16A-16D. Mouse tail PCR identification result, where + is positive control, – is negative control (FIGS. 16A, 16B); WT is wild type, –/– is humanized PD-1 homozygous mouse, +/– is humanized PD-1 heterozygous mouse (FIGS. 16C, 16D).

PCR analysis was performed on the mouse tail genomic DNA of double humanized OX40/PD-1 mice using four pairs of primers. The specific sequences and product lengths are shown in Table 9. The reaction system and reaction conditions are shown in Table 10 and Table 11. The results for a number of humanized OX40/PD-1 mice are shown in FIG. 16, wherein FIGS. 16A and 16B show that the mice numbered 174-189 were humanized OX40 homozygous mice, FIGS. 16C and 16D show that the mice numbered 174-189 were humanized PD-1 homozygous mice. The results of the two groups indicate that the 16 mice of 174-189 were double gene homozygotes.

TABLE 9

| Primer | Sequence | Product length |
|---|---|---|
| OX40 MUT | F: 5'-tagggtaggggtttgaaagggcaga-3' (SEQ ID NO: 54)<br>R: 5'-cccaggcctaggagaacagcaaatg-3' (SEQ ID NO: 55) | Mut:<br>383 bp |
| OX40WT | F: 5'-gaccctgttatccccaccgcatctc-3' (SEQ ID NO: 56)<br>R: 5'-cccaggcctaggagaacagcaaatg-3' (SEQ ID NO: 55) | WT:<br>467 bp |
| PD-1 MUT | F: 5'-cttccacatgagcgtggtcagggcc-3' (SEQ ID NO: 57)<br>R: 5'-ccaagggactattttagatgggcag-3' (SEQ ID NO: 58) | Mut:<br>325 bp |
| PD-1 WT | F: 5'-gaagctacaagctcctaggtaggggg-3' (SEQ ID NO: 59)<br>R: 5'-acgggttggctcaaaccattaca-3' (SEQ ID NO: 60) | WT:<br>345 bp |

TABLE 10

| PCR reaction system (20 μL) system is shown below: | |
|---|---|
| 2 × Master Mix | 10 μL |
| Upstream primer (10 μM) | 0.5 μL |
| Downstream primer (10 μM) | 0.5 μL |
| Mouse tail genomic DNA | 200 ng |
| KOD-Plus-(1U/μL) | 0.6 μL |
| $ddH_2O$ | Add to 20 μL |

TABLE 11

PCR amplification reaction condition is shown below:

| Temperature | Time | Cycles |
|---|---|---|
| 95° C. | 5 min | 1 |
| 95° C. | 30 sec | 30 |
| 59° C. | 30 sec | |
| 72° C. | 30 sec | |
| 72° C. | 10 min | 1 |
| 4° C. | 10 min | 1 |

Figures 17A, 17B, 17C, 17D, 17E, 17F:
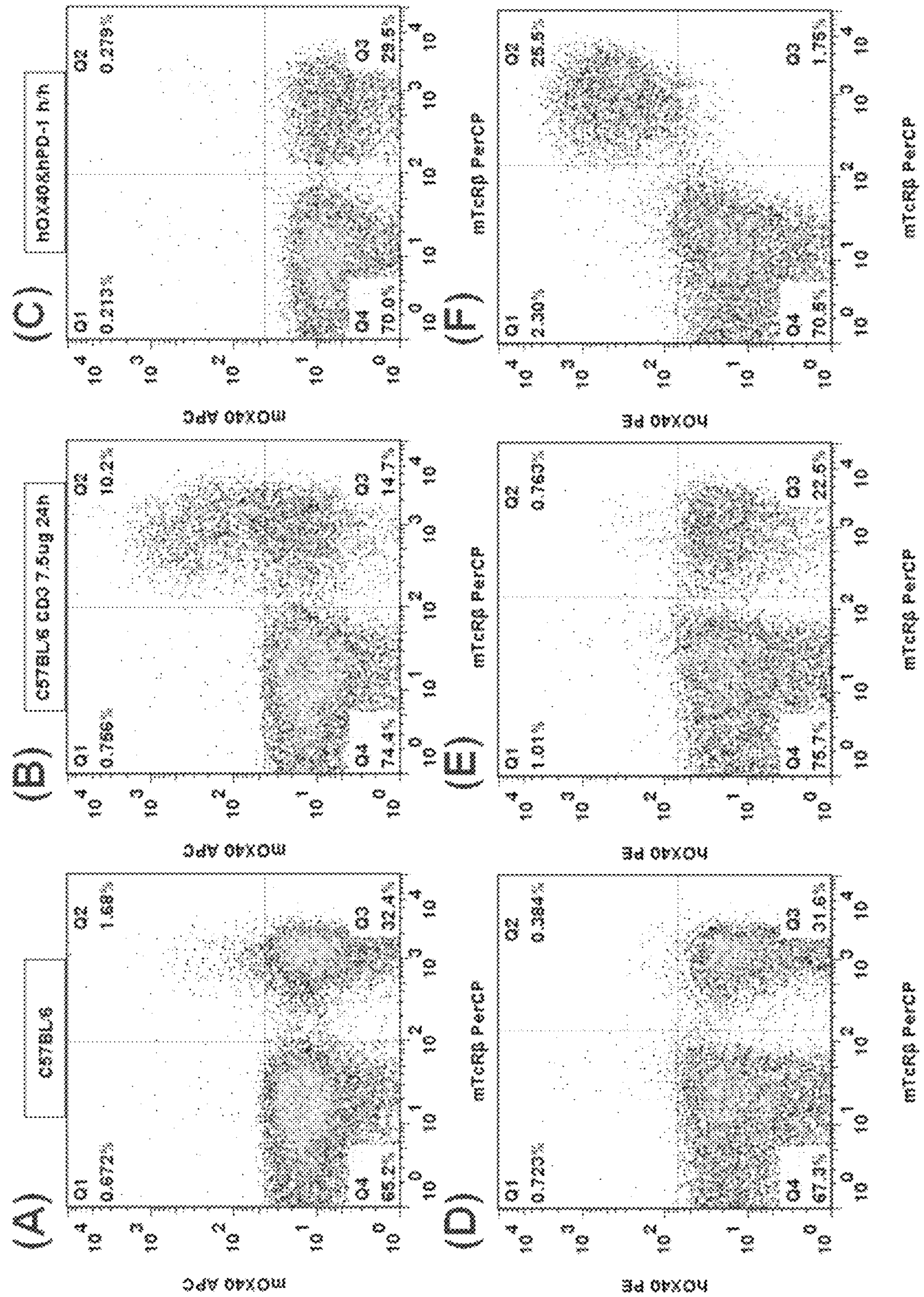
FIGS. 17A-17F show flow cytometry analysis results for C57BL/6 mice and double humanized OX40/PD-1 homozygous mice were used. Anti-mouse CD3 antibody was used to stimulate T cell activation in the spleens of the mice, and then the mouse OX40 antibody mOX40 APC (FIGS. 17A, 17B, 17C), human OX40 antibody hOX40 PE (FIGS. 17D, 17E, 17F), and mouse T cell surface antibody mTcRβ were used to label T cell proteins. The result show that the cells expressing humanized OX40 proteins were detected in the spleens of double humanized OX40/PD-1 mice, while no cells expressing humanized OX40 protein were detected in the spleen of C57BL/6 control mice.
Figures 18A, 18B, 18C, 18D, 18E, 18F:
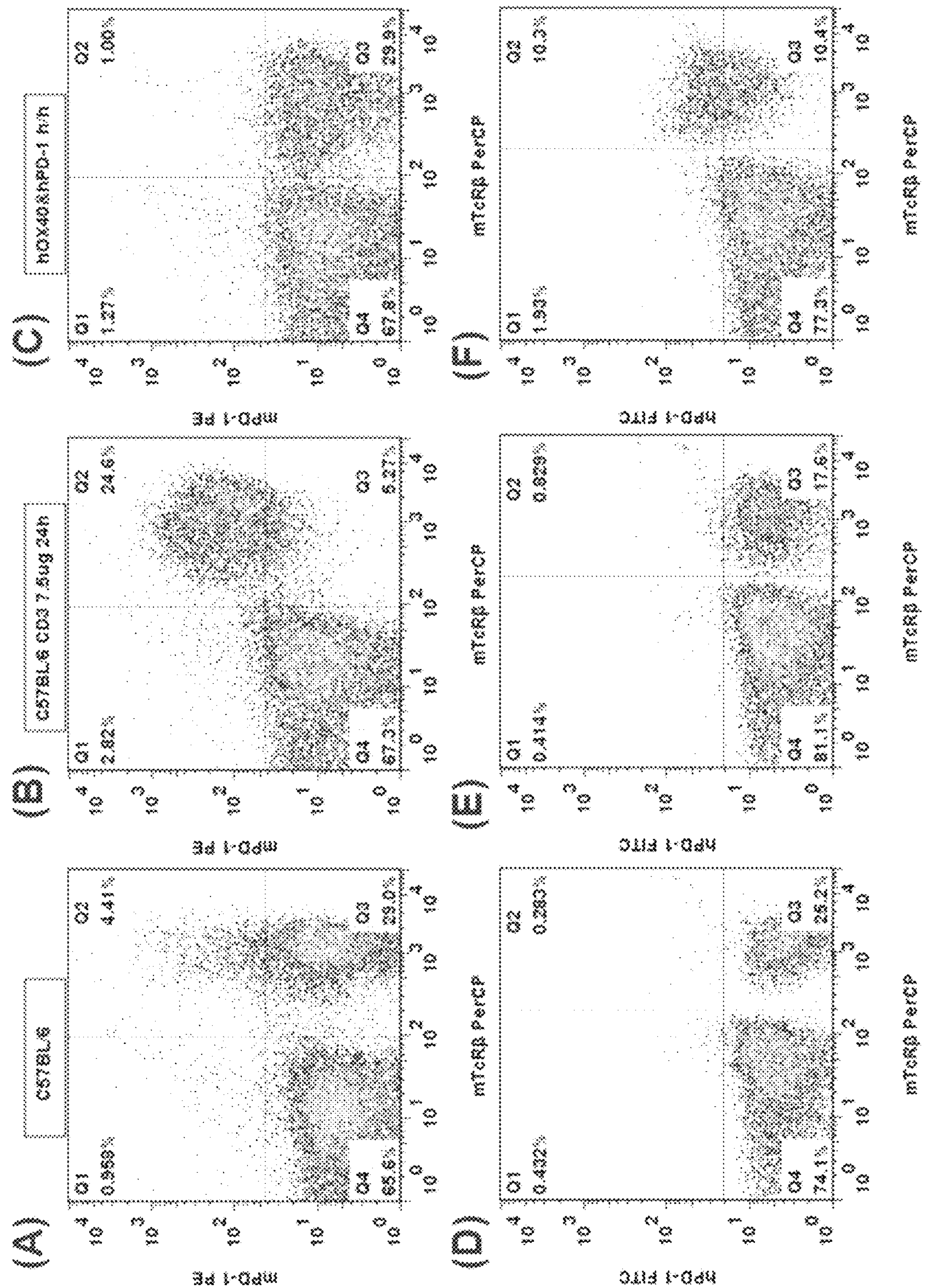
FIGS. 18A-18F show flow cytometry analysis results for C57BL/6 mice and double humanized OX40/PD-1 homozygous mice were used. Anti-mouse CD3 antibody was used to stimulate T cell activation in the spleens of the mice, and then the mouse PD-1 antibody mPD-1 PE (FIGS. 18A, 18B, 18C), human PD-1 antibody hPD-1 FITC (FIGS. 18D, 18E, 18F), and mouse T cell surface antibody mTcRβ were used to label T cell proteins. The result show that the cells expressing humanized PD-1 proteins were detected in the spleens of double humanized OX40/PD-1 mice, while no cells expressing humanized PD-1 protein were detected in the spleen of C57BL/6 control mice.

The expression of the double humanized OX40/PD-1 mice was further examined. A double humanized OX40/PD-1 homozygote (6 weeks old) was selected for the study. Two wild type C57BL/6 mice were selected as control. Mice were injected with 7.5 μg of mouse CD3 antibody intraperitoneally. After 24 hours, the mice were euthanized, and then the spleens of the mice were collected. The spleen samples were ground and the ground samples were filtered through a 70 μm cell mesh. The filtered cell suspensions were centrifuged and the supernatants were discarded; erythrocyte lysis solution was added for lysis for 5 min, and then PBS solution was added to neutralize the lysis reaction. The solution was centrifuged again and the supernatants were discarded, the cells were washed once with PBS. The obtained spleen cell samples were next stained for T cell extracellular protein with the mouse OX40 antibody mOX40APC (FIGS. 17A, 17B, 17C), or human OX40 antibody hOX40 PE (FIGS. 17D, 17E, 17F), or mouse PD-1 antibody mPD-1 PE (FIGS. 18A, 18B, 18C), or human PD-1 antibody hPD-1 FITC (FIGS. 18D, 18E, 18F), and the mouse T cell surface antibody mTcRβ. The cells were subsequently washed with PBS. The protein expressions in the cells were detected by flow cytometry. The results of flow cytometry detection were shown in the figures. Flow cytometry analysis results show when compared with the C57BL/6 mice with or without the stimulation of CD3 antibody for T cell activation in spleen, the human OX40 antibody and human PD-1 antibody can detect the cells expressing human OX40 and PD-1 proteins in the spleen of humanized OX40/PD-1 homozygous mice; whereas in the spleen of the control C57BL/6 mice, no cells expressing human OX40 or PD-1 protein were detected in the control mice.

Example 9. Identification of Gene Knockout Mice

Since the cleavage of Cas9 results in DNA double strands break, and the homologous recombination repair may result in insertion/deletion mutations, it is possible to obtain OX40 knockout mouse while preparing the humanized OX40 mouse. A pair of primers was thus designed. They are located on the left side of the 5' end target site, and to the right side of the 3' end target site, which are shown as follows:

```
                                        (SEQ ID NO: 61)
5'-CCCAGACTCCTGTGAAGGCAGAAAG-3'

                                        (SEQ ID NO: 62)
5'-AGGAGGTAGGCTTTACTGAGCCCAA-3'
```

Figure 19:
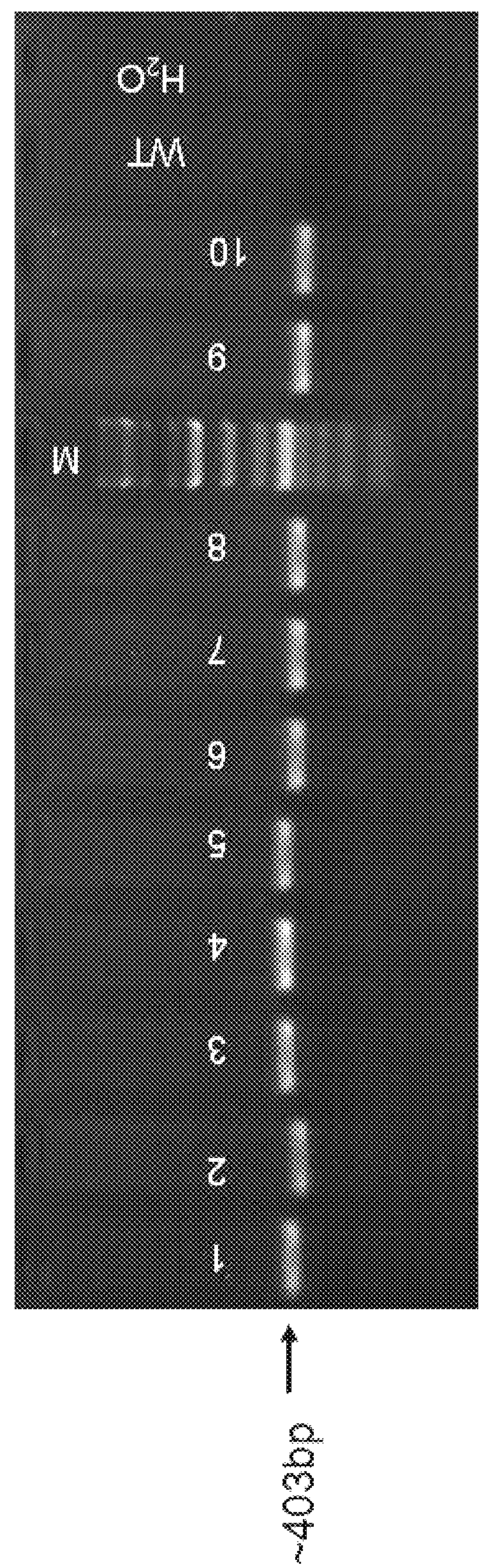
FIG. 19 shows PCR identification results for OX40 gene knockout mice, wherein WT is wild type, M is the maker, the mice with no. 1-10 are OX40 knockout mice.

The PRC reaction systems and conditions are listed in Table 10 and Table 11. Under this condition, the knock-out mice should have only one PCR band, and the product length should be about 403 bp. The wildtype does not have any PCR band. The results are shown in FIG. 19. The mice with identification number 1-10 are OX40 knockout mice.

Example 10. Preparation Method Based on Embryonic Stem Cells

Figure 20:
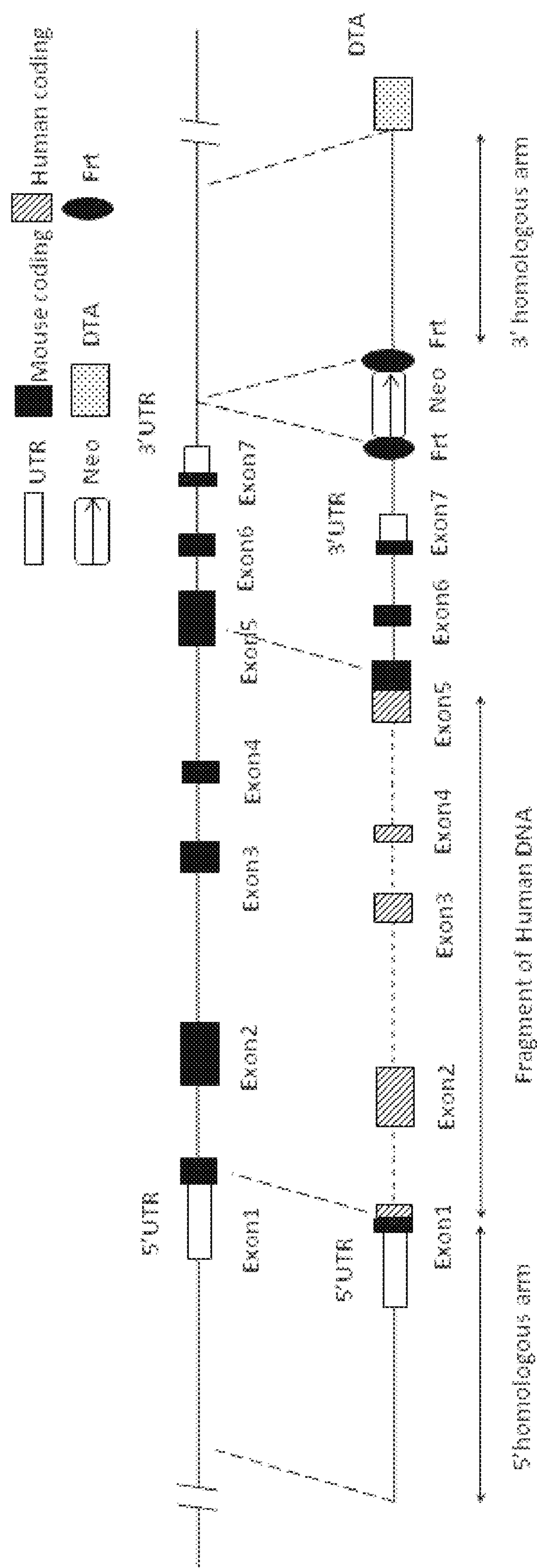
FIG. 20 is a schematic diagram of the targeting strategy for embryonic stem cells.

The non-human mammals can also be prepared through other gene editing systems and approaches, which includes, but is not limited to, gene homologous recombination techniques based on embryonic stem cells (ES), zinc finger nuclease (ZFN) techniques, transcriptional activator-like effector factor nuclease (TALEN) technique, homing endonuclease (megakable base ribozyme), or other molecular biology techniques. In this example, the conventional ES cell gene homologous recombination technique is used as an example to describe how to obtain a OX40 gene humanized mouse by other methods. According to the gene editing strategy of the methods described herein and the humanized mouse OX40 gene map (FIG. 4), a targeting strategy has been developed as shown in FIG. 20. FIG. 20 shows the design of the recombinant vector. In view of the fact that one of the objects is to replace the exons 1-5 of the mouse OX40 gene in whole or in part with the human OX40 gene fragment, a recombinant vector that contains a 5' homologous arm (4131 bp), a 3' homologous arm (5472 bp) and a humanized gene fragment (2041 bp) is also designed. The vector can also contain a resistance gene for positive clone screening, such as neomycin phosphotransferase coding sequence Neo. On both sides of the resistance gene, two site-specific recombination systems in the same orientation, such as Frt or LoxP, can be added. Furthermore, a coding gene with a negative screening marker, such as the diphtheria toxin A subunit coding gene (DTA), can be constructed downstream of the recombinant vector 3' homologous arm. Vector construction can be carried out using methods known in the art, such as enzyme digestion and so on. The recombinant vector with correct sequence can be next transfected into mouse embryonic stem cells, such as C57BL/6 mouse embryonic stem cells, and then the recombinant vector can be screened by positive clone screening gene. The cells transfected with the recombinant vector are next screened by using the positive clone marker gene, and Southern Blot technique can be used for DNA recombination identification. For the selected correct positive clones, the positive clonal cells (black mice) are injected into the isolated blastocysts (white mice) by microinjection according to the method described in the book A. Nagy, et al., "Manipulating the Mouse Embryo: A Laboratory Manual (Third Edition)," Cold Spring Harbor Laboratory Press, 2003. The resulting chimeric blastocysts formed following the injection are transferred to the culture medium for a short time culture and then transplanted into the fallopian tubes of the recipient mice (white mice) to produce F0 generation chimeric mice (black and white). The F0 generation chimeric mice with correct gene recombination are then selected by extracting the mouse tail genome and detecting by PCR for subsequent breeding and identification. The F1 generation mice are obtained by mating the F0 generation chimeric mice with wild type mice. Stable gene recombination positive F1 heterozygous mice are selected by extracting rat tail genome and PCR detection. Next, the F1 heterozygous mice are mated to each other to obtain genetically recombinant positive F2 generation homozygous mice. In addition, the F1 heterozygous mice can also be mated with Flp or Cre mice to remove the positive clone screening marker gene (neo, etc.), and then the OX40 gene humanized homozygous mice can be obtained by mating these mice with each other. The methods of genotyping and phenotypic detection of the obtained F1 heterozygous mice or F2 homozygous mice are similar to those used in Example 5 described above.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for making a genetically-modified mouse, comprising:

(1) replacing in a fertilized egg or an embryonic stem cell, at an endogenous OX40 gene locus, a nucleic acid sequence encoding a portion of the extracellular region of an endogenous OX40 protein with a nucleic acid sequence encoding a portion of an extracellular region of a human OX40 protein, wherein the replaced nucleic acid sequence comprises a portion of exon 1, exons 2-4 and a portion of exon 5 of the endogenous OX40 gene;

(2) transplanting the fertilized egg obtained in step (1) into the oviduct of a pseudopregnant female mouse or transplanting the embryonic stem cell obtained in step (1) into a blastocyst which is then transplanted into the oviduct of a pseudopregnant female mouse to obtain a child mouse; and (3) mating the child mouse obtained in step (2) to obtain a homozygote mouse, wherein the homozygote mouse detectably expresses a humanized OX40 protein comprising a humanized OX40 extracellular region and an endogenous OX40 cytoplasmic region on the surface of activated T cells, wherein the humanized OX40 protein comprises SEQ ID NO: 32.

2. The method of claim 1, wherein the sequence encoding the humanized OX40 protein is operably linked to an endogenous regulatory element at the endogenous OX40 gene locus.

3. The method of claim 1, wherein the genetically-modified mouse does not express the endogenous OX40 protein.

4. The method of claim 1, wherein an anti-human OX40 antibody can bind to the humanized OX40 protein expressed in the mouse and increase immune response in the mouse.

5. The method of claim 1, wherein the mouse can be used to test effectiveness of an anti-human OX40 antibody for treating cancer.

6. A method for making a genetically-modified mouse, comprising:

(1) providing a plasmid comprising a human OX40 gene fragment, flanked by a 5' homology arm and a 3' homology arm, wherein the 5' and 3' homology arms target an endogenous OX40 gene;

(2) providing two small guide RNAs (sgRNAs) that target the endogenous OX40 gene;

(3) modifying genome of a fertilized egg or an embryonic stem cell by using the plasmid of step (1), the sgRNAs of step (2), and Cas9; and (4) transplanting the fertilized egg obtained in step (3) into the oviduct of a pseudopregnant female mouse or transplanting the embryonic stem cell obtained in step (3) into a blastocyst which is then transplanted into the oviduct of a pseudopregnant female mouse to produce a child mouse that functionally expresses a humanized OX40 protein, (5) mating the child mouse obtained in step (2) to obtain a homozygote mouse, wherein the fertilized egg is modified by CRISPR with sgRNAs that target a 5'-terminal targeting site selected from the group consisting of SEQ ID NOS: 1-7 and a 3'-terminal targeting site selected from the group consisting of SEQ ID NOS: 8-15, and the humanized OX40 protein comprises SEQ ID NO: 32.

7. The method of claim 6, wherein the 5'-terminal targeting site is SEQ ID NO: 1 and the 3'-terminal targeting site is SEQ ID NO: 11.

8. The method of claim 6, wherein the sequence encoding the humanized OX40 protein is operably linked to an endogenous regulatory element at the endogenous OX40 gene locus.

9. The method of claim 6, wherein the genetically-modified mouse does not express an endogenous OX40 protein.

10. The method of claim 6, wherein an anti-human OX40 antibody can bind to the humanized OX40 protein expressed in the mouse and increase immune response in the mouse.

11. The method of claim 6, wherein the mouse can be used to test effectiveness of an anti-human OX40 antibody for treating cancer.

* * * * *

UNITED STATES PATENT AND TRADEMARK OFFICE
CERTIFICATE OF CORRECTION

PATENT NO. : 11,279,948 B2
APPLICATION NO. : 16/329269
DATED : March 22, 2022
INVENTOR(S) : Yuelei Shen et al.

It is certified that error appears in the above-identified patent and that said Letters Patent is hereby corrected as shown below:

In the Specification

In Column 1, Line 7, after "application" insert -- is a National Stage application under 35 U.S.C. § 371 of International Application No. PCT/CN2017/099575, filed on August 30, 2017, which --.

Signed and Sealed this
Thirty-first Day of May, 2022

Katherine Kelly Vidal

Katherine Kelly Vidal
*Director of the United States Patent and Trademark Office*